US009725703B2

(12) United States Patent
Whitney et al.

(10) Patent No.: US 9,725,703 B2
(45) Date of Patent: Aug. 8, 2017

(54) FORMULATIONS AND METHODS FOR STABILIZING PCR REAGENTS

(71) Applicant: BIOMATRICA, INC., San Diego, CA (US)

(72) Inventors: Scott E. Whitney, San Diego, CA (US); Stephanie De Los Rios, San Diego, CA (US); Senait Ghirmai, San Diego, CA (US); Rolf Muller, San Diego, CA (US); Vasco Liberal, San Diego, CA (US); Steven P. Wilkinson, San Diego, CA (US)

(73) Assignee: Biomatrica, Inc., San Diego, CA (US)

( * ) Notice: Subject to any disclaimer, the term of this patent is extended or adjusted under 35 U.S.C. 154(b) by 218 days.

(21) Appl. No.: 14/654,457

(22) PCT Filed: Dec. 20, 2013

(86) PCT No.: PCT/US2013/077290
§ 371 (c)(1),
(2) Date: Jun. 19, 2015

(87) PCT Pub. No.: WO2014/100755
PCT Pub. Date: Jun. 26, 2014

(65) Prior Publication Data
US 2015/0329849 A1    Nov. 19, 2015

Related U.S. Application Data

(60) Provisional application No. 61/740,356, filed on Dec. 20, 2012.

(51) Int. Cl.
*C12N 9/12* (2006.01)
*C12N 9/96* (2006.01)
*C12Q 1/68* (2006.01)

(52) U.S. Cl.
CPC ......... *C12N 9/1252* (2013.01); *C12N 9/1247* (2013.01); *C12N 9/96* (2013.01); *C12Q 1/686* (2013.01); *C12Y 207/07006* (2013.01); *C12Y 207/07007* (2013.01)

(58) Field of Classification Search
None
See application file for complete search history.

(56) References Cited

U.S. PATENT DOCUMENTS

| | | |
|---|---|---|
| 3,673,158 A | 6/1972 | Reader et al. |
| 4,024,548 A | 5/1977 | Alonso et al. |
| 4,040,785 A | 8/1977 | Kim et al. |
| 4,127,502 A | 11/1978 | Li Mutti et al. |
| 4,185,964 A | 1/1980 | Lancaster |
| 4,257,958 A | 3/1981 | Powell |
| 4,264,560 A | 4/1981 | Natelson |
| 4,342,740 A | 8/1982 | Narra et al. |
| 4,451,569 A | 5/1984 | Kobayashi et al. |
| 4,473,552 A | 9/1984 | Jost |
| 4,683,195 A | 7/1987 | Mullis et al. |
| 4,683,202 A | 7/1987 | Mullis |
| 4,800,159 A | 1/1989 | Mullis et al. |
| 4,801,428 A | 1/1989 | Homolko et al. |
| 4,806,343 A | 2/1989 | Carpenter et al. |
| 4,842,758 A | 6/1989 | Crutzen |
| 4,889,818 A | 12/1989 | Gelfand et al. |
| 4,891,319 A | 1/1990 | Roser |
| 4,898,813 A | 2/1990 | Albarella et al. |
| 4,933,145 A | 6/1990 | Uchida et al. |
| 4,962,020 A | 10/1990 | Tabor et al. |
| 4,962,022 A | 10/1990 | Fleming et al. |
| 4,965,188 A | 10/1990 | Mullis et al. |
| 4,978,688 A | 12/1990 | Louderback |
| 5,039,704 A | 8/1991 | Smith et al. |
| 5,047,342 A | 9/1991 | Chatterjee |
| 5,071,648 A | 12/1991 | Rosenblatt |
| 5,078,997 A | 1/1992 | Hora et al. |
| 5,079,352 A | 1/1992 | Gelfand et al. |
| 5,089,407 A | 2/1992 | Baker et al. |
| 5,096,670 A | 3/1992 | Harris et al. |
| 5,096,744 A | 3/1992 | Takei et al. |
| 5,098,893 A | 3/1992 | Franks et al. |

(Continued)

FOREIGN PATENT DOCUMENTS

| | | |
|---|---|---|
| CA | 1022441 A1 | 12/1977 |
| CA | 2467563 A1 | 5/2003 |

(Continued)

OTHER PUBLICATIONS

US 8,785,182, 07/2014, Muller-Cohn et al. (withdrawn)
Koumoto et al. (Structural effect of synthetic zwitterionic cosolutes on the stability of DNA duplexes, Tetrahedron, 2008, 64(1), 168-174).*
Wang et al. (Journal of Physical Chemistry B (2012), 116(41), 12479-12488).*
Saiki et al., Primer directed enzymatic amplification of DNA with a thermostable DNA polymerase. Science, New Series, 239(4839):487-491 (1988).
Barnes, The fidelity of Taq polymerase catalyzing PCR is improved by an N-terminal deletion. Gene, 112:29-35 (1992).
Braasch and Corey, Locked nucleic acid (LNA): fine-tuning the recognition of DNA and RNA. Chemistry and Biology, 8:1-7 (2001).

(Continued)

*Primary Examiner* — Suzanne M Noakes
*Assistant Examiner* — Jae W Lee
(74) *Attorney, Agent, or Firm* — Wilson Sonsini Goodrich & Rosati

(57) ABSTRACT

Described herein are stabilized polymerase compositions comprising a polymerase and an polymerase stabilizing agent, such as a non-detergent zwitterionic stabilizer or a cationic ester disclosed, for use in nucleic acid amplification or nucleic acid sequencing. Compositions are provided for the stabilization of one or more polymerases in a single stabilized liquid formulation. Also disclosed are methods for making and using stabilized polymerase compositions and kits for nucleic acid amplification and sequencing comprising the stabilized polymerase compositions provided.

11 Claims, 10 Drawing Sheets

(56) References Cited

U.S. PATENT DOCUMENTS

| | | |
|---|---|---|
| 5,198,353 A | 3/1993 | Hawkins et al. |
| 5,200,399 A | 4/1993 | Wettlaufer et al. |
| 5,240,843 A | 8/1993 | Gibson et al. |
| 5,270,179 A | 12/1993 | Chatterjee |
| 5,290,765 A | 3/1994 | Wettlaufer et al. |
| 5,315,505 A | 5/1994 | Pratt et al. |
| 5,351,801 A | 10/1994 | Markin et al. |
| 5,374,553 A | 12/1994 | Gelfand et al. |
| 5,397,711 A | 3/1995 | Finckh |
| 5,403,706 A | 4/1995 | Wilk et al. |
| 5,409,818 A | 4/1995 | Davey et al. |
| 5,418,141 A | 5/1995 | Zweig et al. |
| 5,428,063 A | 6/1995 | Barak et al. |
| 5,436,149 A | 7/1995 | Barnes |
| 5,455,166 A | 10/1995 | Walker |
| 5,496,562 A | 3/1996 | Burgoyne |
| 5,498,523 A | 3/1996 | Tabor et al. |
| 5,512,462 A | 4/1996 | Cheng |
| 5,516,644 A | 5/1996 | Yamauchi et al. |
| 5,529,166 A | 6/1996 | Markin et al. |
| 5,541,290 A | 7/1996 | Harbeson et al. |
| 5,556,771 A | 9/1996 | Shen et al. |
| 5,593,824 A | 1/1997 | Treml et al. |
| 5,614,365 A | 3/1997 | Tabor et al. |
| 5,614,387 A | 3/1997 | Shen et al. |
| 5,684,045 A | 11/1997 | Smith et al. |
| 5,705,366 A | 1/1998 | Backus |
| 5,728,822 A | 3/1998 | MacFarlane |
| 5,741,462 A | 4/1998 | Nova et al. |
| 5,751,629 A | 5/1998 | Nova et al. |
| 5,763,157 A | 6/1998 | Treml et al. |
| 5,777,099 A | 7/1998 | Mehra |
| 5,777,303 A | 7/1998 | Berney |
| 5,779,983 A | 7/1998 | Dufresne et al. |
| 5,789,172 A | 8/1998 | Still et al. |
| 5,789,414 A | 8/1998 | Lapidot et al. |
| 5,798,035 A | 8/1998 | Kirk et al. |
| 5,814,502 A | 9/1998 | Hoeltke et al. |
| 5,827,874 A | 10/1998 | Meyer et al. |
| 5,834,254 A | 11/1998 | Shen et al. |
| 5,837,546 A | 11/1998 | Allen et al. |
| 5,856,102 A | 1/1999 | Bierke-Nelson et al. |
| 5,861,251 A | 1/1999 | Park et al. |
| 5,874,214 A | 2/1999 | Nova et al. |
| 5,876,992 A | 3/1999 | De Rosier et al. |
| 5,914,272 A | 6/1999 | Dufresne et al. |
| 5,918,273 A | 6/1999 | Horn |
| 5,939,259 A | 8/1999 | Harvey et al. |
| 5,945,515 A | 8/1999 | Chomczynski |
| 5,948,614 A | 9/1999 | Chatterjee |
| 5,955,448 A | 9/1999 | Colaco et al. |
| 5,985,214 A | 11/1999 | Stylli et al. |
| 5,991,729 A | 11/1999 | Barry et al. |
| 6,013,488 A | 1/2000 | Hayashizaki |
| 6,015,668 A | 1/2000 | Hughes et al. |
| 6,017,496 A | 1/2000 | Nova et al. |
| 6,025,129 A | 2/2000 | Nova et al. |
| 6,037,168 A | 3/2000 | Brown |
| 6,050,956 A | 4/2000 | Ikegami et al. |
| 6,057,117 A | 5/2000 | Harrison et al. |
| 6,057,159 A | 5/2000 | Lepre |
| 6,071,428 A | 6/2000 | Franks et al. |
| 6,090,925 A | 7/2000 | Woiszwillo et al. |
| 6,127,155 A | 10/2000 | Gelfand et al. |
| 6,143,817 A | 11/2000 | Hallam et al. |
| 6,153,412 A | 11/2000 | Park et al. |
| 6,153,618 A | 11/2000 | Schultz et al. |
| 6,156,345 A | 12/2000 | Chudzik et al. |
| 6,166,117 A | 12/2000 | Miyazaki |
| 6,168,922 B1 | 1/2001 | Harvey et al. |
| 6,197,229 B1 | 3/2001 | Ando et al. |
| 6,204,375 B1 | 3/2001 | Lader |
| 6,221,599 B1 | 4/2001 | Hayashizaki |
| 6,242,235 B1 | 6/2001 | Shultz et al. |
| 6,251,599 B1 | 6/2001 | Chen et al. |
| 6,258,930 B1 | 7/2001 | Gauch et al. |
| 6,284,459 B1 | 9/2001 | Nova et al. |
| 6,294,203 B1 | 9/2001 | Burgoyne |
| 6,294,338 B1 | 9/2001 | Nunomura |
| 6,310,060 B1 | 10/2001 | Barrett et al. |
| 6,313,102 B1 | 11/2001 | Colaco et al. |
| 6,322,983 B1 | 11/2001 | Burgoyne |
| 6,323,039 B1 | 11/2001 | Dykens et al. |
| 6,329,139 B1 | 12/2001 | Nova et al. |
| 6,331,273 B1 | 12/2001 | Nova et al. |
| 6,352,854 B1 | 3/2002 | Nova et al. |
| 6,366,440 B1 | 4/2002 | Kung |
| 6,372,428 B1 | 4/2002 | Nova et al. |
| 6,372,437 B2 | 4/2002 | Hayashizaki |
| 6,380,858 B1 | 4/2002 | Yarin et al. |
| 6,416,714 B1 | 7/2002 | Nova et al. |
| 6,417,185 B1 | 7/2002 | Goff et al. |
| 6,426,210 B1 | 7/2002 | Franks et al. |
| 6,440,966 B1 | 8/2002 | Barrett et al. |
| 6,447,726 B1 | 9/2002 | Delucas et al. |
| 6,447,804 B1 | 9/2002 | Burgoyne |
| 6,448,245 B1 | 9/2002 | Depetrillo et al. |
| RE37,872 E | 10/2002 | Franks et al. |
| 6,458,556 B1 | 10/2002 | Hayashizaki |
| 6,465,231 B2 | 10/2002 | Harrison et al. |
| 6,475,716 B1 | 11/2002 | Seki |
| 6,489,344 B1 | 12/2002 | Nuss et al. |
| 6,503,411 B1 | 1/2003 | Franks et al. |
| 6,503,702 B1 | 1/2003 | Stewart |
| 6,528,309 B2 | 3/2003 | Levine |
| 6,534,483 B1 | 3/2003 | Bruno et al. |
| 6,535,129 B1 | 3/2003 | Petrick |
| 6,602,718 B1 | 8/2003 | Augello et al. |
| 6,608,632 B2 | 8/2003 | Daly et al. |
| 6,610,531 B1 | 8/2003 | Mateczun et al. |
| 6,617,170 B2 | 9/2003 | Augello et al. |
| 6,627,226 B2 | 9/2003 | Burgoyne et al. |
| 6,627,398 B1 | 9/2003 | Wilusz et al. |
| 6,638,945 B1 | 10/2003 | Gibson |
| 6,645,717 B1 | 11/2003 | Smith et al. |
| 6,649,406 B1 | 11/2003 | Williams et al. |
| 6,653,062 B1 | 11/2003 | Depablo et al. |
| 6,664,099 B1 | 12/2003 | Worrall |
| 6,667,167 B1 | 12/2003 | Sorensen et al. |
| 6,682,730 B2 | 1/2004 | Mickle et al. |
| 6,689,353 B1 | 2/2004 | Wang et al. |
| 6,696,028 B2 | 2/2004 | Bara |
| 6,746,841 B1 | 6/2004 | Fomovskaia et al. |
| 6,746,851 B1 | 6/2004 | Tseung et al. |
| 6,750,059 B1 | 6/2004 | Blakesley et al. |
| 6,776,959 B1 | 8/2004 | Helftenbein |
| 6,787,305 B1 | 9/2004 | Li et al. |
| 6,800,632 B2 | 10/2004 | Nuss et al. |
| 6,803,200 B2 | 10/2004 | Xia et al. |
| 6,821,479 B1 | 11/2004 | Smith et al. |
| 6,821,789 B2 | 11/2004 | Augello et al. |
| 6,852,833 B2 | 2/2005 | Machida et al. |
| 6,858,634 B2 | 2/2005 | Asrar et al. |
| 6,861,213 B2 | 3/2005 | Oelmuller et al. |
| 6,862,789 B1 | 3/2005 | Hering et al. |
| 6,872,357 B1 | 3/2005 | Bronshtein et al. |
| 6,896,894 B2 | 5/2005 | Brody et al. |
| 6,919,172 B2 | 7/2005 | Depablo et al. |
| 6,942,964 B1 | 9/2005 | Ward et al. |
| 6,949,544 B2 | 9/2005 | Bethiel et al. |
| 6,949,547 B2 | 9/2005 | Nuss et al. |
| 7,001,770 B1 | 2/2006 | Atencio et al. |
| 7,001,905 B2 | 2/2006 | Biwersi et al. |
| 7,011,825 B2 | 3/2006 | Yamazaki et al. |
| 7,037,918 B2 | 5/2006 | Nuss et al. |
| 7,045,519 B2 | 5/2006 | Nuss et al. |
| 7,049,065 B2 | 5/2006 | Hayashizaki |
| 7,083,106 B2 | 8/2006 | Albany |
| 7,098,033 B2 | 8/2006 | Chen et al. |
| 7,101,693 B2 | 9/2006 | Cicerone et al. |
| 7,129,242 B2 | 10/2006 | Satoh et al. |
| 7,142,987 B2 | 11/2006 | Eggers |
| 7,150,980 B1 | 12/2006 | Lapidot et al. |
| 7,169,584 B2 | 1/2007 | Ward et al. |

(56) References Cited

U.S. PATENT DOCUMENTS

| | | |
|---|---|---|
| 7,169,816 B2 | 1/2007 | Barrett et al. |
| RE39,497 E | 2/2007 | Franks et al. |
| 7,172,999 B2 | 2/2007 | Mattern et al. |
| 7,258,873 B2 | 8/2007 | Truong-Le et al. |
| 7,270,953 B2 | 9/2007 | Hollaender et al. |
| 7,282,371 B2 | 10/2007 | Helftenbein |
| 7,326,418 B2 | 2/2008 | Franzoso et al. |
| 7,384,603 B2 | 6/2008 | Klein et al. |
| 7,425,557 B2 | 9/2008 | Nuss et al. |
| 7,476,754 B2 | 1/2009 | Herradon et al. |
| 7,521,460 B2 | 4/2009 | Langham et al. |
| 7,592,455 B2 | 9/2009 | Brookings et al. |
| 7,728,013 B2 | 6/2010 | Blatt et al. |
| 7,745,663 B2 | 6/2010 | Isshiki et al. |
| 7,795,256 B2 | 9/2010 | Alexander et al. |
| 7,803,839 B2 | 9/2010 | Aay et al. |
| 7,846,703 B2 | 12/2010 | Kobayashi et al. |
| 7,897,624 B2 | 3/2011 | Yan et al. |
| 7,919,294 B2 | 4/2011 | Franco De Sarabia Rosado et al. |
| 7,932,266 B2 | 4/2011 | Herradon Garcia et al. |
| 7,972,828 B2 | 7/2011 | Ward et al. |
| 8,143,271 B2 | 3/2012 | Ibrahim et al. |
| RE43,389 E | 5/2012 | Helftenbein |
| 8,178,555 B2 | 5/2012 | Chang et al. |
| 8,378,108 B2 | 2/2013 | Corkey et al. |
| 8,394,822 B2 | 3/2013 | Hutchings et al. |
| 8,440,665 B2 | 5/2013 | Corkey et al. |
| 8,492,427 B2 | 7/2013 | Gancia et al. |
| 8,519,125 B2 | 8/2013 | Whitney et al. |
| 8,530,480 B2 | 9/2013 | Kamenecka et al. |
| 8,598,360 B2 | 12/2013 | Corkey et al. |
| 8,642,584 B2 | 2/2014 | Aftab et al. |
| 8,664,244 B2 | 3/2014 | Chen |
| 8,827,874 B2 | 9/2014 | Nishimura |
| 8,900,856 B2 | 12/2014 | Muller-Cohn et al. |
| 9,078,426 B2 | 7/2015 | Muller-Cohn et al. |
| 2001/0038858 A1 | 11/2001 | Roser et al. |
| 2002/0039771 A1 | 4/2002 | Peters et al. |
| 2002/0055118 A1 | 5/2002 | Eym |
| 2002/0076819 A1 | 6/2002 | Bowman et al. |
| 2002/0081565 A1 | 6/2002 | Barnea et al. |
| 2002/0094533 A1 | 7/2002 | Hess et al. |
| 2002/0103086 A1 | 8/2002 | Asrar et al. |
| 2002/0182258 A1 | 12/2002 | Lunsford et al. |
| 2003/0022148 A1 | 1/2003 | Seki |
| 2003/0031697 A1 | 2/2003 | Chudzik et al. |
| 2003/0059468 A1 | 3/2003 | Mattern et al. |
| 2003/0091971 A1 | 5/2003 | Xia et al. |
| 2003/0119042 A1 | 6/2003 | Franco De Sarabia Rosado et al. |
| 2003/0129755 A1 | 7/2003 | Sadler et al. |
| 2003/0138805 A1 | 7/2003 | Loffert et al. |
| 2003/0157088 A1 | 8/2003 | Elliott et al. |
| 2003/0162284 A1 | 8/2003 | Dordick et al. |
| 2003/0163608 A1 | 8/2003 | Tiwary et al. |
| 2003/0165482 A1 | 9/2003 | Rolland et al. |
| 2003/0175232 A1 | 9/2003 | Elliott et al. |
| 2003/0199446 A1 | 10/2003 | Bunger et al. |
| 2003/0215369 A1 | 11/2003 | Eggers et al. |
| 2004/0014068 A1 | 1/2004 | Burgoyne |
| 2004/0058349 A1 | 3/2004 | Van Ness et al. |
| 2004/0101966 A1 | 5/2004 | Davis et al. |
| 2004/0110267 A1 | 6/2004 | Sundar |
| 2004/0121420 A1 | 6/2004 | Smith |
| 2004/0121432 A1 | 6/2004 | Klein et al. |
| 2004/0142475 A1 | 7/2004 | Barman et al. |
| 2004/0208792 A1 | 10/2004 | Linton et al. |
| 2004/0228794 A1 | 11/2004 | Weller et al. |
| 2004/0241713 A1 | 12/2004 | Mirzabekov et al. |
| 2005/0026181 A1 | 2/2005 | Davis et al. |
| 2005/0053911 A1 | 3/2005 | Greener et al. |
| 2005/0086822 A1 | 4/2005 | Frisner et al. |
| 2005/0090009 A1 | 4/2005 | Cormier et al. |
| 2005/0112610 A1 | 5/2005 | Lee et al. |
| 2005/0186254 A1 | 8/2005 | Roser et al. |
| 2005/0196824 A1 | 9/2005 | Fisher et al. |
| 2005/0227269 A1 | 10/2005 | Lloyd et al. |
| 2005/0251501 A1 | 11/2005 | Phillips et al. |
| 2005/0276728 A1 | 12/2005 | Muller-Cohn et al. |
| 2006/0014177 A1 | 1/2006 | Hogan et al. |
| 2006/0099567 A1 | 5/2006 | Muller-Cohn et al. |
| 2006/0127415 A1 | 6/2006 | Mayeresse |
| 2006/0147944 A1 | 7/2006 | Chomczynski |
| 2006/0177855 A1 | 8/2006 | Utermohlen et al. |
| 2006/0183687 A1 | 8/2006 | Cory et al. |
| 2006/0193968 A1 | 8/2006 | Keogh et al. |
| 2006/0198891 A1 | 9/2006 | Ravenelle et al. |
| 2006/0293212 A1 | 12/2006 | Griese et al. |
| 2007/0020289 A1 | 1/2007 | Mattern et al. |
| 2007/0043216 A1 | 2/2007 | Bair, Jr. et al. |
| 2007/0048726 A1 | 3/2007 | Baust et al. |
| 2007/0073039 A1 | 3/2007 | Chisari |
| 2007/0117173 A1 | 5/2007 | Levison et al. |
| 2007/0135528 A1 | 6/2007 | Butler et al. |
| 2007/0212760 A1 | 9/2007 | Lapidot et al. |
| 2007/0243178 A1 | 10/2007 | Ho et al. |
| 2008/0064071 A1 | 3/2008 | Hogrefe et al. |
| 2008/0146790 A1 | 6/2008 | Grolz et al. |
| 2008/0176209 A1 | 7/2008 | Muller et al. |
| 2008/0187924 A1 | 8/2008 | Korfhage et al. |
| 2008/0227118 A1 | 9/2008 | Kohno et al. |
| 2008/0268514 A1 | 10/2008 | Muller et al. |
| 2008/0307117 A1 | 12/2008 | Muller-Cohn et al. |
| 2009/0233283 A1 | 9/2009 | Rashtchian et al. |
| 2009/0239208 A1 | 9/2009 | Mayaudon et al. |
| 2009/0259023 A1 | 10/2009 | Su et al. |
| 2009/0291427 A1 | 11/2009 | Muller-Cohn et al. |
| 2009/0298132 A1 | 12/2009 | Muller-Cohn et al. |
| 2009/0312285 A1 | 12/2009 | Fischer et al. |
| 2010/0099150 A1 | 4/2010 | Fang et al. |
| 2010/0159528 A1 | 6/2010 | Liu et al. |
| 2010/0159529 A1 | 6/2010 | Metzler et al. |
| 2010/0178210 A1 | 7/2010 | Hogan et al. |
| 2010/0196904 A1 | 8/2010 | Arieli et al. |
| 2010/0261252 A1 | 10/2010 | Long et al. |
| 2010/0292447 A1 | 11/2010 | Pitner et al. |
| 2011/0014676 A1 | 1/2011 | Cowan et al. |
| 2011/0027862 A1 | 2/2011 | Bates et al. |
| 2011/0059490 A1 | 3/2011 | Lagunavicius et al. |
| 2011/0081363 A1 | 4/2011 | Whitney et al. |
| 2012/0028933 A1 | 2/2012 | Baust et al. |
| 2012/0052572 A1 | 3/2012 | Whitney et al. |
| 2012/0100522 A1 | 4/2012 | Saghbini et al. |
| 2012/0142070 A1 | 6/2012 | Battrell et al. |
| 2012/0295328 A1 | 11/2012 | Wyrich et al. |
| 2013/0209997 A1 | 8/2013 | Whitney et al. |
| 2014/0065627 A1 | 3/2014 | Whitney et al. |
| 2014/0261474 A1 | 9/2014 | Gonda |

FOREIGN PATENT DOCUMENTS

| | | |
|---|---|---|
| DE | 2424426 A1 | 3/1975 |
| DE | 19834816 A1 | 2/2000 |
| DE | 102008029734 A1 | 12/2009 |
| DE | 102008039734 A1 | 3/2010 |
| EP | 0448146 A1 | 9/1991 |
| EP | 0451924 A2 | 10/1991 |
| EP | 0329822 B1 | 6/1994 |
| EP | 0637750 A2 | 2/1995 |
| EP | 0706825 A1 | 4/1996 |
| EP | 0236069 B1 | 5/1997 |
| EP | 0774464 A2 | 5/1997 |
| EP | 0875292 A1 | 11/1998 |
| EP | 0915167 A1 | 5/1999 |
| EP | 1088060 A1 | 4/2001 |
| EP | 0833611 B1 | 8/2001 |
| EP | 0684315 B1 | 6/2002 |
| EP | 0822861 B1 | 11/2003 |
| EP | 1555033 A2 | 7/2005 |
| EP | 1082006 B1 | 2/2006 |
| EP | 0395736 B2 | 8/2006 |
| EP | 1736542 | 12/2006 |
| EP | 1758932 A2 | 3/2007 |
| EP | 1651712 B1 | 10/2007 |
| EP | 2934572 A2 | 10/2015 |

(56) References Cited

FOREIGN PATENT DOCUMENTS

| | | |
|---|---|---|
| GB | 2129551 A | 5/1984 |
| JP | S62502633 A | 10/1987 |
| JP | H08211065 A | 8/1996 |
| JP | H09127106 A | 5/1997 |
| JP | 2001050872 A | 2/2001 |
| WO | WO-8607462 A1 | 12/1986 |
| WO | WO-8700196 A1 | 1/1987 |
| WO | WO-8701206 A1 | 2/1987 |
| WO | WO-8900012 A1 | 1/1989 |
| WO | WO-8906542 A1 | 7/1989 |
| WO | WO-9005182 A1 | 5/1990 |
| WO | WO-9114773 A2 | 10/1991 |
| WO | WO-9200091 A1 | 1/1992 |
| WO | WO-9206188 A2 | 4/1992 |
| WO | WO-9206200 A1 | 4/1992 |
| WO | WO-9209300 A1 | 6/1992 |
| WO | WO-9206188 A3 | 10/1992 |
| WO | WO-9501559 A2 | 1/1995 |
| WO | WO-9502046 A1 | 1/1995 |
| WO | WO-9510605 A1 | 4/1995 |
| WO | WO-9516198 A1 | 6/1995 |
| WO | WO-9610640 A1 | 4/1996 |
| WO | WO-9636436 A1 | 11/1996 |
| WO | WO-9700670 A1 | 1/1997 |
| WO | WO-9705248 A2 | 2/1997 |
| WO | WO-9715394 A1 | 5/1997 |
| WO | WO-9815355 A2 | 4/1998 |
| WO | WO-9824543 A1 | 6/1998 |
| WO | WO-9960849 A1 | 12/1999 |
| WO | WO-9967371 A1 | 12/1999 |
| WO | WO-0009746 A1 | 2/2000 |
| WO | WO-0014505 A1 | 3/2000 |
| WO | WO-0020117 A2 | 4/2000 |
| WO | WO-0062023 A1 | 10/2000 |
| WO | WO-0076664 A1 | 12/2000 |
| WO | WO-0194016 A1 | 12/2001 |
| WO | WO-03020874 A2 | 3/2003 |
| WO | WO-03020924 A2 | 3/2003 |
| WO | WO-03056293 A2 | 7/2003 |
| WO | WO-2004112476 A1 | 12/2004 |
| WO | WO-2005014704 A1 | 2/2005 |
| WO | WO-2005059178 A1 | 6/2005 |
| WO | WO-2005113147 A2 | 12/2005 |
| WO | WO-2005116081 A2 | 12/2005 |
| WO | WO-2006001499 A2 | 1/2006 |
| WO | WO-2007075253 A2 | 7/2007 |
| WO | WO-2007094581 A1 | 8/2007 |
| WO | WO-2008040126 A1 | 4/2008 |
| WO | WO-2008108549 A1 | 9/2008 |
| WO | WO-2009002568 A2 | 12/2008 |
| WO | WO-2009009210 A2 | 1/2009 |
| WO | WO-2009038853 A2 | 3/2009 |
| WO | WO-2010132508 A2 | 11/2010 |
| WO | WO-2012018639 A2 | 2/2012 |
| WO | WO-2012170907 A2 | 12/2012 |
| WO | WO-2013077290 A1 | 5/2013 |
| WO | WO-2014100755 A2 | 6/2014 |
| WO | WO-2015002729 A2 | 1/2015 |
| WO | WO-2015191632 A1 | 12/2015 |
| WO | WO-2015191633 A1 | 12/2015 |
| WO | WO-2015191634 A1 | 12/2015 |

OTHER PUBLICATIONS

Flaman et al., A rapid PCR fidelity assay. Nucleic Acids Research, 22(15): 3259-3260 (1994).

Gerard et al., cDNA synthesis by moloney murine leukemia virus RNase H-minus reverse transcriptase possessing full DNA polymerase activity. Focus, 14(1): 91-93 (1992).

Gowrishankar et al., Osmoregulation in Enterobacteriaceae: Role of proline/Betaine transport systems. Current Science, 57(5): 225-234 (1988).

Henke et al., Betaine improves the PCR amplification of GC-rich DNA sequences. Nucleic Acids Research, 25(19): 3957-3958 (1997).

Houts et al., Reverse transcriptase from avian myeloblastosis virus. Journal of Virology, 29(2): 517-522 (1979).

Kilger and Paabo, Direct DNA sequence determination from total genomic DNA. Nucleic Acids Research, 25(10): 2032-2034 (1997).

Kotewicz et al., Isolation of closed Moloney murine leukemia virus reverse transcriptase lacking ribonuclease H activity. Nucleic Acid Research, 16(1): 265 (1988).

Lawyer et al., High-level expression, purification, and enzymatic characterization of full-length Thermus aquaticus DNA polymerase and a truncated form deficient in 5' to 3' exonuclease activity. PCR Methods and Applications, Cold Spring Harbor Laboratory Press, 2:275-287 (1993).

Mizuguchi et al., Characterization and application to hot start PCR of neutralizing momoclonal antibodies against KOD DNA polymerase. J.Biochem., 126:762-768 (1999).

Natale et al., Sensitivity of bovine blastocyst gene expression patterns to culture environments assessed by aifferential display RT-PCR. Reproduction, 122(5):687-693 (2001).

Nielsen et al., Peptide nucleis acid (PNA). A DNA mimic with a peptide backbone. Bioconjugate Chemistry, 5:3-7 (1994).

Soltis and Skalka, The alpha and beta chains of avian retrovirus reverse transcriptase independently expressed in *Escherichia coli*: Characterization of enzymatic activities. Proc. Nat. Acad. Sci. USA, 85:3372-3376 (1968).

PCT Patent Application No. PCT/US2013/077290 International Search Report and Written Opinion mailed Jun. 23, 2014.

PCT Patent Application No. PCT/US2013/077290 International Preliminary Report on Patentability mailed Jul. 2, 2015.

Allison et al., "Effects of Drying Methods and Additives on Structure and Function of Actin: Mechanisms of Dehydration-Induced Damage and Its Inhibition," Archives of Biochemistry and Biophysics 358(1):171-181, 1998.

Anchordoquy et al., "Frontiers in Clinical Research—Preservation of DNA," Cell Preservation Technology 5(4):180-188, 2007.

Ando et al., "PLGA Microspheres Containing Plasmid DNA: Preservation of Supercoiled DNA via Cryopreparatin and Carbohydrate Stabilization," Journ. Pharm. Sci., vol. 88, No. 1, pp. 126-130 (1999).

Anonymous, "Transmucosal polymeric molecular delivery systems," retrieved from http://www.antiagingresearch.com/hgh/transmucosal.php on Apr. 7, 2005, 2 pages.

Antibiotics from Prokaryotes. https://www.boundless.com/microbiology/antimicrobial-drugs/commonly-used-antimicrobial-drugs/antibiotics-from-prokaryotes/, downloaded Aug. 1, 2014.

Arakawa et al., "Small molecule pharmacological chaperones: From thermodynamic stabilization to pharmaceutical drugs," Biochimica et Biophysica Acta 1764:1677-1687, 2006.

Are supplements with amino acid chelated minerals better than those with other forms of minerals? https://www.consumerlab.com/answers/Are+supplements+with+amino+acid+chelated+minerals+better+than+those+with+other +forms+of+minerals%3F/amino_acid_mineral_chelates/, downloaded Jul. 31, 2014.

Asano, "Glycosidase inhibitors: update and perspectives on practical use," Glycobiology /3(10):93R-104R, 2003.

Balevicius et al., NMR and quantum chemistry study of mesoscopic effects in ionic liquids. J.Phys.Chem., 114:5365-5371 (2010).

Baskakov et al., "Forcing Thermodynamically Unfolded Proteins to Fold," The Journal of Biological Chemistry, 273(9):4831-4834, 1998.

Borax: Friend or foe? Momsaware.org webpage, http://www.momsaware.org/household-general/139-borax-friend-or-foe.html, downloaded Jul. 31, 2014.

Boyd et al., "Stabilization Effect of Polyvinyl Alcohol on Horseradish Peroxidase, Glucose Oxidase, 13-Galactosidase and Alkaline Phosphatase," Biotechnology Techniques 10(9):693-698, 1996.

Branco et al., Preparation and characterization of new room temperature ionic liquids. Chem.Eur.J. 8:16, p. 3671-3677 (2002).

Buhler et al., "Viral Evolution in Response to the Broad-Based Retroviral Protease Inhibitor TL-3," Journal of Virology 75(19):9502-9508, 2001.

(56) References Cited

OTHER PUBLICATIONS

Calfon et al., IRE1 couples endoplasmic reticulum load to secretory capacity by processing the XBP-1 mRNA. (2002) Nature 415:92-96. doi: 10.1038/415092a (Abstract only).
Carninci et al., "Thermostabilization and thermoactivation of thermolabile enzymes by trehalose and its application for the synthesis of full length cDNA," Proc. Natl. Acad. Sci. USA 95:520-524, 1998.
Carpenter et al., "Stabilization of phosphofructokinase during air-drying with sugars and sugar/transition metal mixtures," Cryobiology 24(5):455-464, 1987. (Abstract).
Catalan et al., "Progress towards a generalized solvent polarity scale: The solvatochromism of 2-(dimethylamino)-7-nitrofluorene and its homomorph 2-fluoro-7-nitrofluorene", Liebigs Ann. 1995(2):241-252 (1995).
Catalan, Solvent effects based on pure solvent scales. In: Handbook of Solvents. Wypych G., ed. Toronto: ChemTec Publishing and New York: William Andrew Publishing. 2001: 583-616.
Cavalieri et al., "Chaperone-like activity of nanoparticles of hydrophobized poly(vinyl alcohol)," Soft Matter 3:718-724, 2007.
Chen et al., "Stabilization of Recombinant Human Keratinocyte Growth Factor by Osmolytes andSalts," Journal of Pharmaceutical Sciences, 85(4):419-426, 1996.
Cheng et al., "Chip PCR. II. Investigation of different PCR amplification systems in microfabricated silicon-glass chips, " Nucleic Acids Res. 24:380-385 (1996).
Cohen et al., "Diffusion NMR Spectroscopy in Supramolecular and Combinatorial Chemistry: An Old Parameter—New Insights," Angew. Chem. Int. Ed., 44: 520-554 (2005).
Dagani, "Stir, Heat—But No Need to Dissolve," Chemical & Engineering News 81(5): 3 pages, 2003.
Dankwardt et al., "Stabilization of enzyme immunoassays for atrazine," Analytica Chimica Acta 362:35-45, 1998.
Daugherty et al., "Formulation and delivery issues for monoclonal antibody therapeutics," Advanced Drug Delivery Reviews 58:686-706, 2006.
De Sanctis et al., "Influence of Glycerol on the Structure and Redox Properties of Horse Heart Cytochrome c. A Circular Dichroism and Electrochemical Study," Journal of Protein Chemistry, 15(7):599-606, 1996.
Degim et al., "Controlled Delivery of Peptides and Proteins," Current Pharmaceutical Design 13:99-117, 2007.
DePaz et al., "Effects of drying methods and additives on the structure, function, and storage stability of subtilisin: role of protein conformation and molecular mobility," Enzyme and Microbial Technology 31:765-774, 2002.
Di Tullio et al., "Molecular recognition by mass spectrometry," J. Mass Spectrom, 40(7):845-865 (2005).
DNA learning center, "Radiation can cause DNA mutations, 3D animation with narration." http://www.dnalc.org/view/15529-Radiation-can-cause-DNA-mutations-3D-animation-with-narration.html, downloaded Aug. 1, 2014.
Dong et al., "Biosynthesis of the Validamycins: Identification of Intermediates in the Biosynthesis of Validamycin A by *Streptomyces hygroscopicus* var. limoneus," J. Am. Chem. Soc. 123:2733-2742, 2001.
Dowell et al. Otitis media—principles of judicious use of antimicrobial agents. Pediatrics. 1998; 101 Suppl. 1: 165-171.
Dowell et al. Principles of judicious use of antimicrobial agents for pediatric upper respiratory tract infections. Pediatrics. 1998; 101 Suppl. 1: 163-165.
Dyke et al., "Solvent-Free Functionalization of Carbon Nanotubes," J. Am. Chem. Soc. 125:1156-1157, 2003.
El-Bashiti, "Trehalose Metabolism in Wheat and Identification of Trehalose Metabolizing Enzymes Under Abiotic Stress Conditions," Thesis, The Graduate School of Natural and Applied Sciences of the Middle East Technical University, Jul. 2003, 140 pages.
Elzie et al., "The N-terminus of thrombospondin: the domain stands apart," The International Journal of Biochemistry & Cell Biology 36:1090-1101, 2004.

EP08826300.9 Supplementary Search Report dated Oct. 26, 2010.
EP10775442.6 Extended European Search Report dated Jan. 21, 2014.
EP11815081.2 Extended European Search Report dated Nov. 5, 2013.
EP11815082.0 Extended European Search Report dated Nov. 5, 2013.
Foods high in glycolic acid. http://www.ehow.com/list_5815634_foods-high-glycolic-acid.html , downloaded Jul. 31, 2014.
Frye et al., "The kinetic basis for the stabilization of staphylococcal nuclease by xylose," Protein Science, 6:789-793, 1997.
Galinski et al., "1,4,5,6-Tetrahydro-2-methyl-4-pyrimidinecarboxylic acid. A novel cyclic amino acid from halophilic phototrophic bacteria of the genus *Ectothiorhodospira*," Eur. J. Biochem., 149:135-139, 1985.
Garcia de Castro et al., "Anhydrobiotic Engineering of Gram-Negative Bacteria," Applied and Environmental Microbiology 66(9):4142-4144, 2000.
Godfrey, "Solvent selection via miscibility number," Chem. Technol. 2(6):359-363(1972).
Goller et al, Protection of a model enzyme (lactate dehydrogenase) against heat, urea and freeze-thaw treatment by compatible solute additives, J. of Molecular Catalsys B: Enzymatic, 7(104):37-45,1999.
Gombotz et al., "Biodegradable Polymers for Protein and Peptide Drug Delivery," Bioconjugate Chem. 6:332-351, 1995.
Green DR, "Apoptosis. Death deceiver," Nature, 396(6712):629-30 (1998).
Green DR, "Apoptotic pathways: the roads to ruin," Cell, 94(6):695-69 (1998).
Green et al., "Mitochondria and apoptosis," Science, 281(5381)1309-12 (1998).
Harding et al., Perk Is Essential for Translational Regulation and Cell Survival during the Unfolded Protein Response. (2000) Mol Cell 5:897-904. doi: 10.1016/s1097-2765(00)80330-5.
Haze et al., Mammalian Transcription Factor ATF6 Is Synthesized as a Transmembrane Protein and Activated by Proteolysis in Response to Endoplasmic Reticulum Stress. (1999) Mol Biol Cell 10(11):3787-3799. doi: 10.1091/mbc.10.11.3787.
Hoffman, "Hydrogels for biomedical applications," Advanced Drug Delivery Reviews 43:3-12, 2002.
Holland et al., "Biological sample collection and processing for molecular epidemiological studies," Mutation Research 543:217-234, 2003.
Holland et al., "Molecular epidemiology biomarkers—Sample collection and processing considerations," Toxicology and Applied Pharmacology 206:261-268, 2005.
Iyer et al, Enzyme stability and stabilization—Aqueous and non-aqueous environment, Process Biochemistry, 43:1019-1032 (2008).
Jones et al., "Long-term storage of DNA-free RNA for use in vaccine studies," BioTechniques 43(5):675-681, 2007.
Kaijalainen et al., "An alternative hot start technique for PCR in small volumes using beads of wax-embedded reaction components dried in trehalose," Nucleic Acids Research 21(12):2959-2960, 1993.
Kameda et al., "New Cyclitols, Degradation of Validamycin A By Flavobacterium Saccharophilum," The Journal of Antibiotics 33(12):1573-1574, 1980.
Kaufman RJ, Orchestrating the unfolded protein response in health and disease. (2002) J Clin Invest 110:1389-1398. doi: 10.1172/jci0216886.
Kim et al., Chemical Biology Investigation of Cell Death Pathways Activated by Endoplasmic Reticulum Stress Reveals Cytoprotective Modulators of ASK1. (2009) J. Biol. Chem. 284(3):1593-1603.
Kirn-Safran et al., "Heparan Sulfate Proteoglycans: Coordinators of Multiple Signaling Pathways during Chondrogenesis," Birth Defects Research (Part C) 72:69-88, 2004.
Knapp et al., "Extrinsic protein stabilization by the naturally occurring osmolytes β-hydroxyectoine and betaine," Extremophiles, 3:191-198, 1999.
Knuesel et al., "Comparative studies of suidatrestin, a specific inhibitor of trehalases," Comparative Biochemistry and Physiology Part B 120:639-646, 1998.

(56) References Cited

OTHER PUBLICATIONS

Komiyama et al., "Hydrolysis of DNA and RNA by lanthanide ions: mechanistic studies leading to new applications," Chem. Commun.:1443-1451, 1999.
Konishi et al., "Effects of Bay m 1099, an a-Glucosidase Inhibitor, on Starch Degradation in Germinating Mung Beans," Biosci. Biotechnol. Biochem. 62(1):142-144, 1998.
Kravitz, Lactate: Not guilty as charged. IDEA Fitness Journal 2(6), 23-25 (2005) http://www.unm.edu/lkravitz/Article/%20folder/lactate.html, 3d paragraph, downloaded Jul. 31, 2014.
Kricka and Wilding, "Microchip PCR," Anal. Bioanal. Chem 377:820-825 (2003).
Kudo et al., A molecular chaperone inducer protects neurons from ER stress. (2008) Cell Death and Differentiation, 15:364-375.
Kumar et al., "The role of proline in the prevention of aggregation during protein folding in vitro," Biochemistry and Molecular Biology International, 46(3):509-517, 1998.
Langer. New methods of drug delivery. Science, New Series, vol. 249, No. 4976 (Sep. 28, 1990), pp. 1527-1533.
Langer, "Polymer-Controlled Drug Delivery Systems," Acc. Chem. Res. 26:537-542, 1993.
Lee et al., "Analysis of the S3 and S3' subsite specificities of feline immunodeficiency virus (FIV) protease: Development of a broad-based protease inhibitor efficacious against FIV, SW, and HIV in vitro and ex vivo," Proc. Natl. Acad. Sci. USA 95:939-944, 1998.
Lee et al., "Development of a New Type of Protease Inhibitors, Efficacious against FIV and HIV Variants," J. Am. Chem. Soc. 121:1145-1155, 1999.
Li et al., "Effect of Mobile Phase Additives on the Resolution of Four Bioactive Compounds by RP-HPLC", Int'l Journal of Molecular Sciences, 11(5):2229-2240 (Jan. 2010).
Liao et al., "The effects of polyvinyl alcohol on the in vitro stability and delivery of spray-dried protein particles from surfactant-free HFA 134a-based pressurised metered dose inhalers," International Journal of Pharmaceutics 304:29-39, 2005.
Loo et al., Peptide and Protein Analysis by Electrospray Ionization-MassSpectrometry and Capillary Electrophoresis-Mass Spectrometry, Anal. Biochem., 179(2):404-412 (1989).
Lou et al., "Increased amplification efficiency of microchip-based PCR by dynamic surface passivation," Biotechniques, vol. 36, No. 2, pp. 248-252 (2004).
Lozano et al., Stabilization of x-Chymotrypsin by iconic liquids in transesterification reactions. Biotechnology and Bioengineerig, 75(5):563-569 (2001).
Luo et al., "Expression of a fusion protein of scFv-biotin mimetic peptide for immunoassay," J. Biotechnol. 65:225 (1998).
Malin et al., "Effect of Tetrahydropyrimidine Derivatives on Protein-Nucleic Acids Interaction," The Journal of Biological Chemistry, 274(11):6920-6929, 1999.
Manzanera et al., "Hydroxyectoine Is Superior to Trehalose for Anhydrobiotic Engineering of Pseudomanas putida KT2440," Applied and Environmental Microbiology 68(9):4328-4333, 2002.
Manzanera et al., "Plastic Encapsulation of Stabilized *Escherichia coli* and Pseudomonas putida," Applied and Environmental Microbiology 70(5):3143-3145, 2004.
Marshall et al.,"NXY-059, a Free Radical-Trapping Agent, Substantially Lessens the Functional Disability Resulting From Cerebral Ischemia in a Primate Species," Stroke, 32:190-198 (2001).
Mascellani et al., "Compatible solutes from hyperthermophiles improve the quality of DNA microarrays," BMC Biotechnology, 7(82):1-6, 2007.
Mitchell et al., "Dispersion of Functionalized Carbon Nanotubes in Polystyrene," Macromolecules 35:8825-8830, 2002.
Mohr, "Reversible chemical reactions as the basis for optical sensors used to detect amines, alcohols and humidity," J. Mater. Chem., 9:2259-2264 (1999).
Mori K, Tripartite Management Mini review of Unfolded Proteins in the Endoplasmic Reticulum. (2000) Cell 101(5):451-454. doi: 10.1016/s0092-8674(00)80855-7.
New England Biolabs 1993/1994, 4 pages.

O'Brien et al. Acute sinusitis—principles of judicious use of antimicrobial agents. Pediatrics. 1998; 101 Suppl. 1: 174-177.
O'Brien et al. Cough illness/bronchitis—principles of judicious use of antimicrobial agents. Pediatrics. 1998; 101 Suppl. 1: 178-181.
Okada et al., Distinct roles of activating transcription factor 6 (ATF6) and double-stranded RNA-activated protein kinase-like endoplasmic reticulum kinase (PERK) in transcription during the mammalian unfolded protein response. (2002) Biochem J 366:585-594. doi: 10.1042/bj20020391.
Ortega et al., "New functional roles for non-collagenous domains of basement membrane collagens," Journal of Cell Science 115:4201-4214, 2002.
Parsegian et al., "Macromolecules and Water: Probing with Osmotic Stress," Methods in Enzymology, 259:43-94, 1995.
Passot et al., "Physical characterization of formulations for the development of two stable freeze-dried proteins during both dried and liquid storage," European Journal of Pharmaceutics and Biopharmaceutics 60:335-348, 2005.
Pavlov et al., "The Role of ECM Molecules in Activity-Dependent Synaptic Development and Plasticity," Birth Defects Research (Part C) 72:12-24, 2004.
PCT/US2014/041396 International Search Report mailed Mar. 13, 2015.
PCT/US2014/042396 International Preliminary Report on Patentability mailed Dec. 23, 2015.
PCT Patent Application No. PCT/US2014/042396 Written Opinion mailed Mar. 13, 2015.
PCT/US2005/012084 International Preliminary Report on Patentability dated Oct. 11, 2006.
PCT/US2005/012084 International Search Report dated Feb. 7, 2006.
PCT/US2006/45661 International Preliminary Report on Patentability dated Jun. 30, 2008.
PCT/US2006/45661 International Search Report and Written Opinion dated Nov. 13, 2007.
PCT/US2008/061332 International Preliminary Report on Patentability dated Oct. 27, 2009.
PCT/US2008/061332 International Search Report and Written Opinion dated Jul. 29, 2009.
PCT/US2008/068628 International Preliminary Report on Patentability dated Jan. 5, 2010.
PCT/US2008/068628 International Search Report and Written Opinion dated Aug. 27, 2009.
PCT/US2010/34454 International Preliminary Report on Patentability dated Nov. 15, 2011.
PCT/US2010/34454 International Search Report and Written Opinion dated Jan. 20, 2011.
PCT/US2011/045404 International Preliminary Report on Patentability dated Jan. 29, 2013.
PCT/US2011/045404 International Search Report and Written Opinion dated Mar. 27, 2012.
PCT/US2011/045405 International Preliminary Report on Patentability dated Jan. 29, 2013.
PCT/US2011/045405 International Search Report and Written Opinion dated Mar. 26, 2012.
Pickering, LK, Ed. 2003 Red Book: Report of the Committee on Infectious Diseases, 26th edition. Elk Grove Village, IL, pp. 695-697.
Prestrelski et al., "Dehydration induced Conformational Transitions in Proteins and Their Inhibition by Stabilizers," Biophysical Journal 65:661-671, 1993.
Roberts, "Organic compatible solutes of halotolerant and halophilic microorganisms," Saline Systems, 1(5):1-30, 2005.
Ron and Walter, Signal integration in the endoplasmic reticulum unfolded protein response. (2007) Nat Rev Mol Cell Biol 8:519-529 (Abstract only).
Rosenstein et al. The common cold—principles of judicious use of antimicrobial agents. Pediatrics. 1998; 101 Suppl. 1: 181-184.
Sadeghi et al., Effect of alkyl chain length and temperature on the thermodynamic properties of ionic liquids 1-alkyl-3-methylimidazolium bromide in aqueous and non-aqueous solutions at different temperatures. J.Chem.Thermodynamics, 41:273-289 (2009).

(56) References Cited

OTHER PUBLICATIONS

Sauer et al., "Bacterial Milking: A Novel Bioprocess for Production of Compatible Solutes," Biotechnology and Bioengineering, 57(3):306-313, 1998.
Sawicki, "Foods high in Glutathione." http://www.ehow.com/list_6900955_foods-high-glutathione.html, downloaded Jul. 31, 2014.
Schwartz et al. Pharyngitis—principles of judicious use of antimicrobial agents. Pediatrics. 1998; 101 Suppl. 1: 171-174.
Schyma, "Erfahrungen mit der PVAL-Methode in der rechtsmedizinischen Praxis," Arch. Kriminol. /97(1-2):41-46, 1996.
Schyma et al., "DNA-PCR Analysis of Bloodstains Samples by the Polyvinyl-Alcohol Method," Journal of Forensic Sciences 44(1):95-99, 1999.
Schyma et al., "The Accelerated Polyvinyl-Alcohol Method for GSR Collection—PVAL 2.0," Journal of Forensic Sciences 45(6)1303-1306, 2000.
Scouten, "A survey of enzyme coupling techniques," Methods in Enzymology, 135:30-65 (1987).
Sigma Catalog. St. Louis:Sigma-Aldrich. p. 1987 (1998).
Sirieix-Plenet et al., "Behaviour of a binary solvent mixture constituted by an amphiphilic ionic liquid, 1-decyl-3-methylimidazolium bromide and water Potentiometric and conductimetric studies," Talanta 63(4):979-986, Jul. 8, 2004.
Slita et al., "DNA-polycation complexes Effect of polycation structure on physico-chemical and biological properties," Journal of Biotechnology, 127:679-693, 2007.
Smith et al., "Optimal Storage Conditions for Highly Dilute DNA Sampled: A Role for Trehalose as a Preserving Agent," Journal of Forensic Science 50(5):1-8, 2005.
Sola-Penna et al., "Carbohydrate protection of enzyme structure and function against guanidinium chloride treatment depends on the nature of carbohydrate and enzyme," Eur. J. Biochem., 248:24-29, 1997.
Suslick et al., "Colorimetric sensor arrays for molecular recognition," Tetrahedron 60:11133-11138 (2004).
The dose makes the poison. Yale chemsafe (http://learn.caim.yale.edu/chemsafe/references/dose.html, downloaded Aug. 1, 2014.
The Frontier energy solution, Inc.'s FAQ, http://www.frontierenergysolutionsinc.com/faq/, downloaded Jul. 31, 2014.
Timasheff, "Water as Ligand: Preferential Binding and Exclusion of Denaturants in Protein Unfolding," Biochemistry, 31(40:9857-9864, 1992.
Stock et al., Effects of ionic liquids on the acetylcholinesterase—a structure-activity relationship consideration. Green Chemistry, 6:286-290 (2004).
U.S. Appl. No. 11/291,267 Office action dated Jun. 13, 2014.
U.S. Appl. No. 12/182,926 Office action dated Apr. 30, 2014.
U.S. Appl. No. 13/191,346 Office action dated Jul. 22, 2014.
U.S. Appl. No. 11/102,588 Notice of Allowance mailed Sep. 24, 2014.
U.S. Appl. No. 11/291,267 Office Action dated Mar. 12, 2015.
U.S. Appl. No. 12/509,303 Final Office action dated Jun. 9, 2014.
U.S. Appl. No. 13/191,346 Office Action dated Mar. 20, 2015.
U.S. Appl. No. 13/812,288 Restriction Requirement mailed Oct. 9, 2014.
U.S. Appl. No. 13/966,117 Final Office Action dated Feb. 26, 2015.
U.S. Appl. No. 13/966,117 Office action dated Sep. 25, 2014.
U.S. Appl. No. 13/191,346 Office Action mailed Jul. 2, 2015.
U.S. Appl. No. 13/812,288 Office Action dated May 7, 2015.
Vanin, "Iron diethyldithiocarbamate as spin trap for nitric oxide detection," Meth. Enzymol., 301:269-79 (1999).
Voziyan et al., "Chaperonin-assisted folding of glutamine synthetase under nonpermissive conditions: Off-pathway aggregation propensity does not determine the co-chaperonin requirement," Protein Science, 9:2405-2412, 2000.
Wang et al., "A Naturally Occurring Protective System in Urea-Rich Cells: Mechanism of Osmolyte Protection of Proteins against Urea Denaturation," Biochemistry, 36:9101-9108, 1997.
Wang et al., "Antibody Structure, Instability, and Formulation," Journal of Pharmaceutical Sciences 96(1):1-26, 2007.
Wang et al., "Instability, stabilization, and formulation of liquid protein pharmaceuticals," International Journal of Pharmaceutics 185:129-188, 1999.
Wang, "Protein aggregation and its inhibition in biopharmaceutics," International Journal of Pharmaceutics 289:1-30, 2005.
Whitman et al., "Prokaryotes: the unseen majority," Proc. Natl. Acad. Sci. USA, 95:6578-83 (1998).
Whittlesey et al., "Delivery systems for small molecule drugs, proteins, and DNA: the neuroscience/biomaterial interface," Experimental Neurology 190:1-16, 2004.
Wierzbicka-Patynowski et al., "The ins and outs of fibronectin matrix assembly," Journal of Cell Science 116:3269-3276, 2003.
Yamamoto et al., "Molecular Design of Bioconjugated Cell Adhesion Peptide with a Water-Soluble Polymeric Modifier for Enhancement of Antimetastatic Effect," Current Drug Targets 3:123-130, 2002.
Yancey et al., "Living with Water Stress: Evolution of Osmolyte Systems," Science, 217:1214-1222, 1982.
Yang et al., Neuroprotection by 2-h postischemia administration of two free radical scavengers, alpha-phenyl-n-tert-butyl-nitrone (PBN) and N-tert-butyl-(2-sulfophenyl)-nitrone (S-PBN), in rats subjected to focal embolic cerebral ischemia., Exp. Neurol., 163(1):39-45 (2000).
Yoshida et al., Identification of the cis-Acting Endoplasmic Reticulum Stress Response Element Responsible for Transcriptional Induction of Mammalian Glucose-regulated Proteins: Involvement of basic leucine zipper transcription factors. (1998) J Biol Chem 273:33741-33749. doi: 10.1074/jbc.273.50.33741.
Zhao et al., "NXY-059, a novel free radical trapping compound, reduces cortical infarction after permanent focal cerebral ischemia in the rat," Brain Res., 909(1-2):46-50 (2001).
Zhi et al., "Renaturation of citrate synthase: Influence of denaturant and folding assistants," Protein Science, 1:522-529, 1992.
PCT Patent Application No. PCT/US2015/034967 International Search Report and Written Opinion dated Sep. 8, 2015.
PCT Patent Application No. PCT/US2015/034968 International Search Report and Written Opinion Mailed Sep. 16, 2015.
PCT Patent Application No. PCT/US2015/034969 International Search Report and Written Opinion dated Sep. 15, 2015.
Peters et al., Sensitivity of human, murine, and rat cells to 5-Fluorouracil and 5'-Deoxy-5-fluorouridine in relation to drug-metabolizing enzymes. Cancer Research, 46:20-28 (1986).
Clement et al. Bioactive isomalabaricane triterpenoids from *Rhabdastrella globostellata* that stabilize the binding of DNA polymerase β to DNA. J. Nat. Prod., 2006, 69(3):373-6.
Clement et al., Following nature's lead: Generating compounds for stabilizing biomolecules. Biopreservation and Biobanking, 2012, 10(4):395-402.
Qu et al., Ambient stable quantitative PCR reagents for the detection of Yersinia pestis. PLoS Neglected Tropical Diseases, 2010, 4(3):e629.
Roche. "PCR Reaction Components." Downloaded from the internet (http://www.roche-appliedscience.com/sis/amplification/pcr_amplification_050300.html); Downloaded on Dec. 13, 2012, 4 pages.
Schnoor, et al. Characterization of the synthetic compatible solute homoectoine as a potent PCR enhancer. Biochem and Biophys. Res. Comm, 2004, 322:867-872.
Spiess et al., Trehalose is a potent Pcr enhancer: Lowering of DNA melting temperature and thermal stabilization of Taq polymerase by the disaccharide trehalose. Clinical Chemistry, 2004, 50:1256-1259.
U.S. Appl. No. 13/812,288 Office Action dated Feb. 11, 2016.

* cited by examiner 3 week stability of liquid-stabilized Roche FastStart Taq at room temperature and 45°C 5 day stability of liquid-stabilized Promega GoTaq at room temperature and 37°C 6 week stability of liquid-stabilized Promega GoTaq at room temperature 3 day stability of liquid-stabilized Promega GoTaq at 45°C

A.

3 week stability of liquid-stabilized Promega GoTaq at 45°C

B 3 week stability of liquid-stabilized Promega GoTaq at 45°C 5 day stability of liquid-stabilized Promega GoTaq at 45°C 5 day stability of liquid-stabilized Promega GoTaq at 45°C 3 day stability of liquid-stabilized Promega GoTaq at 45°C

FORMULATIONS AND METHODS FOR STABILIZING PCR REAGENTS

CROSS REFERENCE TO RELATED APPLICATIONS

This application is filed pursuant to 35 U.S.C. §371 as a U.S. National Phase application of International Application No. PCT/US2013/077290, filed Dec. 20, 2013, which claims the benefit of priority from U.S. Provisional Patent Application No. 61/740,356, filed Dec. 20, 2012, each of which is hereby incorporated by reference in its entirety.

BACKGROUND OF THE INVENTION

Stabilization of polymerases for nucleic acid synthesis and amplification is necessary for long term storage. Polymerases from thermophilic organisms are highly stable enzymes at high temperatures which permit their use in nucleic acid amplification techniques, such as polymerase chain reaction (PCR). Long term storage at room temperature or temperatures above freezing is challenging due to inactivation of the polymerase. Techniques such as lyophilization and the use of non-ionic and ionic detergents and polymerase specific antibodies have been used to stabilize polymerases.

SUMMARY OF THE INVENTION

Described herein are methods and compositions for the stabilization of polymerases for storage. In some embodiments, such polymerases are for use in methods such as nucleic acid amplification (e.g. polymerase chain reaction (PCR) and sequencing). The methods and compositions provide for long term storage of polymerases in liquid form at room temperature. Accordingly, the compositions provided herein do not require lyophilization. In addition, compositions provided herein do not require any cellulose or fibrous matrix components for storage. In some embodiments, the formulations provided herein are employed for room temperature storage. Accordingly, storage at temperatures below room temperature (e.g. at 4° C. or lower) is not required. The compositions provided herein comprise at least one polymerase and a polymerase stabilizing agent disclosed herein. In some embodiments, the polymerase storage stabilizing agent is a non-detergent zwitterionic compound disclosed herein. In some embodiments, the non-detergent zwitterionic compound does not comprise a sulfate group. In some embodiments, the polymerase storage stabilizing agent is a cationic ester compound disclosed herein. In some embodiments, the polymerase storage stabilizing agent is a combination of a zwitterionic compound and a cationic ester compound. In some embodiments, the polymerase storage stabilizing agent is a combination of a non-detergent zwitterionic compound and a cationic ester compound.

The compositions provided herein also include mixtures of reagents at working concentrations suitable for use with or without dilution and maintaining activity upon storage for an extended period of time, wherein the mixture contains at least one polymerase and a polymerase stabilizing agent disclosed herein.

Described herein in certain embodiments, is a liquid composition comprising a polymerase and a storage stabilizing agent wherein the agent stabilizes the polymerase when stored at room temperature for at least two weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, or at least 1 year. In some embodiments, the storage stabilizing agent allows the polymerase to retain the same activity when stored at room temperature for at least two weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, or at least 1 year compared to the activity of the polymerase when stored at a temperature of 4° C. or lower without the storage stabilizing agent. In some embodiments, the storage stabilizing agent allows the polymerase to retain the same activity when stored at room temperature for at least two weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 11 months, or at least 1 year compared to the activity of the polymerase when stored at a temperature of −20° C. without the storage stabilizing agent. In some embodiments, the composition is free of trehalose.

Described herein in certain embodiments, is a liquid composition comprising a polymerase and a storage stabilizing agent wherein the agent stabilizes the polymerase when stored at room temperature for at least two weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, or at least 1 year. In some embodiments, the storage stabilizing agent allows the polymerase to retain the same activity when stored at room temperature for at least two weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, or at least 1 year compared to the activity of the polymerase when stored at a temperature of 4° C. or lower without the storage stabilizing agent. In some embodiments, the storage stabilizing agent allows the polymerase to retain the same activity when stored at room temperature for at least two weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, or at least 1 year compared to the activity of the polymerase when stored at a temperature of −20° C. without the storage stabilizing agent. In some embodiments, the composition is free of trehalose.

In some embodiments, the polymerase storage stabilizing agent is a zwitterionic stabilizer disclosed herein. In some embodiments, the polymerase storage stabilizing agent comprises a compound having the general structure of formula (I):

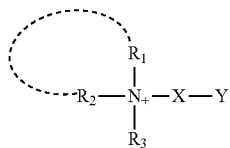

where: $R_1$, $R_2$, $R_3$ each is an alkyl or hydroxyalkyl; or $R_1$ and $R_2$ optionally form a ring; X is $CH_2$, $CH_2$—$CH_2$, $CH_2$—

CH$_2$—CH$_2$, CH$_2$CHOHCH$_2$, —CH(CH$_2$OH)—, —CH$_2$CHOH— or —CH(Z)—, where Z is any side chain typically found in one of the 20 naturally occurring amino acids; and Y is CO$_2$—, or OPO$_3$—. In some embodiments, R$_1$ and R$_2$ form a morpholino ring, pyrrolidinium ring, a pyridinium ring, or a hydroxy pyridinium ring.

In some embodiments, the polymerase storage stabilizing agent comprises a zwitterionic compound, a cationic ester compound, or ionic imidazolium compound set forth in Table 1.

In some embodiments, the polymerase storage stabilizing agent comprises 3-(4-hydroxy-1-methylpiperidinium-1-yl)propanoate.

In some embodiments, the polymerase storage stabilizing agent comprises 3-((2-hydroxyethyl)dimethylammonio)propanoate.

In some embodiments, the polymerase storage stabilizing agent comprises 2-((2-hydroxypropyl)dimethylammonio)acetate.

In some embodiments, the polymerase storage stabilizing agent comprises 3-((2,3-dihydroxypropyl)dimethylammonio)propanoate.

In some embodiments, the polymerase storage stabilizing agent comprises 3-((3-hydroxypropyl)dimethylammonio)propanoate.

In some embodiments, the polymerase storage stabilizing agent comprises 4-(2-ethoxy-2-oxoethyl)-4-methylmorpholin-4-ium bromide.

In some embodiments, the polymerase storage stabilizing agent comprises 1-(2-ethoxy-2-oxoethyl)-1-methylpiperidinium bromide.

In some embodiments, the polymerase storage stabilizing agent comprises 1-(2-ethoxy-2-oxoethyl)-1-methylpyrrolidinium bromide.

In some embodiments, the polymerase storage stabilizing agent comprises 1-(2-ethoxy-2-oxoethyl)-3-hydroxy-1-methylpiperidinium bromide.

In some embodiments, the polymerase storage stabilizing agent comprises N-(2-cyanoethyl)-2-ethoxy-N,N-dimethyl-2-oxoethanaminium bromide.

In some embodiments, the polymerase storage stabilizing agent comprises 2-ethoxy-N,N-diethyl-N-methyl-2-oxoethanaminium bromide.

In some embodiments, the polymerase storage stabilizing agent comprises N-(2-ethoxy-2-oxoethyl)-N,N-dimethylcyclohexanaminium bromide.

In some embodiments, the polymerase storage stabilizing agent comprises 2-ethoxy-N-(2-(2-hydroxyethoxyl)ethyl)-N,N-dimethyl-2-oxoethanaminium bromide.

In some embodiments, the polymerase storage stabilizing agent comprises 1-(2-ethoxy-2-oxoethyl)-3-hydroxy-1-methylpiperidium bromide.

In some embodiments, the polymerase storage stabilizing agent comprises 2-ethoxy-N-(2(2-hydroxyethoxy)ethyl)-N,N-dimethyl-2-oxoethanaminium bromide.

In some embodiments, the polymerase storage stabilizing agent comprises (S)-2-carboxy-1,1-dimethylpyrrolidinium chloride (Proline Betaine Hydrochloride).

In some embodiments, the polymerase storage stabilizing agent comprises 2-(2-(hydroxymethyl)-1-methylpiperidinium-1-yl)acetate.

In some embodiments, the polymerase storage stabilizing agent comprises Alanyl-glutamine.

In some embodiments, the polymerase storage stabilizing agent comprises β-Alanine.

In some embodiments, the polymerase storage stabilizing agent comprises L-Arginine monohydrochloride.

In some embodiments, the polymerase storage stabilizing agent comprises an imidazolium compound. In some embodiments, the imidazolium compound is 3-(2-hydroxyethyl)-1-methyl-1H-imidazol-3-ium bromide or 1-benzyl-3-butyl-1H-imidazol-3-ium bromide.

Also provided herein, in some embodiments, are ready-to-use compositions for the nucleic acid amplification comprising a polymerase, a polymerase storage stabilizing agent disclosed herein, and one or more reagents necessary for performing a nucleic acid amplification method. In some embodiments, the compositions provided herein comprise an additional polymerase stabilizing agent which stabilizes the polymerase during the steps of the nucleic acid amplification method. In some embodiments, the additional stabilizing agent for nucleic acid amplification is an non-ionic detergent.

In some embodiments, the compositions provided herein comprise reagents for performing a nucleic acid amplification method. In some embodiments, the nucleic acid amplification method is a polymerase chain reaction (PCR) method. In some embodiments, the nucleic acid amplification method is a reverse transcription polymerase chain reaction (PCR) method. In some embodiments, the nucleic acid amplification method is a linear amplification method. In some embodiments, the reagents comprise a buffer. In some embodiments, the reagents comprise a non-ionic detergent. In some embodiments, the reagents comprise at least one dNTP. In some embodiments, the reagents comprise a primer.

In some embodiments, the polymerase storage stabilizing agent comprises a compound of formula (I), (II), (III), or (IV). In some embodiments, the polymerase storage stabilizing agent comprises a compound of Table 1. In some embodiments, the polymerase storage stabilizing agent comprises two or more compounds of Table 1. In some embodiments, the polymerase storage stabilizing agent comprises a compound of Table 1 and an further comprises an additional storage stabilizing agent. In some embodiments, the further storage stabilizing agent is a zwitterionic compound or a cationic ester compound. In some embodiments, the compositions provided herein comprise a polysaccharide. In some embodiments, the compositions provided herein comprise a disaccharide, a trisaccharide, or a combination of a disaccharide and a trisaccharide. In some embodiments, the disaccharide is sucrose. In some embodiments, the trisaccharide is melezitose or raffinose. In some embodiments, the composition comprises a polymer. In some embodiments, the polymer is polyvinyl alcohol (PVA). In some embodiments, the compositions provided herein comprise about 0.5-10% Sucrose. In some embodiments, the compositions provided herein comprise 0.5-10% Melezitose. In some embodiments, the compositions provided herein comprise 0.1-1% PVA. In some embodiments, the compositions provided herein comprise BSA. In some embodiments, the compositions provided herein do not comprise BSA. In some embodiments, the compositions provided herein comprise a buffering agent. In some embodiments, the buffering agent maintaining the composition at a pH of from about 6 to about 9. In some embodiments, the buffering agent is selected from the among Tris, MOPS, HEPES, TAPS, Bicine, Tricine, TES, PIPES, MES. In some embodiments, the buffering agent is Tris. In some embodiments, the storage stabilizing agent comprises Alanyl-Glutamine. In some embodiments, the storage stabilizing agent comprises 2-ethoxy-N-(2(2-hydroxyethoxy)ethyl)-N,N-dimethyl-2-oxoethanaminium bromide. In some embodiments, the storage stabilizing agent comprises Alanyl-Glutamine and 2-ethoxy-N-(2(2-hydroxyethoxy)ethyl)-N,N-dimethyl-2-oxoethanaminium bromide.

In some embodiments, the polymerase is a hot-start polymerase. In some embodiments, the polymerase is a chemically modified hot-start polymerase. In some embodiments, the chemically modified hot-start polymerase is hot start Taq polymerase. In some embodiments, the polymerase is an antibody modified hot start polymerase. In some embodiments, the antibody modified hot start polymerase is a GoTaq polymerase. In some embodiments, the polymerase one or more of *Thermus thermophilus* (Tth) DNA polymerase, *Thermus aquaticus* (Taq) DNA polymerase, *Thermotoga neopalitana* (Tne) DNA polymerase, *Thermotoga maritima* (Tma) DNA polymerase, *Thermococcus litoralis* (Tli or VENT™) DNA polymerase, *Thermus eggertssonii* (Teg) DNA polymerase, *Pyrococcus furiosus* (Pfu) DNA polymerase, DEEPVENT. DNA polymerase, *Pyrococcus woosii* (Pwo) DNA polymerase, *Pyrococcus* sp KDD2 (KOD) DNA polymerase, *Bacillus sterothermophilus* (Bst) DNA polymerase, *Bacillus caldophilus* (Bea) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME) DNA polymerase, *Methanobacterium thermoautotrophicum* (Mth) DNA polymerase, *mycobacterium* DNA polymerase (Mtb, Mlep), or mutants, variants or derivatives thereof. In some embodiments, the polymerase has reverse transcriptase activity. In some embodiments, the polymerase is an RNA polymerase.

In some embodiments, the storage stabilizing agent allows the polymerase to retain the same activity when stored at room temperature for at least two weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, or at least 1 year compared to the activity of the polymerase when stored at a temperature of 4° C. or lower for the same time period.

In some embodiments, the storage stabilizing agent allows the polymerase to retain the same activity when stored at a room temperature for at least two weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, or at least 1 year compared to the activity of the polymerase when stored at a temperature of −20° C. for the same time period.

In some embodiments, the storage stabilizing agent allows the polymerase to retain the same activity when stored at a room temperature for at least two weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, or at least 1 year compared to the activity of the polymerase when stored at a temperature of −20° C. for the same time period.

In some embodiments, the storage stabilizing agent allows the polymerase to retain the same activity when stored at a temperature of 37° C. for at least two weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, or at least 1 year compared to the activity of the polymerase when stored at a temperature of 4° C. or lower for the same time period.

In some embodiments, the storage stabilizing agent allows the polymerase to retain the same activity when stored at a temperature of 37° C. for at least two weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, or at least 1 year compared to the activity of the polymerase when stored at a temperature of 4° C. or lower for the same time period.

In some embodiments, the storage stabilizing agent allows the polymerase to retain the same activity when stored at a temperature of about 37° C. for at least two weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, or at least 1 year compared to the activity of the polymerase when stored at a temperature of −20° C. for the same time period.

In some embodiments, the storage stabilizing agent allows the polymerase to retain the same activity when stored at a temperature of 37° C. for at least two weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, or at least 1 year compared to the activity of the polymerase when stored at a temperature of −20° C. for the same time period.

In some embodiments, the storage stabilizing agent comprises a zwitterionic compound that is not a detergent. In some embodiments, the storage stabilizing agent comprises a zwitterionic compound that is not a detergent not a surfactant. In some embodiments, the storage stabilizing agent comprises a zwitterionic compound that dies not comprise a sulfate group.

In some embodiments, the storage stabilizing agent comprises a zwitterionic compound having the general structure of formula (II):

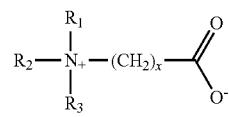

where: $R_1$, $R_2$, $R_3$ each is an alkyl or hydroxyalkyl; or $R_1$ and $R_2$ optionally form a ring; and X is 1, 2, or 3.

In some embodiments, the storage stabilizing agent comprises a cationic ester compound having the general structure of formula (III):

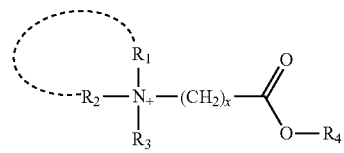

where $R_1$, $R_2$ and $R_3$ are each independently selected from alkyl or hydroxyalkyl; or R1 and R2 optionally form a ring; $R_4$ is a short chain alkyl or branched alkyl; and X is 1, 2, or 3.

In some embodiments, the storage stabilizing agent comprises a cationic ester compound having the general structure of formula (IV):

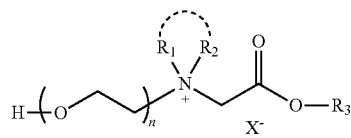

where $R_1$ is methyl, ethyl, propyl, 2-hydroxyethyl, 2-hydroxypropyl, 3-hydroxypropyl or 2,3-dihydroxypropyl; $R_2$ is independently methyl, ethyl, propyl, 2-hydroxyethyl, 2-hydroxypropyl, 3-hydroxypropyl or 2,3-dihydroxypropyl; $R_1$ and $R_2$ optionally joined to form a 5 or 6 membered ring; $R_3$ is methyl, ethyl, 1-propyl or 2-propyl; n is an integer from 1 to 16; and $X^-$ is any acceptable counter ion as examples chloride, bromide, iodide, acetate, sulfate, hydrogensulfate, triflate, dicyanamide, methanesulfonate, nitrate, tetrafluoroborate, thiocyanate, tosylate, hexafluorophosphate, or bis(trifluoromethylsulfonyl)imide.

Also provided herein is are liquid compositions comprising a polymerase and a cationic imidazolium compound. In some embodiments, the cationic imidazolium compound is selected from among 3-(2-hydroxyethyl)-1-methyl-1H-imidazol-3-ium bromide and 1-benzyl-3-butyl-1H-imidazol-3-ium bromide. In some embodiments, the composition further comprises a cationic ester.

In some embodiments, the cationic ester is 2-Ethoxy-N-(2-(2-hydroxyethoxyl)ethyl)-N,N-dimethyl-2-oxoethanaminium bromide. In some embodiments, the composition further comprises a zwitterionic compound. In some embodiments, the zwitterionic compound is alanyl-glutamine. In some embodiments, the zwitterionic compound allows the polymerase to retain the same activity when stored at room temperature for at least two weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, or at least 1 year compared to the activity of the polymerase when stored at a temperature of −20° C. for the same time period. In some embodiments, the composition further comprises a polysaccharide, a polymer, a buffering agent or any combination thereof. In some embodiments, the composition further comprises one or more additional reagents for performing a nucleic acid synthesis method.

DETAILED DESCRIPTION OF THE INVENTION

Figure 1:
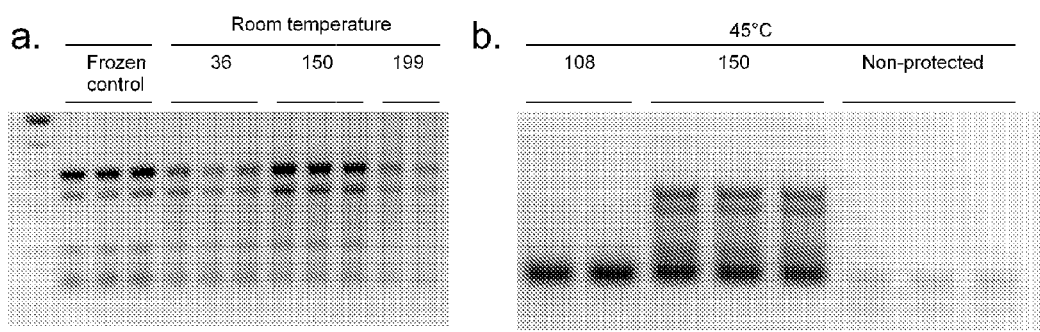
FIG. 1 illustrates 3 week stability of liquid-stabilized Roche FastStart Taq at room temperature and 45° C.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

Certain Terminology

Unless defined otherwise, all technical and scientific terms used herein have the same meaning as is commonly understood by one of skill in the art to which the claimed subject matter belongs. All patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information. Generally, the procedures for cell culture, cell infection, antibody production and molecular biology methods are methods commonly used in the art. Such standard techniques can be found, for example, in reference manual, such as, for example, Sambrook et al. (2000) and Ausubel et al. (1994).

As used herein, the singular forms "a," "an" and "the" include plural referents unless the context clearly dictates otherwise. In this application, the use of the singular includes the plural unless specifically stated otherwise. As used herein, the use of "or" means "and/or" unless stated otherwise. Furthermore, use of the term "including" as well as other forms (e.g., "include", "includes", and "included") is not limiting.

As used herein, ranges and amounts can be expressed as "about" a particular value or range. About also includes the exact amount. Hence "about 40 mg" means "about 40 mg" and also "40 mg." Generally, the term "about" includes an amount that would be expected to be within experimental error.

As used herein, a non-detergent or non-surfactant zwitterionic compound is a zwitterionic compound that comprises a hydrophilic group and a short hydrophobic group (e.g. less than about 5 carbons in a linear chain). As used herein, a non-detergent or non-surfactant zwitterionic compound does not have the ability to aggregate to form micelles.

As used herein, the terms "stabilization," "stabilizing," and "stabilized," when used in reference to enzyme activity refer to the ability of a material to maintain, enhance, or otherwise inhibit the decline or loss of the activity of an enzyme, often as measured over time (i.e., in the presence of a stabilizer, an enzyme retains its activity for a longer time period than the enzyme in the absence of the stabilizer). "Stabilization of enzyme activity" also refers to the ability of a material to maintain the activity of an enzyme under suboptimal conditions of temperature or pH. As another example, "stabilizing enzyme activity" refers to the ability of a material to enhance enzyme activity under suboptimal conditions, as compared to activity in the absence of a "stabilizing" compound or material.

The term "polymerase" refers to an enzyme that synthesizes nucleic acid stands (e.g., RNA or DNA) from ribonucleoside triphosphates or deoxynucleoside triphosphates.

As used herein, "nucleic acid" refers to both, a deoxyribonucleic acid (DNA) and a ribonucleic acid (RNA), as well as modified and/or functionalized versions thereof. Similarly, the term "nucleotide" as used herein includes both individual units of ribonucleic acid and deoxyribonucleic acid as well as nucleoside and nucleotide analogs, and modified nucleotides such as labeled nucleotides. In addition, "nucleotide" includes non-naturally occurring analogue structures, such as those in which the sugar, phosphate, and/or base units are absent or replaced by other chemical structures. Thus, the term "nucleotide" encompasses individual peptide nucleic acid (PNA) (Nielsen et al., Bioconjug. Chem. 1994; 5(1):3-7) and locked nucleic acid (LNA) (Braasch and Corey, Chem. Biol. 2001; 8(1):1-7)) units as well as other like units.

Definition of standard chemistry terms may be found in reference works, including Carey and Sundberg "ADVANCED ORGANIC CHEMISTRY 4TH ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification.

An "alkyl" group refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group that has at least one carbon-carbon double bond, and an "alkyne" moiety refers to a group that has at least one carbon-carbon triple bond. The alkyl moiety, whether saturated or unsaturated, may be branched, straight chain, or cyclic. Depending on the structure, an alkyl group can be a monoradical or a diradical (i.e., an alkylene group). The alkyl group could also be a "lower alkyl" having 1 to 6 carbon atoms.

As used herein, $C_1$-$C_x$ includes $C_1$-$C_2$, $C_1$-$C_3$ . . . $C_1$-$C_x$.

The "alkyl" moiety may have 1 to 10 carbon atoms (whenever it appears herein, a numerical range such as "1 to 10" refers to each integer in the given range; e.g., "1 to 10 carbon atoms" means that the alkyl group may have 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from among methyl, ethyl, propyl, iso-propyl, n-butyl, iso-butyl, sec-butyl, and t-butyl. Thus $C_1$-$C_4$ alkyl includes $C_1$-$C_2$ alkyl and $C_1$-$C_3$ alkyl. Alkyl groups can be substituted or unsubstituted. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

As used herein, the term "non-cyclic alkyl" refers to an alkyl that is not cyclic (i.e., a straight or branched chain containing at least one carbon atom). Non-cyclic alkyls can be fully saturated or can contain non-cyclic alkenes and/or alkynes. Non-cyclic alkyls can be optionally substituted.

The term "alkenyl" refers to a type of alkyl group in which the first two atoms of the alkyl group form a double bond that is not part of an aromatic group. That is, an alkenyl group begins with the atoms —C(R)=C(R)—R, wherein R refers to the remaining portions of the alkenyl group, which may be the same or different. The alkenyl moiety may be branched, straight chain, or cyclic (in which case, it would also be known as a "cycloalkenyl" group). Depending on the structure, an alkenyl group can be a monoradical or a diradical (i.e., an alkenylene group). Alkenyl groups can be optionally substituted. Non-limiting examples of an alkenyl group include —CH=CH$_2$, —C(CH$_3$)=CH$_2$, —CH=CHCH$_3$, —C(CH$_3$)=CHCH$_3$. Alkenylene groups include, but are not limited to, —CH=CH—, —C(CH$_3$)=CH—, —CH=CHCH$_2$—, —CH=CHCH$_2$CH$_2$— and —C(CH$_3$)=CHCH$_2$—. Alkenyl groups could have 2 to 10 carbons. The alkenyl group could also be a "lower alkenyl" having 2 to 6 carbon atoms.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which may be the same or different. The "R" portion of the alkynyl moiety may be branched, straight chain, or cyclic. Depending on the structure, an alkynyl group can be a monoradical or a diradical (i.e., an alkynylene group). Alkynyl groups can be optionally substituted. Non-limiting examples of an alkynyl group include, but are not limited to, —C≡CH, —C≡CCH$_3$, —C≡CCH$_2$CH$_3$, —C≡C—, and —C≡CCH$_2$—. Alkynyl groups can have 2 to 10 carbons. The alkynyl group could also be a "lower alkynyl" having 2 to 6 carbon atoms.

An "alkoxy" group refers to a (alkyl)O— group, where alkyl is as defined herein.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

An "alkenyloxy" group refers to a (alkenyl)O— group, where alkenyl is as defined herein.

The term "alkylamine" refers to the —N(alkyl)$_x$H$_y$ group, where x and y are selected from among x=1, y=1 and x=2, y=0. When x=2, the alkyl groups, taken together with the N atom to which they are attached, can optionally form a cyclic ring system.

"Alkylaminoalkyl" refers to an alkyl radical, as defined herein, substituted with an alkylamine, as defined herein.

An "amide" is a chemical moiety with the formula —C(O)NHR or —NHC(O)R, where R is selected from among alkyl, cycloalkyl, aryl, heteroaryl (bonded through a ring carbon) and heteroalicyclic (bonded through a ring carbon). An amide moiety may form a linkage between an amino acid or a peptide molecule and a compound described herein, thereby forming a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e. a heteroatom). Heterocycle includes heteroaryl and heterocycloalkyl. Carbocycles and heterocycles can be optionally substituted.

The term "aromatic" refers to a planar ring having a delocalized π-electron system containing 4n+2π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

An "aryloxy" group refers to an (aryl)O— group, where aryl is as defined herein.

"Aralkyl" means an alkyl radical, as defined herein, substituted with an aryl group. Non-limiting aralkyl groups include, benzyl, phenethyl, and the like.

"Aralkenyl" means an alkenyl radical, as defined herein, substituted with an aryl group, as defined herein.

The term "cycloalkyl" refers to a monocyclic or polycyclic radical that contains only carbon and hydrogen, and may be saturated, partially unsaturated, or fully unsaturated. Cycloalkyl groups include groups having from 3 to 10 ring atoms. Illustrative examples of cycloalkyl groups include the following moieties:

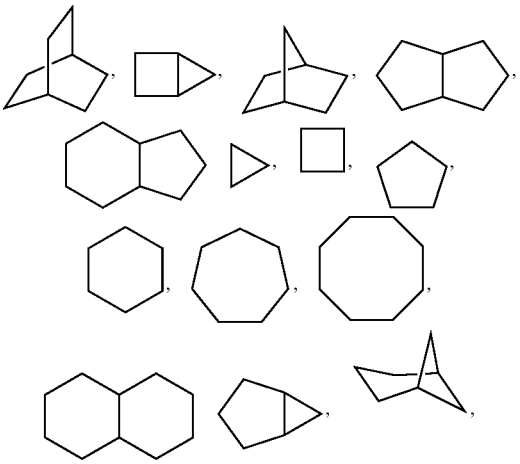

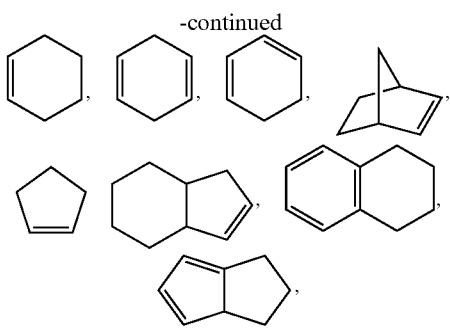

and the like. Depending on the structure, a cycloalkyl group can be a monoradical or a diradical (e.g., an cycloalkylene group). The cycloalkyl group could also be a "lower cycloalkyl" having 3 to 8 carbon atoms.

"Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Illustrative examples of heteroaryl groups include the following moieties:

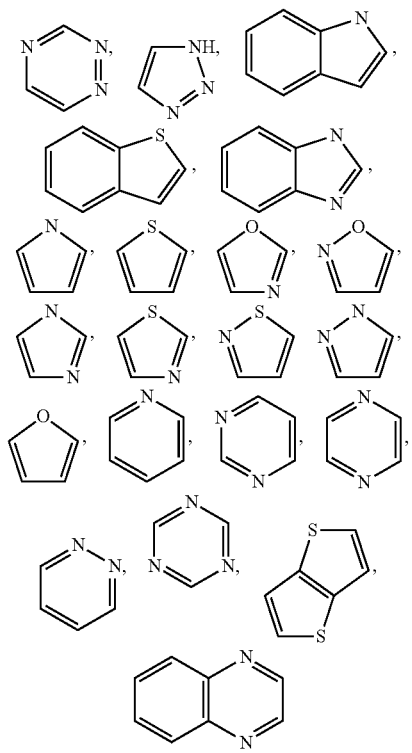

and the like. Depending on the structure, a heteroaryl group can be a monoradical or a diradical (i.e., a heteroarylene group).

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. The radicals may be fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

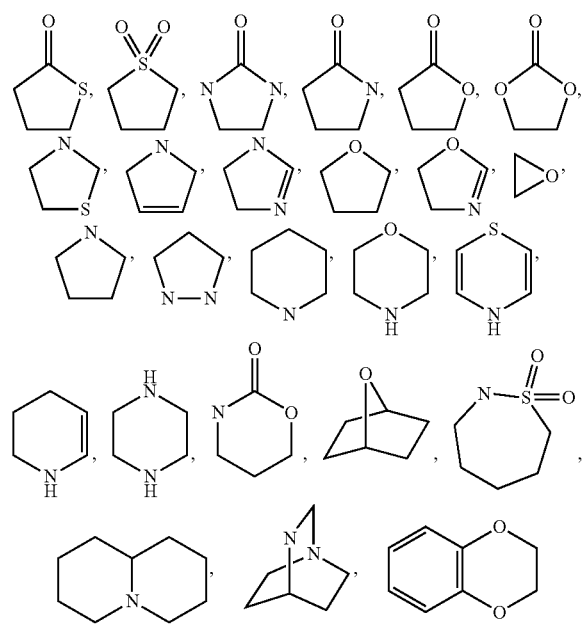

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

The term "halo" or, alternatively, "halogen" or "halide" means fluoro, chloro, bromo and iodo.

The terms "haloalkyl," "haloalkenyl," "haloalkynyl" and "haloalkoxy" include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

The term "fluoroalkyl," as used herein, refers to alkyl group in which at least one hydrogen is replaced with a fluorine atom. Examples of fluoroalkyl groups include, but are not limited to, —CF$_3$, —CH$_2$CF$_3$, —CF$_2$CF$_3$, —CH$_2$CH$_2$CF$_3$ and the like.

As used herein, the terms "heteroalkyl" "heteroalkenyl" and "heteroalkynyl" include optionally substituted alkyl, alkenyl and alkynyl radicals in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. In addition, up to two heteroatoms may be consecutive, such as, by way of example, —CH$_2$—NH—OCH$_3$ and —CH$_2$—O—Si(CH$_3$)$_3$.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, cycloalkyl, aryl, heteroaryl (bonded through a ring carbon) and non-aromatic heterocycle (bonded through a ring carbon).

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, acyl, nitro, haloalkyl, fluoroalkyl, amino, including mono- and di-substituted amino groups, and the protected derivatives thereof.

Compositions and Methods for Polymerase Stabilization

Provided herein are methods and compositions for the stabilization of polymerases for use in methods such as nucleic acid amplification (e.g. polymerase chain reaction (PCR) and sequencing. The methods and compositions provide for long term storage of polymerases at room temperature. In addition, the methods and compositions provide for stable storage of polymerases in liquid form with little or no lyophilization step required. In some embodiments, rehydration of the compositions prior to use, is not required. This feature decreases the potential for contamination of samples, which negatively affect sensitive procedures such as PCR.

In some embodiments, the compositions provided herein comprise at least one polymerase and a polymerase stabilizing agent disclosed herein. In some embodiments, the compositions provided herein comprise a polymerase stabilizing agent that is a zwitterionic compound disclosed herein. In some embodiments, the polymerase stabilizing agent is a non-surfactant zwitterionic compound disclosed herein. In some embodiments, the polymerase stabilizing agent is a non-detergent zwitterionic compound disclosed herein. In some embodiments, the polymerase stabilizing agent is a zwitterionic compound that does not contain a sulfate group. In some embodiments, the compositions provided herein comprise a polymerase stabilizing agent that is a cationic ester compound disclosed herein.

In some embodiments, the compositions provided herein consist essentially of at least one polymerase and a polymerase stabilizing agent disclosed herein. In some embodiments, the polymerase stabilizing agent is a zwitterionic compound disclosed herein. In some embodiments, the polymerase stabilizing agent is a non-surfactant zwitterionic compound disclosed herein. In some embodiments, the polymerase stabilizing agent is a non-detergent zwitterionic compound disclosed herein. In some embodiments, the polymerase stabilizing agent is a zwitterionic compound that does not contain a sulfate group. In some embodiments, the polymerase stabilizing agent is a cationic ester compound disclosed herein.

In some embodiments, a first composition comprising a polymerase stabilizing agent provided herein is mixed with a second composition comprising a polymerase. In some embodiments, the polymerase stabilizing agent is a zwitterionic compound disclosed herein. In some embodiments, the polymerase stabilizing agent is a non-surfactant zwitterionic compound disclosed herein. In some embodiments, the polymerase stabilizing agent is a non-detergent zwitterionic compound disclosed herein. In some embodiments, the polymerase stabilizing agent is a zwitterionic compound that does not contain a sulfate group. In some embodiments, the polymerase stabilizing agent is a cationic ester compound disclosed herein.

In some embodiments, the polymerase storage stabilizing agent comprises a compound having the general structure of formula (I):

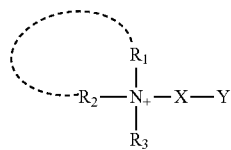

where: $R_1$, $R_2$, $R_3$ each is an alkyl or hydroxyalkyl; or $R_1$ and $R_2$ optionally form a ring; X is $CH_2$, $CH_2$—$CH_2$, $CH_2$—$CH_2$—$CH_2$, $CH_2CHOHCH_2$, —$CH(CH_2OH)$—, —$CH_2CHOH$— or —$CH(Z)$—, where Z is any side chain typically found in one of the 20 naturally occurring amino acids; and Y is $CO_2$—, or $OPO_3$—. In some embodiments, $R_1$ and R2 form a morpholino ring, pyrrolidinium ring, a pyridinium ring, or a hydroxy pyridinium ring.

In some embodiments, the compositions provided herein comprise a polymerase storage stabilizing agent that is a zwitterionic compound having the general structure of formula (II):

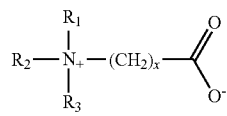

where $R_1$, $R_2$, $R_3$ each is alkyl, such as methyl or ethyl, hydroxyalkyl, such as hydroxyethyl or 2-hydroxypropyl; or $R_1$ and $R_2$ optionally form a ring, such as a morpholino ring, pyrrolidinium ring, a pyridinium ring, or a hydroxy pyridinium ring; and X is 1, 2, or 3.

In some embodiments, the storage stabilizing agent comprises a cationic ester compound having the general structure of formula (III):

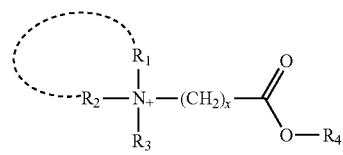

where $R_1$, $R_2$ and $R_3$ are each independently selected from alkyl or hydroxyalkyl; or $R_1$ and $R_2$ optionally form a ring; R4 is a short chain alkyl or branched alkyl; and X is 1, 2, or 3.

In some embodiments, the storage stabilizing agent comprises a cationic compound having the general structure of formula (IV):

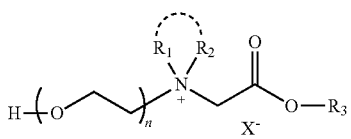

where $R_1$ is methyl, ethyl, propyl, 2-hydroxyethyl, 2-hydroxypropyl, 3-hydroxypropyl or 2,3-dihydroxypropyl; $R_2$ is independently methyl, ethyl, propyl, 2-hydroxyethyl, 2-hydroxypropyl, 3-hydroxypropyl or 2,3-dihydroxypropyl; $R_1$ and $R_2$ optionally joined to form a 5 or 6 membered ring; $R_3$ is methyl, ethyl, 1-propyl or 2-propyl; n is an integer from 1 to 16; and $X^-$ is any suitable counter ion such as, for example chloride, bromide, iodide, acetate, sulfate, hydrogensulfate, triflate, dicyanamide, methanesulfonate, nitrate, tetrafluoroborate, thiocyanate, tosylate, hexafluorophosphate, or bis(trifluoromethylsulfonyl)imide.

In some embodiments, the polymerase storage stabilizing agent of formula (I), (II), (III), or (IV) comprises at least one or two methyl groups attached to the nitrogen.

In some embodiments, the polymerase storage stabilizing agent is selected from one of more compounds set forth in Table 1.

TABLE 1

| Compound # | Structure | Name |
| --- | --- | --- |
| 102 | 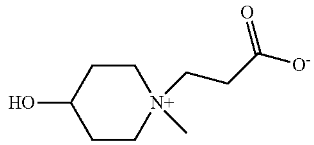 | 3-(4-hydroxy-1-methylpiperidinium-1-yl)propanoate |
| 111 | 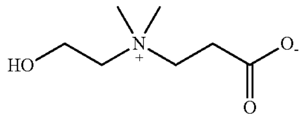 | 3-((2-hydroxyethyl)dimethylammonio)propanoate |
| 116 | 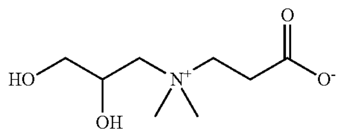 | 3-((2,3-dihydroxypropyl)dimethylammonio)propanoate |
| 129 | 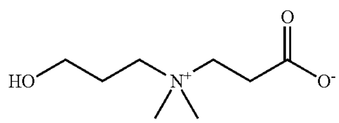 | 3-((3-hydroxypropyl)dimethylammonio)propanoate |
| 135 | 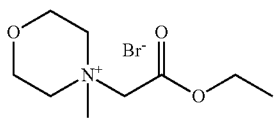 | 4-(2-ethoxy-2-oxoethyl)-4-methylmorpholin-4-ium bromide |
| 136 | 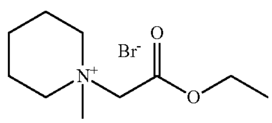 | 1-(2-ethoxy-2-oxoethyl)-1-methylpiperidinium bromide |
| 137 | 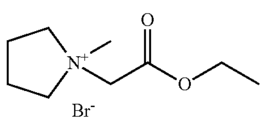 | 1-(2-ethoxy-2-oxoethyl)-1-methylpyrrolidinium bromide |
| 138 | 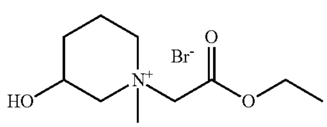 | 1-(2-ethoxy-2-oxoethyl)-3-hydroxy-1-methylpiperidinium bromide |
| 142 | 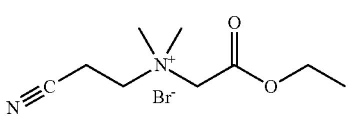 | N-(2-cyanoethyl)-2-ethoxy-N,N-dimethyl-2-oxoethanaminium bromide |
| 143 | 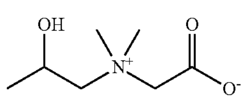 | 2-((2-hydroxypropyl)dimethylammonio) acetate |
| 144 | 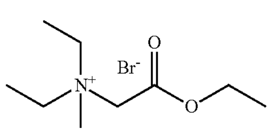 | 2-ethoxy-N,N-diethyl-N-methyl-2-oxoethanaminium bromide |
| 146 | 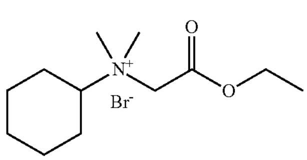 | N-(2-ethoxy-2-oxoethyl)-N,N-dimethylcyclohexanaminium bromide |

TABLE 1-continued

| Compound # | Structure | Name |
|---|---|---|
| 147 | 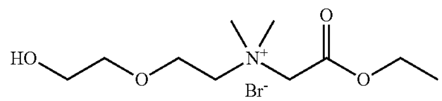 | 2-ethoxy-N-(2-(2-hydroxyethoxy)ethyl)-N,N-dimethyl-2-oxoethanaminium bromide |
| 162 | 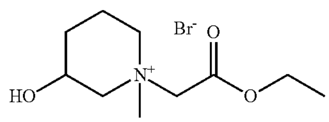 | 1-(2-ethoxy-2-oxoethyl)-3-hydroxy-1-methylpiperidium bromide |
| 155 | 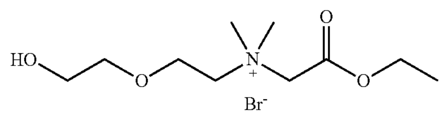 | 2-ethoxy-N-(2(2-hydroxyethoxy)ethyl)-N,N-dimethyl-2-oxoethanaminium bromide |
| | | (S)-2-carboxy-1,1-dimethylpyrrolidinium chloride (Proline Betaine Hydrochloride) |
| | | 2-(2-(hydroxymethyl)-1-methylpiperidinium-1-yl)acetate |
| | | Alanyl-glutamine |
| | | β-Alanine |
| | | L-Arginine monohydrochloride |
| 1020 | 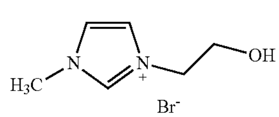 | 3-(2-hydroxyethyl)-1-methyl-1H-imidazol-3-ium bromide |
| 1017 | 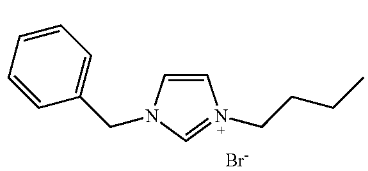 | 1-benzyl-3-butyl-1H-imidazol-3-ium bromide |

In some embodiments, the zwitterionic stabilizer is selected from among 3-((2-hydroxyethyl)dimethylammonio)propanoate, 3-(4-hydroxy-1-methylpiperidinium-1-yl)propanoate, and 2-((2-hydroxypropyl)dimethylammonio) acetate, 3-((2,3-dihydroxypropyl)dimethylammonio) propanoate, 3-((3-hydroxypropyl)dimethylammonio) propanoate, and 2-(2-(hydroxymethyl)-1-methylpiperidinium-1-yl)acetate. In some embodiments, the storage stabilizer is selected from among Alanyl-glutamine, β-Alanine, (S)-2-carboxy-1,1-dimethylpyrrolidinium chloride (Proline Betaine Hydrochloride), and L-Arginine monohydrochloride. In some embodiments, the zwitterionic stabilizer is Alanyl-glutamine.

In some embodiments, the cationic ester stabilizer is selected from among 4-(2-ethoxy-2-oxoethyl)-4-methyl-morpholin-4-ium bromide, 1-(2-ethoxy-2-oxoethyl)-1-methylpiperidinium bromide, 1-(2-ethoxy-2-oxoethyl)-1-methylpyrrolidinium bromide, 1-(2-ethoxy-2-oxoethyl)-3-hydroxy-1-methylpiperidinium bromide, N-(2-cyanoethyl)-2-ethoxy-N,N-dimethyl-2-oxoethanaminium bromide, ethoxy-N,N-diethyl-N-methyl-2-oxoethanaminium bromide, N-(2-ethoxy-2-oxoethyl)-N,N-dimethylcyclohexanaminium bromide, 2-ethoxy-N-(2-(2-hydroxyethoxy) ethyl)-N,N-dimethyl-2-oxoethanaminium bromide, 1-(2-ethoxy-2-oxoethyl)-3-hydroxy-1-methylpiperidium bromide.

In some embodiments, the storage stabilizing agent is an imidazolium compound. In some embodiments, the imidazolium compound is 3-(2-hydroxyethyl)-1-methyl-1H-imidazol-3-ium bromide or 1-benzyl-3-butyl-1H-imidazol-3-ium bromide.

In some embodiments, the zwitterionic stabilizer is an amino acid derivative. In some embodiments, the amino acid derivative is not arginine, arginine/glutamic acid, or polyglutamic acid. In some embodiments, the zwitterionic stabilizer is a dipeptide. In some embodiments, the dipeptide is alanyl-glutamine. In some embodiments, the zwitterionic stabilizer is β-Alanine. In some embodiments, the zwitterionic stabilizer is (S)-2-carboxy-1,1-dimethylpyrrolidinium chloride (Proline Betaine Hydrochloride).

Exemplary methods for the synthesis of the polymerase storage stabilizing agents provided herein are provided elsewhere herein.

In some embodiments, the compositions provided herein comprise about 1 mM to about 10M of the zwitterionic stabilizing agent. In some embodiments, the compositions provided herein comprise about 10 mM to about 5M of the zwitterionic stabilizing agent. In some embodiments, the compositions provided herein comprise about 100 mM to about 1.25M of the zwitterionic stabilizing agent.

In some embodiments, the compositions provided herein comprise about 0.1 mg/ml to about 100 mg/ml of the cationic ester stabilizing agent. In some embodiments, the compositions provided herein comprise about 0.5 mg/ml to about 50 mg/ml of the cationic ester stabilizing agent. In some embodiments, the compositions provided herein comprise about 1 mg/ml to about 25 of the cationic ester stabilizing agent.

In some embodiments, the compositions provided herein comprise about 0.01 mM to about 2M of an ionic imidazolium stabilizing agent.

In some embodiments, the compositions provided herein comprise two or more zwitterionic polymerase storage stabilizing agents. In some embodiments, the compositions provided herein comprise two or more cationic ester polymerase storage stabilizing agents. In some embodiments, the compositions provided herein comprise a zwitterionic polymerase storage stabilizing agents and a cationic ester polymerase storage stabilizing agent. In some embodiments, the compositions provided herein comprise a zwitterionic stabilizing agent disclosed herein and one or more additional polymerase storage stabilizing agents. In some embodiments, the compositions provided herein comprise a cationic stabilizing agent disclosed herein and one or more additional polymerase storage stabilizing agents. In some embodiments, the additional stabilizing agent is an additional anionic or zwitterionic stabilizing agent. In some embodiments, the additional stabilizing agent is an additional cationic storage stabilizing agent. Exemplary zwitterionic and cationic ester stabilizing agents are disclosed elsewhere herein. Additional exemplary stabilizing agents are disclosed elsewhere herein and include, for example, hydroxyectoine.

In some embodiments, the compositions provided herein comprise a zwitterionic stabilizing agent disclosed herein and one or more additional polymerase stabilizing agents that stabilize the polymerase during the practice of a method, such as nucleic acid amplification or nucleic acid sequencing. In some embodiments, the compositions provided herein comprise a zwitterionic stabilizing agent disclosed herein and one or more additional polymerase stabilizing agents that stabilize the polymerase during practice of one or more steps of a method, such as nucleic acid amplification or nucleic acid sequencing. In some embodiments, the compositions provided herein comprise a cationic ester stabilizing agent disclosed herein and one or more additional polymerase stabilizing agents that stabilize the polymerase during practice of one or more steps of a method, such as nucleic acid amplification or nucleic acid sequencing. Exemplary PCR stabilizing agents are known in the art and include, but are not limited to non-ionic detergents, nucleic acids (e.g. oligonucleotides, aptamers), inert proteins (e.g., bovine serum albumin (BSA) or fragments and derivatives thereof), antibodies that bind to one or more polymerases of the composition, polyvinyl pyrrolidone, and polyethylene glycol (PEG). In a particular embodiment, the composition comprises an antibody (e.g. a monoclonal antibody) that inhibits polymerase activity (e.g. Taq polymerase activity), where the antibody is inactivated during at least one step of a nucleic acid amplification protocol (see e.g. Mizuguchi et al. *J Biochem.* 126: 762-8 (1999)).

In some embodiments, the composition for stabilization of a polymerase comprises a polysaccharide. In some embodiments, the composition for stabilization of a polymerase comprises two or more polysaccharides. In some embodiments, the composition comprises about 0.05%-20% polysaccharides. In some embodiments, the composition comprises about 0.6-10% polysaccharides. In some embodiments, the composition comprises about 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20% polysaccharides. In some embodiments, the composition for stabilization of a polymerase comprises a disaccharide. In some embodiments, the composition for stabilization of a polymerase comprises a trisaccharide. In some embodiments, the composition for stabilization of a polymerase comprises a disaccharide and a trisaccharide.

In some embodiments, the composition for stabilization of a polymerase comprises a trisaccharide. In some embodiments, the trisaccharide is selected from among melezitose, raffinose and maltotriose. In particular embodiments, the trisaccharide is melezitose. In some embodiments, the composition comprises about 0.05%-20% melezitose. In some embodiments, the composition comprises about 0.6-10% melezitose. In some embodiments, the composition comprises about 0.5%-20% melezitose. In some embodiments, the composition comprises about 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20% melezitose. In some embodiments, the composition comprises 6% melezitose. In some embodiments, the composition comprises 1.88% melezitose. In some embodiments, the composition comprises 0.6% melezitose.

In some embodiments, the composition for stabilization of a polymerase comprises a disaccharide. In some embodiments, the disaccharide is sucrose (α-D-glucopyranosyl-(1→2)-β-D-fructofuranoside) or trehalose (α-D-glucopyranosyl-(1→1)-α-D-glucopyranoside). In particular embodiments, the composition comprises sucrose. In some embodiments, the composition does not comprise trehalose. In some embodiments, the composition comprises about 0.1%-25% sucrose. In some embodiments, the composition comprises about 1%-25% sucrose. In some embodiments, the composition comprises about 0.5%-20% sucrose. In some embodiments, the composition comprises about 0.6-10% sucrose. In some embodiments, the composition comprises about 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% sucrose. In some embodiments, the composition comprises 10% sucrose. In some embodiments, the composition comprises 3.13% sucrose.

In some embodiments, the composition for stabilization of a polymerase comprises a polymer. In some embodiments, the polymer is polyvinyl alcohol (PVA), polyethylene glycol (PEG), and polyvinylpyrrolidone. In some embodiments, the composition for stabilization of a polymerase comprises polyvinyl alcohol (PVA). In some embodiments, the composition comprises about 0.05%-5% PVA. In some embodiments, the composition comprises about 0.1%-1% PVA. In some embodiments, the composition comprises about 0.1%, 0.2%, 0.3%, 0.4%, 0.5%, 0.6%, 0.7%, 0.8%, 0.9%, 1%, 2%, 3%, 4%, or 5% PVA. In some embodiments, the composition comprises 0.313% PVA. In some embodiments, the composition comprises 1% PVA. In some embodiments, the composition comprises 2% PVA.

In some embodiments, the composition for stabilization of a polymerase comprises a pH buffer. In some embodiments, the pH buffer is selected from among Tris, citrate, acetate, phosphate, borate, CAPS, CAPSO, HEPES, MES, MOPS, MOPSO, PIPES, carbonate, and bicarbonate. In particular embodiments, the buffer is a Tris buffer.

In some embodiments, the storage stabilizing agent is provided as a formulation comprising a polysaccharide, a polymer; and a zwitterionic compound, wherein the zwitterionic compound does not contain sulfate. In some embodiments, the zwitterionic compound is not a surfactant or a detergent.

In some embodiments, the storage stabilizing agent is provided as a formulation comprising a disaccharide, a trisaccharide, a polymer; and a zwitterionic compound, wherein the zwitterionic compound does not contain a sulfate group. In some embodiments, the zwitterionic compound is not a surfactant or a detergent. In some embodiments, the disaccharide is sucrose. In some embodiments, the trisaccharide is melezitose. In some embodiments, the polymer is PVA.

In some embodiments, the storage stabilizing agent is provided as a formulation comprising sucrose, melezitose, PVA, and a zwitterionic compound, wherein the zwitterionic compound does not contain a sulfate group. In some embodiments, the zwitterionic compound is not a surfactant or a detergent.

In some embodiments, the storage stabilizing agent is provided as a formulation comprising a polysaccharide, a polymer; and a cationic ester.

In some embodiments, the storage stabilizing agent is provided as a formulation comprising a disaccharide, a trisaccharide, a polymer; and a cationic ester. In some embodiments, the disaccharide is sucrose. In some embodiments, the trisaccharide is melezitose. In some embodiments, the polymer is PVA.

In some embodiments, the storage stabilizing agent is provided as a formulation comprising sucrose, melezitose, PVA, and a cationic ester. In some embodiments, the formulation comprises BSA. In some embodiments, does not comprise BSA.

In some embodiments, the storage stabilizing agent is provided as a formulation listed in Table 2. In some embodiments, the storage stabilizing agent is provided as a formulation listed in Table 3.

In some embodiments, the storage stabilizing agent is provided as a formulation comprising a dipeptide.

In some embodiments, the storage stabilizing agent is provided as a formulation comprising Alanyl-Glutamine.

In some embodiments, the storage stabilizing agent is provided as a formulation comprising about 500 mM-5M Alanyl-Glutamine.

In some embodiments, the storage stabilizing agent is provided as a formulation comprising 625 mM Alanyl-Glutamine.

In some embodiments, the storage stabilizing agent is provided as a formulation comprising 1.25 M Alanyl-Glutamine.

In some embodiments, the storage stabilizing agent is provided as a formulation comprising 10% Sucrose, 6% Melezitose, 1% PVA (MW~30-70,000 and 87-90% hydrolyzed); and 250 mM Alanyl-Glutamine.

In some embodiments, the storage stabilizing agent is provided as a formulation comprising 10% Sucrose, 6% Melezitose, 0.313% PVA (MW~30-70,000 and 87-90% hydrolyzed); and 625 mM Alanyl-Glutamine.

In some embodiments, the storage stabilizing agent is provided as a formulation comprising 10% Sucrose, 1% PVA (MW~30-70,000 and 87-90% hydrolyzed); and 25 mg/mL 2-Ethoxy-N-(2-(2-hydroxyethoxy)ethyl)-N,N-dimethyl-2-oxoethanaminium bromide.

In some embodiments, the storage stabilizing agent is provided as a formulation comprising 10% Sucrose, 6% Melezitose, 1% PVA (MW~30-70,000 and 87-90% hydrolyzed); 62.5 mM Alanyl-Glutamine; and 25 mg/mL 2-Ethoxy-N-(2-(2-hydroxyethoxy)ethyl)-N,N-dimethyl-2-oxoethanaminium bromide.

In some embodiments, the storage stabilizing agent is provided as a formulation comprising 10% Sucrose, 6% Melezitose, 1% PVA (MW~30-70,000 and 87-90% hydrolyzed); 250 mM Alanyl-Glutamine; and 25 mg/mL 2-Ethoxy-N-(2-(2-hydroxyethoxy)ethyl)-N,N-dimethyl-2-oxoethanaminium bromide.

In some embodiments, the storage stabilizing agent is provided as a formulation comprising 3.13% Sucrose, 1.88% Melezitose, 313% PVA (MW~30-70,000 and 87-90% hydrolyzed); and 12.5 mg/mL 2-Ethoxy-N-(2-(2-hydroxyethoxy)ethyl)-N,N-dimethyl-2-oxoethanaminium bromide.

In some embodiments, the storage stabilizing agent is provided as a formulation comprising 3.13% Sucrose, 1.88% Melezitose, 313% PVA (MW~30-70,000 and 87-90% hydrolyzed); 625 mM Alanyl-Glutamine; and 12.5 mg/mL 2-Ethoxy-N-(2-(2-hydroxyethoxyl)ethyl)-N,N-dimethyl-2-oxoethanaminium bromide.

In some embodiments, the storage stabilizing agent is provided as a formulation comprising 10% Sucrose, 6% Melezitose, 1% PVA (MW~30-70,000 and 87-90% hydrolyzed); and 100 mM Proline Betaine.

In some embodiments, the storage stabilizing agent is provided as a formulation comprising 1% Sucrose, 0.6% Melezitose, 0.1% PVA (MW~30-70,000 and 87-90% hydrolyzed); 100 mM Alanyl-Glutamine; and 2.5 mg/mL 2-Ethoxy-N-(2-(2-hydroxyethoxyl)ethyl)-N,N-dimethyl-2-oxoethanaminium bromide.

In some embodiments, the storage stabilizing agent is provided as a formulation comprising 1% Sucrose, 0.6% Melezitose, 0.1% PVA (MW~30-70,000 and 87-90% hydrolyzed); 500 mM Alanyl-Glutamine; and 2.5 mg/mL 2-Ethoxy-N-(2-(2-hydroxyethoxyl)ethyl)-N,N-dimethyl-2-oxoethanaminium bromide.

In some embodiments, the storage stabilizing agent is provided as a formulation comprising 1% Sucrose, 0.6% Melezitose, 0.1% PVA (MW~30-70,000 and 87-90% hydrolyzed); 1M Alanyl-Glutamine; and 2.5 mg/mL 2-Ethoxy-N-(2-(2-hydroxyethoxyl)ethyl)-N,N-dimethyl-2-oxoethanaminium bromide.

In some embodiments, the storage stabilizing agent is provided as a formulation comprising 10% Sucrose, 6% Melezitose, 1% PVA (MW~30-70,000 and 87-90% hydrolyzed); and 25 mg/mL 2-Ethoxy-N-(2-(2-hydroxyethoxyl)ethyl)-N,N-dimethyl-2-oxoethanaminium bromide.

In some embodiments, the storage stabilizing agent is provided as a formulation comprising 10% Sucrose, 6% Melezitose, 1% PVA (MW~30-70,000 and 87-90% hydrolyzed); and 25 mg/mL 2-Ethoxy-N-(2-(2-hydroxyethoxyl)ethyl)-N,N-dimethyl-2-oxoethanaminium bromide.

In some embodiments, the storage stabilizing agent is provided as a formulation comprising 10% Sucrose, 6% Melezitose, 1% PVA (MW~30-70,000 and 87-90% hydrolyzed); 0.5 mg/mL BSA; and 25 mg/mL 2-Ethoxy-N-(2-(2-hydroxyethoxyl)ethyl)-N,N-dimethyl-2-oxoethanaminium bromide.

In some embodiments, the storage stabilizing agent is provided as a formulation comprising 10% Sucrose, 6% Melezitose, 1% PVA (MW~30-70,000 and 87-90% hydrolyzed); 1 mg/mL BSA; and 25 mg/mL 2-Ethoxy-N-(2-(2-hydroxyethoxyl)ethyl)-N,N-dimethyl-2-oxoethanaminium bromide.

In some embodiments, the storage stabilizing agent is provided as a formulation comprising 10% Sucrose; 6% Melezitose; 1% PVA (MW~30-70,000 and 87-90% hydrolyzed); and 25 mg/mL 3-((2-hydroxyethyl)dimethylammonio)propanoate.

In some embodiments, the storage stabilizing agent is provided as a formulation comprising 10% Sucrose; 6% Melezitose; 1% PVA (MW~30-70,000 and 87-90% hydrolyzed); and 25 mg/mL 3-(4-hydroxy-1-methylpiperidinium-1-yl)propanoate.

In some embodiments, the storage stabilizing agent is provided as a formulation comprising 10% Sucrose; 6% Melezitose, 2% PVA (MW~30-70,000 and 87-90% hydrolyzed); and 25 mg/mL 2-((2-hydroxypropyl)dimethylammonio)acetate.

In some embodiments, the storage stabilizing agent is provided as a formulation comprising 10% Sucrose, 6% Melezitose, 1% PVA (MW~30-70,000 and 87-90% hydrolyzed), 50 mM Tris pH 8, 25 mg/mL N,N-Dimethyl-N-(2-hydroxyethyl)-3-ammonium-propionate.

In some embodiments, the storage stabilizing agent is provided as a formulation comprising 10% Sucrose, 6% Melezitose, 1% PVA (MW~30-70,000 and 87-90% hydrolyzed), 25 mg/mL 1-methyl-4-hydroxypiperidinium-3-propionate.

In some embodiments, the storage stabilizing agent is provided as a formulation comprising 10% Sucrose, 6% Melezitose, 2% PVA (MW~30-70,000 and 87-90% hydrolyzed), 25 mg/mL N-(2-ethoxy-2-oxoethyl)-2-hydroxy-N,N-dimethylpropan-1-aminium bromide.

In some embodiments, the storage stabilizing agent is provided as a formulation comprising 6.7% Sucrose, 4% Melezitose, 0.8% PVA (MW~30-70,000 and 99% hydrolyzed), 50 mM 3-(4-hydroxy-1-methylpiperidinium-1-yl)propanoate.

In some embodiments, the storage stabilizing agent is provided as a formulation comprising 6.7% Sucrose, 4% Melezitose, 0.8% PVA (MW~30-70,000 and 99% hydrolyzed), 45 mM Tris pH 8, 100 mM 3-(1-methylpyrrolidinium-1-yl)propanoate.

In some embodiments, the storage stabilizing agent is provided as a formulation comprising 6.7% Sucrose, 4% Melezitose, 0.8% PVA (MW~30-70,000 and 99% hydrolyzed), 45 mM Tris pH 8, 100 mM N,N-dimethyl-N-(2-hydroxyethyl)-3-ammonium propionate.

In some embodiments, the storage stabilizing agent is provided as a formulation comprising 6.7% Sucrose, 4% Melezitose, 0.8% PVA (MW~30-70,000 and 99% hydrolyzed), 45 mM Tris pH 8, 50 mM 3-((2,3-dihydroxypropyl)dimethylammonio)propanoate.

In some embodiments, the storage stabilizing agent is provided as a formulation comprising 6.7% Sucrose, 4% Melezitose, 0.8% PVA (MW~30-70,000 and 99% hydrolyzed), 45 mM Tris pH 8, 50 mM 3-((2-hydroxypropyl)dimethylammonio)propanoate.

In some embodiments, the storage stabilizing agent is provided as a formulation comprising 6.7% Sucrose, 4% Melezitose, 0.8% PVA (MW~30-70,000 and 99% hydrolyzed), 45 mM Tris pH 8, 50 mM 3-((3-hydroxypropyl)dimethylammonio)propanoate.

In some embodiments, the storage stabilizing agent is provided as a formulation comprising 6.7% Sucrose, 4% Melezitose, 0.8% PVA (MW~30-70,000 and 99% hydrolyzed), 45 mM Tris pH 8, 50 mM 1-(2-ethoxy-2-oxoethyl)-1-methylpiperidinium bromide.

In some embodiments, the storage stabilizing agent is provided as a formulation comprising 6.7% Sucrose, 4% Melezitose, 0.8% PVA (MW~30-70,000 and 99% hydrolyzed), 45 mM Tris pH 8, 50 mM 2-(cyclohexyldimethylammonio)acetate.

In some embodiments, the storage stabilizing agent is provided as a formulation comprising 6.7% Sucrose, 4% Melezitose, 0.8% PVA (MW~30-70,000 and 99% hydrolyzed), 45 mM Tris pH 8, 50 mM 1-ethoxy-N-(2-(2-hydroxyethoxyl)ethyl)-N,N-dimethyl-2-oxoethanaminium bromide.

In some embodiments, the storage stabilizing agent is provided as a formulation comprising 6.7% Sucrose, 4% Melezitose, 0.8% PVA (MW~30-70,000 and 99% hydrolyzed), 45 mM Tris pH 8, 50 mM 4-(2-ethoxy-2-oxoethyl)-4-methylmorpholin-4-ium bromide.

In some embodiments, the storage stabilizing agent is provided as a formulation comprising 6.7% Sucrose, 4% Melezitose, 0.8% PVA (MW~30-70,000 and 99% hydrolyzed), 45 mM Tris pH 8, 50 mM 1-(2-ethoxy-2-oxoethyl)-1-methylpyrrolidinium bromide.

In some embodiments, the storage stabilizing agent is provided as a formulation comprising 6.7% Sucrose, 4% Melezitose, 0.8% PVA (MW~30-70,000 and 99% hydrolyzed), 45 mM Tris pH 8, 50 mM 1-(2-ethoxy-2-oxoethyl)-3-hydroxy-1-methylpiperidinium bromide.

In some embodiments, the storage stabilizing agent is provided as a formulation comprising 6.7% Sucrose, 4% Melezitose, 0.8% PVA (MW~30-70,000 and 99% hydrolyzed), 45 mM Tris pH 8, 50 mM N-(2-cyanoethyl)-2-ethoxy-N,N-dimethyl-2-oxoethanaminium bromide.

In some embodiments, the storage stabilizing agent is provided as a formulation comprising 10% Sucrose, 6% Melezitose, 1% PVA (MW~30-70,000 and 87-90% hydrolyzed), 50 mM Tris pH 8, 2.5 mg/mL 3-(4-methylmorpholino-4-ium)propane-1-sulfonate.

In some embodiments, the storage stabilizing agent is provided as a formulation comprising 10% Sucrose, 6% Melezitose, 1% PVA (MW~30-70,000 and 87-90% hydrolyzed), 50 mM Tris pH 8, 2.5 mg/mL 1-methyl-4-hydroxypiperidinium-3-propionate.

In some embodiments, the storage stabilizing agent is provided as a formulation comprising 10% Sucrose, 6% Melezitose, 2% PVA (MW~30-70,000 and 87-90% hydrolyzed), 100 mM Tris pH 8, 2.5 mg/mL N-(2-ethoxy-2-oxoethyl)-2-hydroxy-N,N-dimethylpropan-1-aminium bromide.

In some embodiments, the storage stabilizing agent is provided as a formulation comprising 50 mM hydroxyectoine, 10 mM boric acid, 1 mM sodium tetraborate, pH 8.

In some embodiments, the storage stabilizing agent is provided as a formulation comprising 50 mM hydroxyectoine, 10 mM Tris pH 7.5, 1% PVA (MW~30-70,000 and 99% hydrolyzed).

In some embodiments, the storage stabilizing agent is provided as a formulation comprising 50 mM hydroxyectoine, 10 mM Tris pH 7.5.

TABLE 2

Exemplary Storage Formulations

| Class ID | Polysaccharides 0.6-10% w/v | Zwitterions 0-2M | Polymer 0.1-1% w/v | pH 6.8-8.2 | cationic ester 1-25 mg/ml | ionic imidazolium compound 0.01-2M | Albumin 0-1 mg/ml |
|---|---|---|---|---|---|---|---|
| SM-0001009 | Sucrose, Melezitose | | PVA | 8 | 2-Ethoxy-N-(2-(2-hydroxyethoxy)ethyl)-N,N-dimethyl-2-oxoethanaminium bromide | | |
| SM-0001006 | Sucrose, Melezitose | | PVA | 8 | 2-Ethoxy-N-(2-(2-hydroxyethoxy)ethyl)-N,N-dimethyl-2-oxoethanaminium bromide | | BSA |
| SM-0001010 | Sucrose, Melezitose | Alanyl-Glutamine | PVA | 8 | 2-Ethoxy-N-(2-(2-hydroxyethoxy)ethyl)-N,N-dimethyl-2-oxoethanaminium bromide | | BSA |
| SM-0001007 | | Alanyl-Glutamine | | 8 | | | |
| SM-0001008 | | Alanyl-Glutamine | | 8 | | | BSA |
| SM-0001017 | | | | 8 | | 1-benzyl-3-butyl-1H-imidazol-3-ium bromide | |
| SM-0001020 | | | | 8 | | 3-(2-hydroxyethyl)-1-methyl-1H-imidazol-3-ium bromide | |
| SM-0001024 | Sucrose, Melezitose | | PVA | 8 | 25 mg/mL 2-Ethoxy-N-(2-(2-hydroxyethoxy)ethyl)-N,N-dimethyl-2-oxoethanaminium bromide | 1-benzyl-3-butyl-1H-imidazol-3-ium bromide | |
| SM-0001026 | Sucrose, Melezitose | | PVA | 8 | 25 mg/mL 2-Ethoxy-N-(2-(2-hydroxyethoxy)ethyl)-N,N-dimethyl-2-oxoethanaminium bromide | 3-(2-hydroxyethyl)-1-methyl-1H-imidazol-3-ium bromide | |

TABLE 3

Additional Exemplary Storage Formulations

| Formulation | Components |
|---|---|
| 36 | Sucrose, Melezitose, PVA, N,N-Dimethyl-N-(2-hydroxyethyl)-3-ammonium-propionate |
| 150 | Sucrose, Melezitose, PVA, 1-methyl-4-hydroxypiperidinium-3-propionate |
| 199 | Sucrose, Melezitose, PVA, N-(2-ethoxy-2-oxoethyl)-2-hydroxy-N,N-dimethylpropan-1-aminium bromide |
| c-102 | Sucrose, Melezitose, PVA, 3-(4-hydroxy-1-methylpiperidinium-1-yl)propanoate |
| c-108 | Sucrose, Melezitose, PVA, 3-(1-methylpyrrolidinium-1-yl)propanoate |
| c-111 | Sucrose, Melezitose, PVA, N,N-dimethyl-N-(2-hydroxyethyl)-3-ammonium propionate |
| c-116 | Sucrose, Melezitose, PVA, 3-((2,3-dihydroxypropyl)dimethylammonio)propanoate |

TABLE 3-continued

Additional Exemplary Storage Formulations

| Formulation | Components |
| --- | --- |
| c-127 | Sucrose, Melezitose, PVA, 3-((2-hydroxypropyl)dimethylammonio)propanoate |
| c-136i | Sucrose, Melezitose, PVA, 1-(2-ethoxy-2-oxoethyl)-1-methylpiperidinium bromide |
| c-146i | Sucrose, Melezitose, PVA, 2-(cyclohexyldimethylammonio)acetate |
| c-147i | Sucrose, Melezitose, PVA, 1-ethoxy-N-(2-(2-hydroxyethoxy)ethyl)-N,N-dimethyl-2-oxoethanaminium bromide |
| c-135i | Sucrose, Melezitose, PVA, 4-(2-ethoxy-2-oxoethyl)-4-methylmorpholin-4-ium bromide |
| c-137i | Sucrose, Melezitose, PVA, 1-(2-ethoxy-2-oxoethyl)-1-methylpyrrolidinium bromide |
| c-138i | Sucrose, Melezitose, PVA, 1-(2-ethoxy-2-oxoethyl)-3-hydroxy-1-methylpiperidinium bromide |
| c-142i | Sucrose, Melezitose, PVA, N-(2-cyanoethyl)-2-ethoxy-N,N-dimethyl-2-oxoethanaminium bromide |
| c-144i | Sucrose, Melezitose, PVA, 2-ethoxy-N,N-diethyl-N-methyl-2-oxoethanaminium bromide |
| 129 | Sucrose, Melezitose, PVA, 3-(4-methylmorpholino-4-ium)propane-1-sulfonate |
| 150 | Sucrose, Melezitose, PVA, 1-methyl-4-hydroxypiperidinium-3-propionate |
| 199 | Sucrose, Melezitose, PVA, N-(2-ethoxy-2-oxoethyl)-2-hydroxy-N,N-dimethylpropan-1-aminium bromide |

In some embodiments, the compositions provided herein for stabilization of a polymerase are diluted, such as, for example, at a ratio of 10:1, 9:1, 8:1, 7:1, 6:1, 5:1, 4:1, 3:1, 2:1, 1:1, 1:2, 1:3, 1:4, 1:5, 1:6, 1:7, 1:8, 1:9 or 1:10 in an appropriate buffer prior to the addition of a polymerase. In some embodiments, the compositions provided herein for stabilization of a polymerase are added to a composition comprising a polymerase, for example, at a ratio of 10:1, 9:1, 8:1, 7:1, 6:1, 5:1, 4:1, 3:1, 2:1, 1:1, 1:2, 1:3, 1:4, 1:5, 1:6, 1:7, 1:8, 1:9 or 1:10 of the stabilizing composition to the polymerase composition. In some embodiments, selection of a particular ratio is determined empirically by the skilled artisan.

In some embodiments, the compositions provided herein containing a storage stabilizing agent provided herein increase the half-life of a polymerase at room temperature as compared to a composition without the storage stabilizing agent. In some embodiments, the half-life is increased by 5%, 10%, 20%, 30%, 40%, 50%, 60%, 70%, 80%, 90%, 100%, 200%, 300%, 400%, 500%, 1000% or longer. In some embodiments, the compositions provided herein containing a storage stabilizing agent provided herein doubles the half-life of a polymerase at room temperature as compared to a composition without the storage stabilizing agent.

In some embodiments, the compositions provided herein containing a storage stabilizing agent provided herein increase the half-life of a polymerase at 45° C. as compared to a composition without the storage stabilizing agent. In some embodiments, the half-life is increased by 5%, 10%, 20%, 30%, 40%, 50%, 60%, 70%, 80%, 90%, 100%, 200%, 300%, 400%, 500%, 1000% or longer. In some embodiments, the compositions provided herein containing a storage stabilizing agent provided herein doubles the half-life of a polymerase at 45° C. as compared to a composition without the storage stabilizing agent.

In some embodiments, the compositions provided herein comprising a polymerase and a stabilizing agent disclosed herein are stable for at least 4 weeks, at least 1 month, at least 2 months, at least 3 months, at least 4 months, at least 5 months, at least 6 months, at least 7 months, at least 8 months, at least 9 months, at least 10 months, at least 11 months, at least 1 year, at least 1.5 years, at least 2 years, at least 3 years, at least 4 years, at least 5 years, or longer.

In some embodiments, the stabilized polymerase of the compositions provided herein retains at least 70%, at least 75%, at least 80%, at least 85%, at least 90%, at least 95% or more of its activity after a prescribed storage period and temperature compared to its original activity prior to storage. In some embodiments, the stabilized polymerase of the compositions provided herein retains at least 70%, at least 75%, at least 80%, at least 85%, at least 90%, at least 95% or more of its activity after at least 4 weeks, at least 1 month, at least 2 months, at least 3 months, at least 4 months, at least 5 months, at least 6 months, at least 7 months, at least 8 months, at least 9 months, at least 10 months, at least 11 months, at least 1 year, at least 1.5 years, at least 2 years, at least 3 years or longer storage.

In particular embodiments, the stabilized polymerase of the compositions provided herein retains at least 70%, at least 75%, at least 80%, at least 85%, at least 90%, at least 95% or more of its activity after 3 weeks storage at room temperature compared to its original activity prior to storage. In some embodiments, the stabilized polymerase of the compositions provided herein retains at least 70%, at least 75%, at least 80%, at least 85%, at least 90%, at least 95% or more of its activity after 6 weeks storage at room temperature compared to its original activity prior to storage.

In particular embodiments, the stabilized polymerase of the compositions provided herein retains at least 70%, at least 75%, at least 80%, at least 85%, at least 90%, at least 95% or more of its activity after 3 weeks storage at about 45° C. compared to its original activity prior to storage. In some embodiments, the stabilized polymerase of the compositions provided herein retains at least 70%, at least 75%, at least 80%, at least 85%, at least 90%, at least 95% or more of its activity after 6 weeks storage at about 45° C. compared to its original activity prior to storage.

In some embodiments, the polymerase used in the compositions and methods provided herein is a DNA polymerase. In some embodiments, the polymerase used in the compositions and methods provided herein is a reverse transcriptase. In some embodiments, the polymerase used in the compositions and methods provided herein is an RNA polymerase. In some embodiments, the polymerase is for use in nucleic acid amplification. In some embodiments, the polymerase is for use in polymerase chain reaction (PCR). In some embodiments, the polymerase is for use in Reverse transcriptase polymerase chain reaction (RT-PCR). In some embodiments, the polymerase is for use in linear amplification. In some embodiments, the polymerase is for use in quantitative polymerase chain reaction (qPCR).

Exemplary DNA polymerases for use in the compositions and methods provided herein include, but are not limited to, *Thermus thermophilus* (Tth) DNA polymerase, *Thermus aquaticus* (Taq) DNA polymerase, *Thermotoga neopalitana* (Tne) DNA polymerase, *Thermotoga maritima* (Tma) DNA polymerase, *Thermococcus litoralis* (Tli or VENT™) DNA polymerase, *Thermus eggertssonii* (Teg) DNA polymerase, *Pyrococcus furiosus* (Pfu) DNA polymerase, DEEPVENT. DNA polymerase, *Pyrococcus woosii* (Pwo) DNA polymerase, *Pyrococcus* sp KDD2 (KOD) DNA polymerase, *Bacillus* sterothermophilus (Bst) DNA polymerase, *Bacillus caldophilus* (Bea) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME) DNA polymerase, *Methanobacterium thermoautotrophicum* (Mth) DNA polymerase, *mycobacterium* DNA polymerase (Mtb, Mlep), and mutants, variants and derivatives thereof, including enzymes with chemical modifications and hot start polymerases, such as HotStart Taq polymerase (QIAGEN). In some embodiments, the polymerase is Amplitaq. In some embodiments, the polymerase is Amplitaq Gold.

Exemplary RNA polymerases for use in the compositions and methods provided herein include, but are not limited to, RNA polymerases such as T3, T5 and SP6 and mutants, variants and derivatives thereof.

In some embodiments, the nucleic acid polymerases for use in the compositions and methods provided herein are mesophilic or thermophilic (i.e. thermostable). Exemplary mesophilic DNA polymerases for use in the compositions and methods provided herein include, but are not limited to, T7 DNA polymerase, T5 DNA polymerase, Klenow fragment DNA polymerase, DNA polymerase III. Exemplary thermostable DNA polymerases for use in the compositions and methods provided herein include, but are not limited to, Teg, Taq, Tne, Tma, Pfu, Tfl, Tth, Stoffel fragment, VENT. and DEEPVENT DNA polymerases, and mutants, variants and derivatives thereof (see e.g. U.S. Pat. No. 5,436,149; U.S. Pat. No. 4,889,818; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; Barnes, W. M., Gene 112:29-35 (1992); Lawyer, F. C., et al., PCR Meth. Appl. 2:275-287 (1993); Flamm, J.-M, et al., *Nucl. Acids Res.* 22(15):3259-3260 (1994) which are incorporated by reference in their entireties). In some embodiments, for amplification of long nucleic acid molecules (e.g., nucleic acid molecules longer than about 3-5 Kb in length), at least two DNA polymerases (one substantially lacking 3' exonuclease activity and the other having 3' exonuclease activity) are used. See, e.g. U.S. Pat. No. 5,436,149; U.S. Pat. No. 5,512,462; Barnes, W. M., Gene 112:29-35 (1992), and U.S. patent US Pat. Pub. No. 2009-0233283, the disclosures of which are incorporated herein in their entireties. Examples of DNA polymerases substantially lacking in 3' exonuclease activity include, but are not limited to, Taq, Tne$^{exo-}$, Tma$^{exo-}$, Pfu$^{exo-}$, Pwo$^{exo-}$ and Tth DNA polymerases, and mutants, variants and derivatives thereof. In a some embodiments, the polymerase is a Taq polymerase or a derivative thereof. In a some embodiments, the polymerase is not Taq polymerase. In some embodiments, the polymerase for use in the compositions and methods provided herein is a native enzyme. In some embodiments, the polymerase for use in the compositions and methods provided herein is a recombinant protein.

In some embodiments, the polymerase for use in the compositions and methods provided herein is a "hot start" DNA polymerase. "Hot start" refers to the inactivation of a DNA polymerase until the initial denaturation step of PCR cycling. Hot start eliminates spurious amplification products resulting from non-specific priming events during reaction setup and initiation, and increases overall reaction efficiency. Exemplary methods used to inactivate DNA polymerases include, but are not limited to, chemical modification (e.g. anhydrides or formaldehydes), physical modification (e.g. wax beads), aptamer binding, primer sequestration, antibody binding, and the addition of thermolabile blocking groups on dNTPs or primers. In some embodiments, the polymerase for use in the compositions and methods provided herein is FastStart Taq polymerase (Roche Applied Science). In some embodiments, the polymerase for use in the compositions and methods provided herein is GoTaq® polymerase (Promega Corp.). In some embodiments, the polymerase for use in the compositions and methods provided herein is JumpStart™ polymerase (Sigma-Aldrich). In some embodiments, the polymerase for use in the compositions and methods provided herein is HotStarTaq DNA Polymerase (Qiagen).

In some embodiments, the nucleic acid polymerases for use in the compositions and methods provided herein are polypeptides having reverse transcriptase activity. Exemplary reverse transcriptase enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (see e.g. Saiki, R. K., et al., Science 239:487-491 (1988); U.S. Pat. Nos. 4,889,818 and 4,965,188), Tne DNA polymerase (WO 96/10640), Tma DNA polymerase (U.S. Pat. No. 5,374,553) and mutants, variants or derivatives thereof (see, e.g., U.S. Pat. Nos. 5,948,614 and 6,015,668). In some embodiments, the nucleic acid polymerases for use in the compositions and methods provided herein include those that are reduced or substantially reduced in RNase H activity. By an enzyme "substantially reduced in RNase H activity" is meant that the enzyme has less than about 20%, more preferably less than about 15%, 10% or 5%, and most preferably less than about 2%, of the RNase H activity of the corresponding wildtype or RNase$^{H+}$ enzyme such as wild-type Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz, M. L., et al., Nucl. Acids Res. 16:265 (1988) and in Gerard, G. F., et al., FOCUS 14(5):91 (1992), the disclosures of all of which are fully incorporated herein by reference. Exemplary of such polypeptides for use in the compositions and methods provided herein include, but are not limited to, M-MLV H reverse transcriptase, RSV$^{H-}$ reverse transcriptase, AMV$^{H-}$ reverse transcriptase, RAV (Rous-associated virus)$^{H-}$ reverse transcriptase, MAV (myeloblastosis-associated virus)$^{H-}$ reverse transcriptase and HIV if reverse transcriptase. It will be understood by one of ordinary skill, however, that any enzyme capable of producing a DNA molecule from a ribonucleic acid molecule (i.e., having reverse transcriptase activity) that is substantially reduced in RNase H activity can be equivalently used in the compositions, methods and kits of the invention.

In some embodiments, the DNA and RNA polymerases for use in the compositions and methods provided herein are obtained commercially, for example from QIAGEN (Hilden, Germany), Invitrogen, Inc. (Carlsbad, Calif.), New England BioLabs (Beverly, Mass.) or ROCHE Biochemicals. Polypeptides having reverse transcriptase activity for use in the invention may be obtained commercially, for example from QIAGEN (Hilden, Germany), Invitrogen, Inc. (Carlsbad, Calif.), Pharmacia (Piscataway, N.J.), Sigma (Saint Louis, Mo.) or ROCHE (Penzberg, Germany). In some embodiments, the polypeptides having reverse transcriptase activity are isolated from their natural viral or bacterial sources according to standard procedures for isolating and purifying natural proteins that are well-known to one of ordinary skill in the art (see, e.g., Houts, G. E., et al., J. Virol. 29:517 (1979)). In some embodiments, the polypeptides having reverse transcriptase activity are prepared by recombinant DNA techniques that are familiar to one of ordinary skill in the art (see, e.g., Kotewicz, M. L., et al., Nucl. Acids Res. 16:265 (1988); Soltis, D. A., and Skalka, A. M., Proc. Natl. Acad. Sci. USA 85:3372-3376 (1988)).

In some embodiments, the polymerase for use in the compositions and methods provided are at a final concentration in solution in the range of from about 0.1-200 units per milliliter, in the range of from about 0.1-50 units per milliliter, in the range of from about 0.1-40 units per milliliter, in the range of from about 0.1-3.6 units per milliliter, in the range of from about 0.1-34 units per milliliter, in the range of from about 0.1-32 units per milliliter, in the range of from about 0.1-30 units per milliliter, or in the range of from about 0.1-20 units per milliliter, and most preferably at a concentration in the range of from of about 20-40 units per milliliter. Other suitable concentrations of such polymerases suitable for use in the compositions and methods provided will be apparent to one or ordinary skill in the art and can differ in the optimal range for different polymerases.

In some embodiments, the stabilized polymerase compositions provided herein are suitable for use in a method for nucleic acid synthesis such as, but not limited to, nucleic acid sequencing, primer extension assay, DNA amplification, RNA synthesis and reverse transcription of RNA into DNA. In some embodiments, the DNA amplification method is an exponential method, such as a polymerase chain reaction (PCR) method. In some embodiments, the stabilized enzymes composition is used in combination with a PCR techniques such as, but not limited to, quantitative PCR (qPCR), real-time PCR, reverse transcription PCR, allele specific PCR, assembly PCR, asymmetric PCR, dial-out PCR, helicase-dependent amplification, hot start PCR, intersequence-specific PCR (ISSR), inverse PCR, ligation-mediated PCR, methylation-specific PCR (MSP), miniprimer PCR, multiplex ligation-dependent probe amplification (MLPA), multiplex PCR, nested PCR, overlap extension PCR, digital PCR, solid phase PCR, thermal asymmetric interlaced PCR (TAIL-PCR), touchdown PCR (step-down PCR), PAN-AC, universal fast walking, LaNe RAGE (lariat-dependent nested PCR for rapid amplification of genomic DNA ends), SYBR Green, Molecular beacon and TaqMan probes. In some embodiments, the DNA amplification method is a linear method, such as DNA linear amplification (e.g. Linear amplification for deep sequencing (LADS), T7-based Linear Amplification of DNA (TLAD), Single-tube linear DNA amplification (LinDA), Linked Linear Amplification (LLA)).

In some embodiments, nucleic acid amplification methods additionally comprise use of one or more polypeptides having reverse transcriptase activity, such as in methods generally known in the art as one-step (e.g., one-step RT-PCR) or two-step (e.g., two-step RT-PCR) reverse transcriptase-amplification reactions. In some embodiments, for amplification of long nucleic acid molecules (i.e., longer than about 3-5 Kb in length), the composition provided herein comprises a combination of polypeptides having DNA polymerase activity.

In some embodiments, the stabilized polymerase compositions provided herein are suitable for use in a nucleic acid amplification technique, such as a polymerase chain reaction assay. In some embodiments, the compositions provided herein are mixed with one or more reagents suitable for use in a nucleic acid amplification technique, such as a polymerase chain reaction assay.

In some embodiments, the compositions provided herein are ready-to-use compositions for use in nucleic acid amplification. For example, in some embodiments, the compositions provided herein comprise at least one DNA polymerase and a polymerase stabilizing agent disclosed herein, such as, for example, a zwitterionic stabilizer compound or a cationic ester compound disclosed herein, and further comprises at least one deoxynucleoside triphosphate and magnesium salts. In some embodiments, the zwitterionic or cationic stabilizer is a compound of formula (I), (II), (III) or (IV). In some embodiments, the stabilizer is selected from among a zwitterionic or cationic stabilizer listed in Table 1. In some embodiments, the composition comprises two or more sequence specific nucleic acid primers for amplification of a target nucleic acid sequence. In some embodiments, the primers are labeled with a detectable moiety, such as a dye, fluorescent molecule or a radiolabel. In some embodiments, the storage stabilizing agent comprises Alanyl-Glutamine. In some embodiments, the storage stabilizing agent comprises 2-ethoxy-N-(2(2-hydroxyethoxy)ethyl)-N,N-dimethyl-2-oxoethanaminium bromide. In some embodiments, the storage stabilizing agent comprises Alanyl-Glutamine and 2-ethoxy-N-(2(2-hydroxyethoxy)ethyl)-N,N-dimethyl-2-oxoethanaminium bromide.

In some embodiments, the ready-to-use compositions provided herein for amplification of nucleic acid further comprise at least one additional polymerase stabilizing agent for enhancing the stability of the polymerase during the nucleic acid amplification procedure. In some embodiments, the at least one additional polymerase stabilizing agent for enhancing the stability of the polymerase inhibits or reduces the loss of polymerase activity during the nucleic acid amplification procedure. In some embodiments, the at least one additional polymerase stabilizing agent for enhancing the stability of the polymerase is a non-ionic detergent. In some embodiments, the compositions provided herein comprise at least one DNA polymerase and a polymerase stabilizing agent disclosed herein, such as, for example, a zwitterionic or cationic ester stabilizer compound disclosed herein, and further comprise at least one deoxynucleoside triphosphates, magnesium salts, and at least one non-ionic detergent. In some embodiments, the composition comprises one non-ionic detergent. In some embodiments, the composition comprises two or more non-ionic detergents. In some embodiments, the non-ionic detergent in the compositions provided herein is selected those that have a molecular weight in the range of approximately 100 to 250,000, such as about 4,000 to 200,000 daltons and stabilize the enzyme at a pH of from about 3.5 to about 9.5, such as from about 4 to 8.5. Examples of such detergents include those specified on pages 295-298 of McCutcheon's Emulsifiers & Detergents, North American edition (1983), published by the McCutcheon Division of MC Publishing Co., 175 Rock Road, Glen Rock, N.J. (USA), the entire disclosure of which is incorporated herein by reference. In some embodiments, the detergents are selected from the group comprising ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers. In some embodiments, the detergent is Tween 20, from ICI Americas Inc., Wilmington, Del., which is a polyoxyethylated (20) sorbitan monolaurate, and Iconol™ NP-40, from BASF Wyandotte Corp. Parsippany, N.J., which is an ethoxylated alkyl phenol (nonyl).

In some embodiments, the composition comprises one or more additional buffers suitable for performance of a nucleic acid amplification assay. In some embodiments, the composition comprises one or more additional buffers, cofactors, and other agents suitable for use in nucleic acid amplification. Selection of such additional agents useful for nucleic acid amplification is within the knowledge of the skilled artisan. Addition of such agents should not negatively, or only minimally, affect the stabilization of the polymerase by the stabilizing agent provided herein. In some embodiments, the composition further comprises glycerol, polyoxylethylated sorbitan monolaurate, ethoxylated nonyl phenol and/or gelatin.

In some embodiments, the composition comprises one or more sequence specific primers. In some embodiments the primers are labeled. In some embodiments, the primers are labeled with a detectable moiety, such as a radioactive moiety, a fluorescent moiety, or a dye molecule. In some embodiments, the composition comprises a dual labeled fluorescence energy transfer (FRET) probe.

In some embodiments, amplification methods comprise one or more steps and may be conducted at a single temperature as an isothermal amplification reaction or at various temperatures such as the polymerase-chain-reaction.

In an exemplary method, nucleic acid amplification is performed by (a) contacting a nucleic acid template with a PCR composition provided herein comprising a DNA polymerase and a polymerase stabilizing agent disclosed herein, such as, for example, a zwitterionic or cationic ester stabilizer compound disclosed herein, and further comprising at least one deoxynucleoside triphosphate, magnesium salts and at least one nonionic detergent; and (b) incubating the mixture under conditions sufficient to amplify a nucleic acid molecule complementary to all or a portion of the template. Nucleic acid molecules amplified by such methods also are provided. In some embodiment, the mixture is subjected to one or more cycles of nucleic acid amplification according to known protocols.

For nucleic acid amplification, including PCR, dNTP salts are added to the reagent compositions. In some embodiments, the sodium or lithium salts of dATP, dCTP, dGTP and dTTP are added to the solution to give a working concentration of each dNTP of about 10-1000 micromolar, such as about 200-300 micromolar, such as about 200 micromolar. For some applications, it may be desirable to also incorporate or substitute dITP or dUTP into the compositions at the same working concentrations.

General methods for amplification and analysis of nucleic acid molecules or fragments are well-known to one of ordinary skill in the art (see, e.g., U.S. Pat. Nos. 4,683,195; 4,683,202; and 4,800,159; Innis, M. A., et al., eds., PCR Protocols: A Guide to Methods and Applications, San Diego, Calif.: Academic Press, Inc. (1990); Griffin, H. G., and Griffin, A. M., eds., PCR Technology: Current Innovations, Boca Raton, Fla.: CRC Press (1994)). For example, amplification methods which can be used in accordance with the provided compositions include PCR (U.S. Pat. Nos. 4,683, 195 and 4,683,202), Strand Displacement Amplification (SDA; U.S. Pat. No. 5,455,166; EP 0 684 315), and Nucleic Acid Sequence-Based Amplification (NASBA; U.S. Pat. No. 5,409,818; EP 0 329 822). In an exemplary protocol, nucleic acid amplification comprises (a) contacting each nucleic acid strand template with four different nucleotide triphosphates and one oligonucleotide primer for each different specific sequence being amplified, wherein each primer is selected to be substantially complementary to different strands of each specific sequence, such that the extension product synthesized from one primer, when it is separated from its complement, can serve as a template for synthesis of the extension product of the other primer, said contacting being at a temperature which promotes hybridization of each primer to its complementary nucleic acid strand; (b) contacting each nucleic acid strand, at the same time as or after step (a), with a DNA polymerase such as from *Thermus aquaticus* which enables combination of the nucleotide triphosphates to form primer extension products complementary to each strand of each nucleic acid; (c) maintaining the mixture from step (b) at an effective temperature for an effective time to promote the activity of the enzyme, and to synthesize, for each different sequence being amplified, an extension product of each primer which is complementary to each nucleic acid strand template, but not so high as to separate each extension product from its complementary strand template; (d) heating the mixture from step (c) for an effective time and at an effective temperature to separate the primer extension products from the templates on which they were synthesized to produce single-stranded molecules, but not so high as to irreversibly denature the enzyme; (e) cooling the mixture from step (d) for an effective time and to an effective temperature to promote hybridization of each primer to each of the single-stranded molecules produced in step (d); and (f) maintaining the mixture from step (e) at an effective temperature for an effective time to promote the activity of the enzyme and to synthesize, for each different sequence being amplified, an extension product of each primer which is complementary to each nucleic acid strand template produced in step (d), but not so high as to separate each extension product from its complementary strand template wherein the effective time and temperatures in steps (e) and (f) may coincide (steps (e) and (f) are carried out simultaneously), or may be separate. Steps (d)-(f) may be repeated until the desired level of sequence amplification is obtained.

Any nucleic acid sequence, in purified or nonpurified form, can be utilized as the starting nucleic acid(s), provided it contains or is suspected to contain the specific nucleic acid sequence desired. Thus, the process may employ, for example, DNA or RNA, including messenger RNA, which DNA or RNA may be single-stranded or double-stranded. In addition, a DNA-RNA hybrid which contains one strand of each may be utilized. A mixture of any of these nucleic acids may also be employed, or the nucleic acids produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid.

It is not necessary that the nucleic acid sequence to be amplified be present initially in a pure form. In some embodiments, the template is a minor fraction of a complex mixture, such as a portion of the β-globin gene contained in whole human DNA (as exemplified in Saiki et al., Science, 230, 1530-1534 (1985)) or a portion of a nucleic acid sequence due to a particular microorganism which organism might constitute only a very minor fraction of a particular biological sample. In some embodiments, the starting nucleic acid sequence contains more than one desired specific nucleic acid sequence which may be the same or different. Therefore, the amplification process is useful not only for producing large amounts of one specific nucleic acid sequence, but also for amplifying simultaneously more than one different specific nucleic acid sequence located on the same or different nucleic acid molecules.

The nucleic acid templates for amplification are obtained from any source, for example, from plasmids such as pBR322, from cloned DNA or RNA, or from natural DNA or RNA from any source, including bacteria, yeast, viruses, organelles, and higher organisms such as plants or animals. In some embodiments, DNA or RNA is extracted from blood, tissue material such as chorionic villi, or amniotic cells by a variety of techniques known in the art.

In some embodiments, where probes are used which are specific to a sequence being amplified and thereafter detected, the cells are directly used without extraction of the nucleic acid if they are suspended in hypotonic buffer and heated to about 90-100° C., until cell lysis and dispersion of intracellular components occur, generally 1 to 15 minutes. After the heating step the amplification reagents may be added directly to the lysed cells.

When it is desired to produce more than one specific nucleic acid sequence from the first nucleic acid or mixture of nucleic acids, the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process.

After the appropriate length of time has passed to produce the desired amount of the specific nucleic acid sequence, the reaction may be halted by inactivating the enzyme in any known manner (e.g., by adding EDTA, phenol, SDS, or CHCl.sub.3) or by separating the components of the reaction.

The amplification process may be conducted continuously. In one embodiment of an automated process, the reaction mixture may be temperature cycled such that the temperature is programmed to be controlled at a certain level for a certain time.

One such instrument for this purpose is the automated machine for handling the amplification reaction of this invention described in now abandoned Ser. No. 833,368 filed Feb. 25, 1986 entitled "Apparatus And Method For Performing Automated Amplification of Nucleic Acid Sequences And Assays Using Heating And Cooling Steps," the disclosure of which is incorporated herein by reference. Briefly, this instrument utilizes a liquid handling system under computer control to make liquid transfers of enzyme stored at a controlled temperature in a first receptacle into a second receptacle whose temperature is controlled by the computer to conform to a certain incubation profile. The second receptacle stores the nucleic acid sequence(s) to be amplified plus the nucleotide triphosphates and primers. The computer includes a user interface through which a user can enter process parameters that control the characteristics of the various steps in the amplification sequence such as the times and temperatures of incubation, the amount of enzyme to transfer, etc.

An exemplary machine that can be employed utilizes temperature cycling without a liquid handling system because the enzyme need not be transferred at every cycle. Such a machine is described more completely in European Patent Application No. 236,069, published Sep. 9, 1987, the disclosure of which is incorporated herein by reference. Briefly, this instrument consists of the following system: 1. A heat-conducting container for holding a given number of tubes, preferably 500 µl tubes, which contain the reaction mixture of nucleotide triphosphates, primers, nucleic acid sequences, and enzyme. 2. A means to heat, cool, and maintain the heat-conducting container above and below room temperature, which means has an input for receiving a control signal for controlling which of the temperatures at or to which the container is heated, cooled or maintained. (These include Peltier heat pumps available from Materials Electronics Products Corporation of Trenton, N.J. or a water heat exchanger.) 3. A computer means (e.g., a microprocessor controller), coupled to the input of said means, to generate the signals that control automatically the amplification sequence, the temperature levels, and the temperature ramping and timing.

In some embodiments, a combined amplification and sequencing reaction ('DEXAS') directly from complex DNA mixtures is performed by using two thermostable DNA polymerases, one that favors the incorporation of deoxynucleotides over dideoxynucleotides, and one which has a decreased ability to discriminate between these two nucleotide forms. During cycles of thermal denaturation, annealing and extension, the former enzyme primarily amplifies the target sequence whereas the latter enzyme primarily performs a sequencing reaction. This method allows the determination of single-copy nuclear DNA sequences from amounts of human genomic DNA comparable to those used to amplify nucleotide sequences by the polymerase chain reaction. Thus, DNA sequences can be easily determined directly from total genomic DNA ("Direct DNA sequence determination from total genomic DNA", Kilger et al., Nucleic Acids Res. 1997 May 15; 25(10): 2032-2034).

Typically, amplification methods comprise contacting the nucleic acid sample with a compound or composition, such as a composition provided herein, comprising a polymerase in the presence of one or more primer sequences, amplifying the nucleic acid sample to generate a collection of amplified nucleic acid fragments, such as by PCR or equivalent automated amplification technique, and optionally separating the amplified nucleic acid fragments by size, such as by gel electrophoresis, and analyzing the gels for the presence of nucleic acid fragments, for example, by staining the gel with a nucleic acid-binding dye such as ethidium bromide. In some embodiments, the generation of the amplification product is detected in real-time using e.g. dsDNA binding fluorescent dye or detecting the presence of the amplification product using sequence-specific fluorescent labeled probes.

In some embodiments, following amplification by the methods provided, the amplified nucleic acid fragments are isolated for further use or characterization. This step is typically is accomplished by separation of the amplified nucleic acid fragments by size by any physical or biochemical means including gel electrophoresis, capillary electrophoresis, chromatography (including sizing, affinity and immunochromatography), density gradient centrifugation and immunoadsorption. Separation of nucleic acid fragments by gel electrophoresis provides a rapid and highly reproducible means of sensitive separation of a multitude of nucleic acid fragments, and permits direct, simultaneous comparison of the fragments in several samples of nucleic acids. In some embodiments, the nucleic acid fragment amplified by the methods provided is isolated and characterized.

In some embodiments, one or more of the amplified nucleic acid fragments are removed from the gel which was used for identification, according to standard techniques such as electroelution or physical excision. In some embodiments, the isolated unique nucleic acid fragments are then inserted into standard nucleotide vectors, including expression vectors, suitable for transfection or transformation of a variety of prokaryotic (bacterial) or eukaryotic (yeast, plant or animal including human and other mammalian) cells. In some embodiments, the nucleic acid molecules that are amplified and isolated using the compounds, compositions and methods provided herein are further characterized, for example, by sequencing (i.e., determining the nucleotide sequence of the nucleic acid fragments), or other standard methods in the art (see, e.g., U.S. Pat. Nos. 4,962,022 and 5,498,523, which are directed to methods of DNA sequencing).

In some embodiments, the stabilized polymerase compositions provided herein are suitable for use in a nucleic acid sequencing technique, such as, for example a dideoxy or Sanger sequencing assay. In some embodiments, the compositions provided herein are ready-to-use compositions for use in nucleic acid sequencing. For example, in some embodiments, the compositions provided herein comprise at least one DNA polymerase and a polymerase stabilizing agent disclosed herein, such as, for example, a zwitterionic stabilizer compound or cationic ester compound disclosed herein, and further comprise at least one deoxynucloside triphosphate, at least one dideoxynucloside triphosphate, magnesium salts and at least one nonionic detergent, wherein the stabilized polymerase is a DNA polymerase. In some embodiments, the polymerase stabilizing agent is a zwitterionic or cationic ester stabilizer of formula (I), (II), (III) or (IV). In some embodiments, the zwitterionic or cation ester stabilizer is selected from among a stabilizer listed in Table 1. In some embodiments, the storage stabilizing agent comprises Alanyl-Glutamine. In some embodiments, the storage stabilizing agent comprises 2-ethoxy-N-(2(2-hydroxyethoxy)ethyl)-N,N-dimethyl-2-oxoethanaminium bromide. In some embodiments, the storage stabilizing agent comprises Alanyl-Glutamine and 2-ethoxy-N-(2(2-hydroxyethoxy)ethyl)-N,N-dimethyl-2-oxoethanaminium bromide.

In some embodiments, the composition comprises one or more additional buffers suitable for performance of a nucleic acid sequencing assay. In some embodiments, the composition comprises one or more additional buffers, cofactors, and other agents suitable for use in nucleic acid sequencing. Selection of such additional agents useful for nucleic acid sequencing is within the knowledge of the skilled artisan. Addition of such agents should not negatively, or only minimally, affect the stabilization of the polymerase by the stabilizing agent provided herein. In some embodiments, the composition comprises one or more additional buffers suitable for performance of a nucleic acid sequencing assay. In some embodiments, the compositions provided herein are ready-to-use compositions for use in nucleic acid sequencing assay. For example, in some embodiments, the compositions provided herein comprise at least one DNA polymerase and a polymerase stabilizing agent disclosed herein, such as, for example, a zwitterionic stabilizer or cationic ester compound disclosed herein, and further comprise at least one deoxynucleoside triphosphates, at least one dideoxynucloside triphosphates, and one or more additional buffers or cofactors suitable for performance of a nucleic acid sequencing assay.

In some embodiments, nucleic acid sequencing methods provided herein comprises one or more steps. For example, provided is a method for sequencing a nucleic acid molecule comprising (a) mixing a nucleic acid molecule to be sequenced with one or more primers, one or more of the above-described compounds or compositions provided, one or more nucleotides and one or more terminating agents (such as a dideoxynucleotide) to form a mixture; (b) incubating the mixture under conditions sufficient to synthesize a population of molecules complementary to all or a portion of the molecule to be sequenced; and (c) separating the population to determine the nucleotide sequence of all or a portion of the molecule to be sequenced. Exemplary nucleic acid sequencing techniques which can be used with the present compositions include dideoxy sequencing methods such as those disclosed in U.S. Pat. Nos. 4,962,022 and 5,498,523.

In some embodiments, the compositions provided herein comprise one or more additional agents for the stabilization of the polymerase. Such agents are known in the art and include, but are not limited to, non-ionic detergents, nucleic acids (e.g. oligonucleotides, aptamers), inert proteins (e.g., bovine serum albumin (BSA) or fragments and derivatives thereof), antibodies that bind to one or more polymerases of the composition, polyvinyl pyrrolidone, and polyethylene glycol (PEG). In some embodiments, the compositions provided herein further comprises a thermoprotectant (e.g., ectoine, hydroxyectoine, mannosylglycerate, trehalose, betaine, glycerol, proline or diglycerol phosphate). In some embodiments, the compositions provided herein further comprises hydroxyectoine. In some embodiments, the compositions provided herein further comprises diglycerol phosphate.

In some embodiments, the compositions provided herein comprise a dye or colorimetric indicator, such as, for example, phenol red, ethidium bromide, cobalt chloride, Reichardt's dye, SYBR Green, EVAGREEN, BEBO, SYTO-9, SYTO-13, SYTO-82 TET, JOE, VIC, HEX, Texas Red, Cy3, Cy5, and Cy5.5 or a fluorogenic enzyme substrate.

In some embodiments, the compositions provided herein are employed for analysis of DNA. In some embodiments, the compositions provided herein are employed for the analysis of DNA length (e.g. RFLP analysis) or for analysis of the sequence of nucleic acids of a DNA molecule. In some embodiments, the compositions provided herein are employed for the diagnosis a disease or a condition. In some embodiments, the compositions provided herein are employed for the detection of a nucleic acid modification such as a deletion, an insertion, or a mutation. In some embodiments, the compositions provided herein are employed for the detection of a pathogen, such as a virus, a fungus, or a bacterial pathogen.

Kits and Articles of Manufacture

In some embodiments, the compositions provided herein are assembled into kits for use in nucleic acid amplification or sequencing. Sequencing kits according to the present invention comprise a carrier means, such as a box, carton, tube or the like, having in close confinement therein one or more container means, such as vials, tubes, ampules, bottles and the like, wherein a first container means contains a stable composition comprising a mixture of reagents, at working concentrations, which are at least one thermostable DNA polymerase, a polymerase stabilizing agent provided herein, at least one buffer salt, at least one deoxynucleoside triphosphate, at least one dideoxynucleoside triphosphate, and optionally at least one antibody which specifically binds to at least one thermostable DNA polymerase present in the compositions. The sequencing kits can further comprise additional reagents and compounds necessary for carrying out standard nucleic sequencing protocols, such as pyrophosphatase, agarose or polyacrylamide media for formulating sequencing gels, and other components necessary for detection of sequenced nucleic acids (See U.S. Pat. Nos. 4,962,020 and 5,498,523, which are directed to methods of DNA sequencing). In some embodiments, the polymerase stabilizing agent is a zwitterionic or cationic ester stabilizer of formula (I), (II), (III), or (IV). In some embodiments, the polymerase stabilizing agent is a zwitterionic stabilizer is selected from among a zwitterionic or cationic stabilizing agent listed in Table 1. In some embodiments, the polymerase stabilizing agent is Alanyl-Glutamine. In some embodiments, the polymerase stabilizing agent is 2-ethoxy-N-(2(2-hydroxyethoxy)ethyl)-N,N-dimethyl-2-oxoethanaminium bromide. In some embodiments, the polymerase stabilizing agent comprises Alanyl-Glutamine and 2-ethoxy-N-(2(2-hydroxyethoxy)ethyl)-N,N-dimethyl-2-oxoethanaminium bromide.

In some embodiments, kits provided herein comprise carrier means, such as a box, carton, tube or the like, having in close confinement therein one or more container means, such as vials, tubes, ampules, bottles and the like, wherein a first container means contains a stable composition comprising a mixture of reagents, at working concentrations, which are at least one DNA polymerase and at least one polymerase stabilizing agent provided herein. In some embodiments, the amplification kits provided further comprise additional reagents and compounds necessary for carrying out standard nucleic amplification protocols (See e.g., U.S. Pat. Nos. 4,683,195 and 4,683,202, which are directed to methods of DNA amplification by PCR).

EXAMPLES

These examples are provided for illustrative purposes only and not to limit the scope of the claims provided herein.

Example 1

Stabilization of Chemically-Modified Hot-Start Taq Polymerase

In this example, the ability of various formulations to stabilize Roche FastStart Taq polymerase at room temperature and 45° C. was tested.

Roche FastStart Taq polymerase (stored at −20° C. in 50% glycerol) was mixed in a 1:4 ratio with a range of liquid stabilizer solutions as set forth in Table 4 and incubated at both room temperature and 45° C. A non-protected sample was also included where the polymerase was mixed with an additional quantity of its storage buffer. At various time points, aliquots were taken from the stabilized enzyme solutions and used to perform end-point PCR assays. At each time point, the stabilized enzymes were compared to a frozen positive control enzyme in the same assay.

For end-point PCR, a multiplex assay using three primer sets to generate 3 different size fragments of the GAPDH gene was used. Typical PCR reactions contained the following: 1× Roche PCR reaction buffer, 10 ng human genomic DNA, 300 µM dNTPs, 240 nM GAPDH primer set A, 600 nM GAPDH primer set B, 1.2 µM GAPDH primer set C, and 1 unit Roche FastStart Taq polymerase. Cycling conditions were 2 minutes at 95° C. followed by 35 cycles of 30 seconds at 95° C., 30 seconds at 56° C., 30 seconds at 68° C., followed by 5 minutes at 68° C. PCR products were run on 2% agarose gels and visualized using ethidium bromide.

TABLE 4

Formulations Tested

| Formulation | Components |
|---|---|
| 36 | 10% Sucrose, 6% Melezitose, 1% PVA (MW~30-70,000 and 87-90% hydrolyzed), 50 mM Tris pH 8, 25 mg/mL N,N-Dimethyl-N-(2-hydroxyethyl)-3-ammonium-propionate |
| 108 | 10% Sucrose, 6% Melezitose, 1% PVA (MW~30-70,000 and 87-90% hydrolyzed), 50 mM Tris pH 8 |
| 150 | 10% Sucrose, 6% Melezitose, 1% PVA (MW~30-70,000 and 87-90% hydrolyzed), 50 mM Tris pH 8, 25 mg/mL 1-methyl-4-hydroxypiperidinium-3-propionate |
| 189 | 10% Sucrose, 6% Melezitose, 2% PVA (MW~30-70,000 and 87-90% hydrolyzed), 100 mM Tris pH 8 |
| 199 | 10% Sucrose, 6% Melezitose, 2% PVA (MW~30-70,000 and 87-90% hydrolyzed), 100 mM Tris pH 8, 25 mg/mL N-(2-ethoxy-2-oxoethyl)-2-hydroxy-N,N-dimethylpropan-1-aminium bromide |
| c-102 | Sucrose, Melezitose, PVA, 50 mM 3-(4-hydroxy-1-methylpiperidinium-1-yl)propanoate |
| c-103 | Sucrose, Melezitose, PVA, 50 mM 4-(4-methylmorpholino-4-ium)butane-1-sulfonate |
| c-108 | Sucrose, Melezitose, PVA, 100 mM 3-(1-methylpyrrolidinium-1-yl)propanoate |
| c-111 | Sucrose, Melezitose, PVA, 100 mM N,N-dimethyl-N-(2-hydroxyethyl)-3-ammonium propionate |
| c-116 | Sucrose, Melezitose, PVA, 50 mM 3-((2,3-dihydroxypropyl)dimethylammonio)propanoate |
| c-127 | Sucrose, Melezitose, PVA, 50 mM 3-((2-hydroxypropyl)dimethylammonio)propanoate |
| c-136i | Sucrose, Melezitose, PVA, 50 mM 1-(2-ethoxy-2-oxoethyl)-1-methylpiperidinium bromide |
| c-146i | Sucrose, Melezitose, PVA, 50 mM 2-(cyclohexyldimethylammonio)acetate |
| c-147i | Sucrose, Melezitose, PVA, 50 mM 1-ethoxy-N-(2-(2-hydroxyethoxy)ethyl)-N,N-dimethyl-2-oxoethanaminium bromide |
| c-135i | Sucrose, Melezitose, PVA, 50 mM 4-(2-ethoxy-2-oxoethyl)-4-methylmorpholin-4-ium bromide |

TABLE 4-continued

Formulations Tested

| Formulation | Components |
|---|---|
| c-137i | Sucrose, Melezitose, PVA, 50 mM 1-(2-ethoxy-2-oxoethyl)-1-methylpyrrolidinium bromide |
| c-138i | Sucrose, Melezitose, PVA, 50 mM 1-(2-ethoxy-2-oxoethyl)-3-hydroxy-1-methylpiperidinium bromide |
| c-142i | Sucrose, Melezitose, PVA, 50 mM N-(2-cyanoethyl)-2-ethoxy-N,N-dimethyl-2-oxoethanaminium bromide |
| c-144i | Sucrose, Melezitose, PVA, 50 mM 2-ethoxy-N,N-diethyl-N-methyl-2-oxoethanaminium bromide |
| 129 (2.5 mg/ml c-131) | 10% Sucrose, 6% Melezitose, 1% PVA (MW~30-70,000 and 87-90% hydrolyzed), 50 mM Tris pH 8, 2.5 mg/mL 3-(4-methylmorpholino-4-ium)propane-1-sulfonate |
| 150 (2.5 mg/ml c-102) | 10% Sucrose, 6% Melezitose, 1% PVA (MW~30-70,000 and 87-90% hydrolyzed), 50 mM Tris pH 8, 2.5 mg/mL 1-methyl-4-hydroxypiperidinium-3-propionate |
| 199 (2.5 mg/ml c-143i) | 10% Sucrose, 6% Melezitose, 2% PVA (MW~30-70,000 and 87-90% hydrolyzed), 100 mM Tris pH 8, 2.5 mg/mL N-(2-ethoxy-2-oxoethyl)-2-hydroxy-N,N-dimethylpropan-1-aminium bromide |
| X-1 | 50 mM hydroxyectoine, 10 mM boric acid, 1 mM sodium tetraborate, pH 8 |
| X-1d | 50 mM hydroxyectoine, 5 mM boric acid, 0.5 mM sodium tetraborate, pH 8 |
| H-ect + tris + 1% PVA | 50 mM hydroxyectoine, 10 mM Tris pH 7.5, 1% PVA |
| H-ect + tris | 50 mM hydroxyectoine, 10 mM Tris pH 7.5 |

After 3 weeks incubation at both room temperature and 45° C., stabilized Roche FastStart Taq was compared with a frozen positive control using a multiplex end-point PCR assay for the GAPDH target gene. As shown in FIG. 1a, the enzyme stored with the 3 indicated stabilizers at room temperature performed almost (formulations 36, 199) or equally (formulation 150) as well as the frozen positive control enzyme. As shown in FIG. 1b, after 3 weeks at 45° C., the non-protected polymerase has lost activity while the polymerase stored in formulation 150 retains activity. The polymerase stored in formulation 108 also loses activity at this time, showing that the addition of the small molecule 1-methyl-4-hydroxypiperidinium-3-propionate in formulation 150 provides increased stability, as this is the only difference between these 2 formulations.

Figure 6:
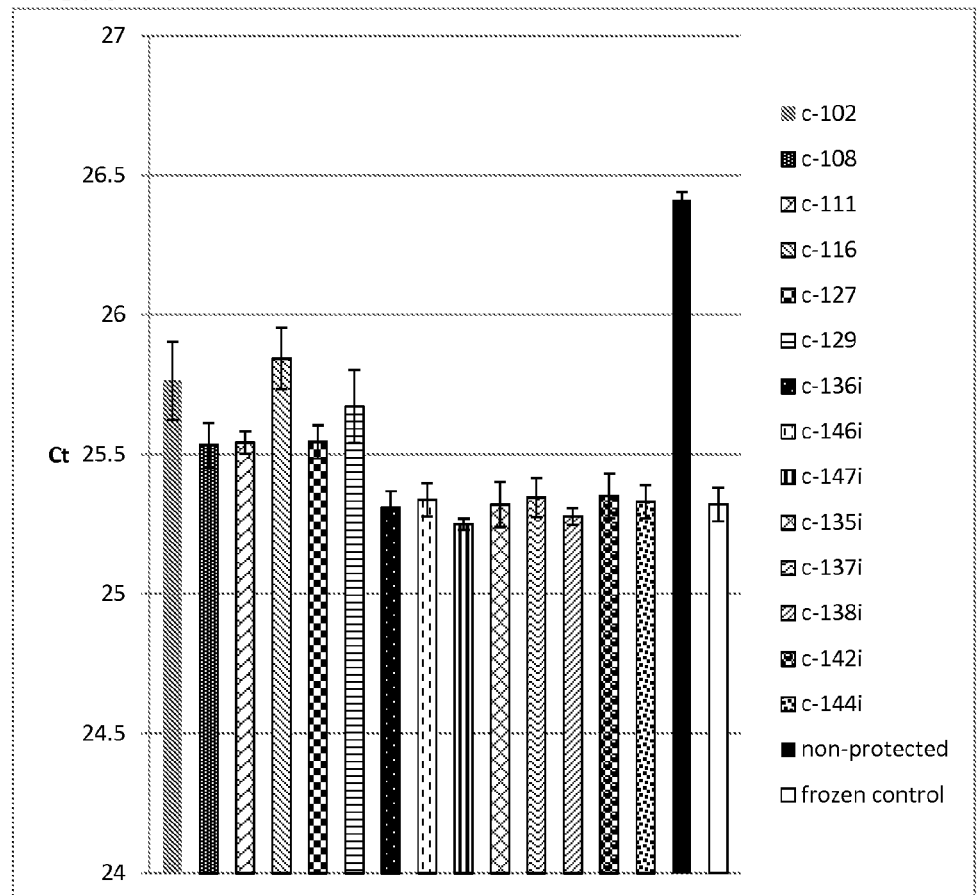
FIG. 6 illustrates 5 day stability of liquid-stabilized Promega GoTaq® at 45° C.
Figure 6:
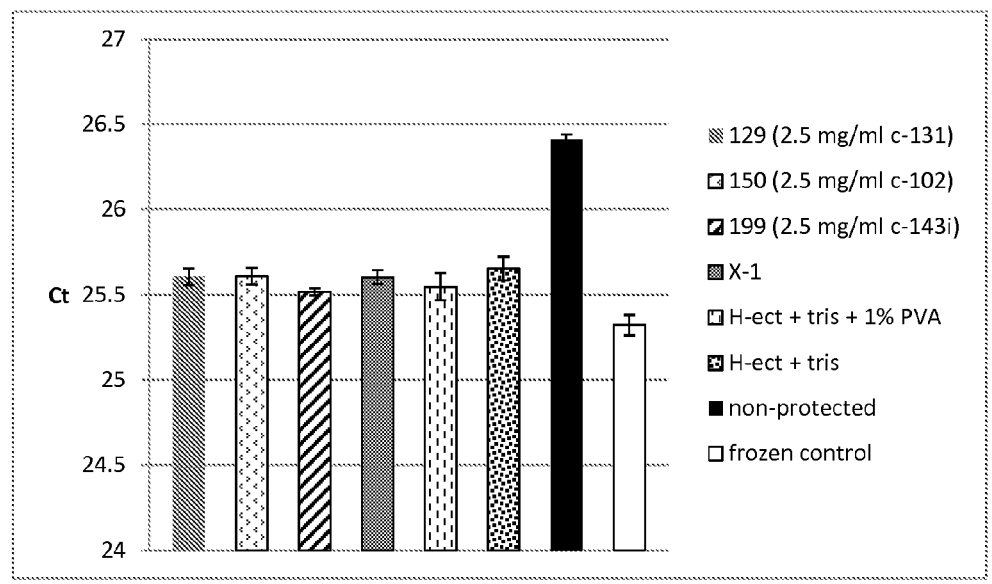
Figure 7:
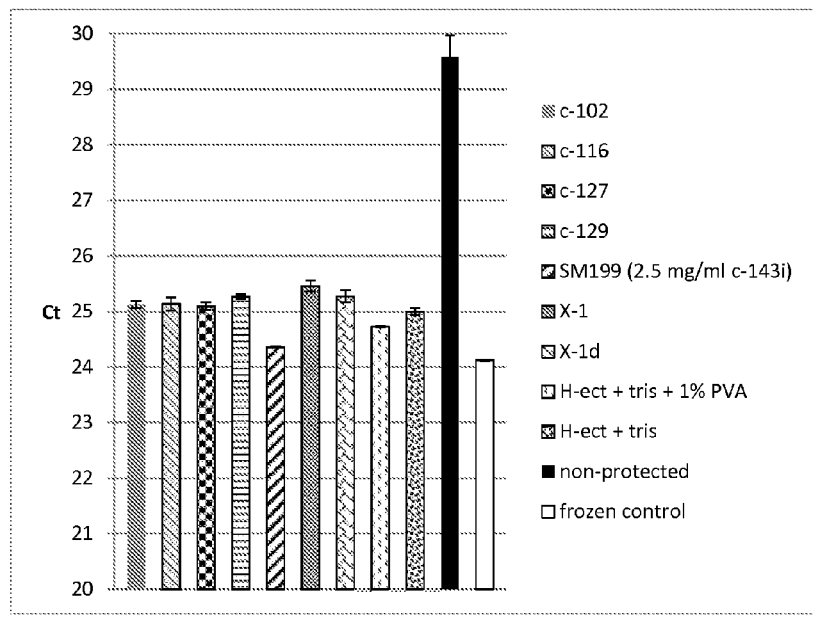
FIG. 7 illustrates 3 day stability of liquid-stabilized Promega GoTaq® at 45° C.
Figure 8:
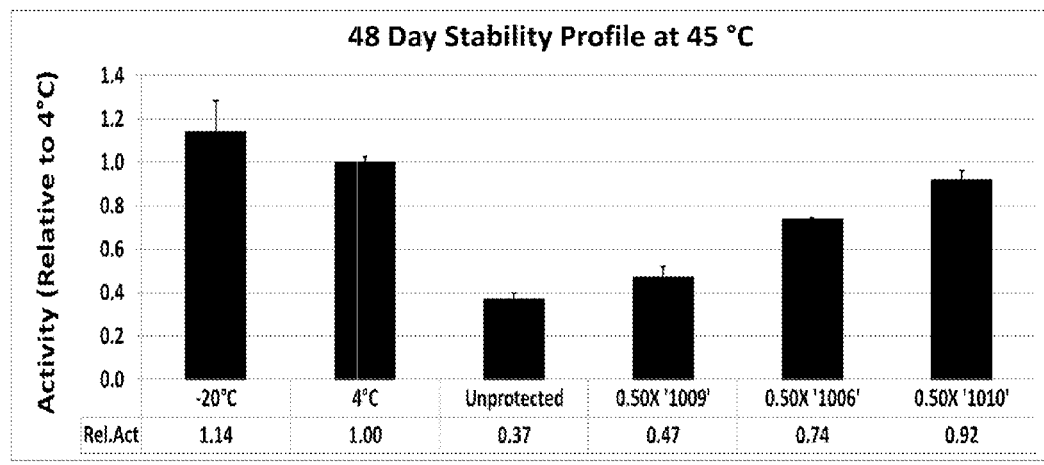
FIG. 8 illustrates 48 day stability of liquid formulations of Amplitaq Gold® containing 2-ethoxy-N-(2(2-hydroxyethoxy)ethyl)-N,N-dimethyl-2-oxoethanaminium bromide and alanyl-glutamine at 45° C.
Figure 9:
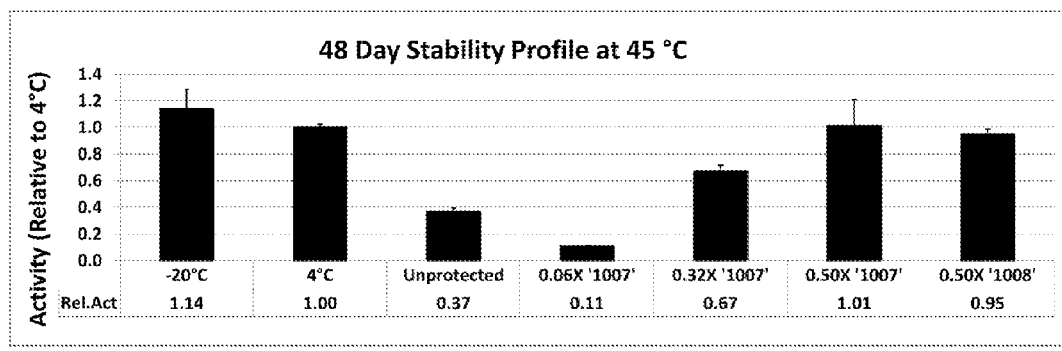
FIG. 9 illustrates 48 day stability of liquid formulations of Amplitaq Gold® containing alanyl-glutamine at 45° C.
Figure 10:
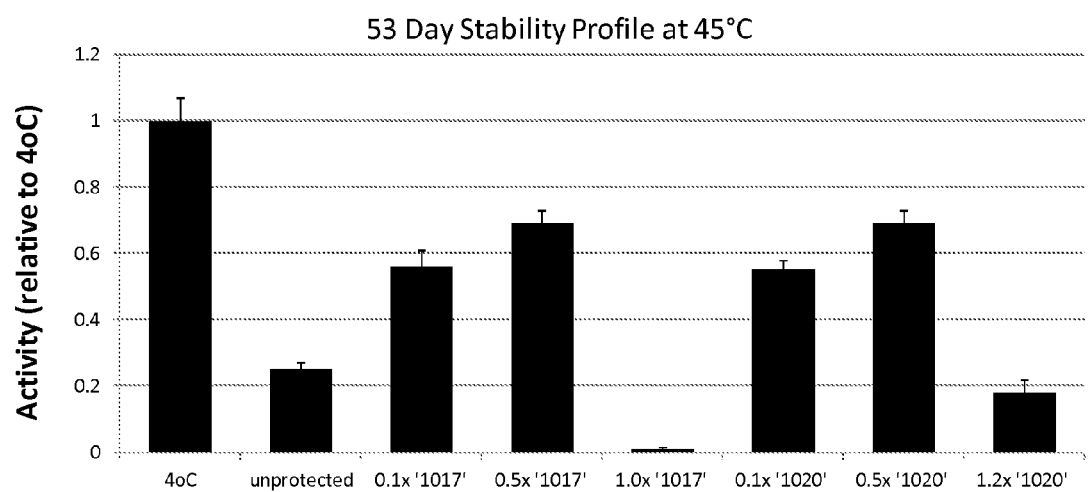
FIG. 10 illustrates 53 day stability of liquid formulations of Amplitaq Gold® containing ionic imidazolium compounds at 45° C.
Figure 11:
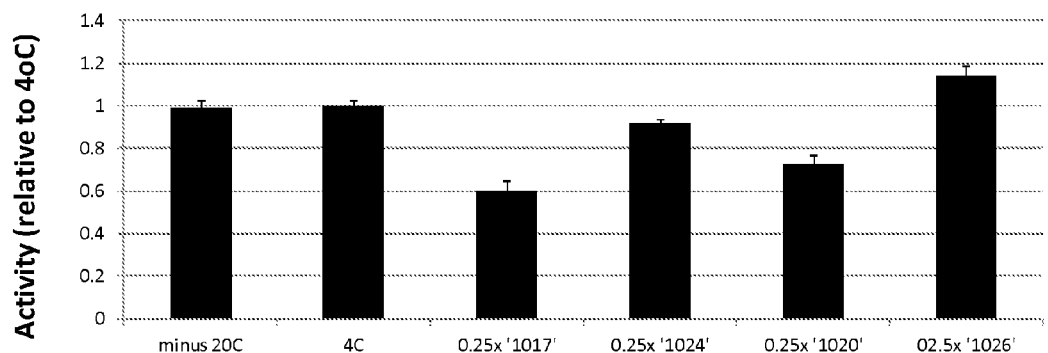
FIG. 11 illustrates 32 day stability of liquid formulations of Amplitaq Gold® containing ionic imidazolium compounds at 45° C.

FIG. 6 illustrates 5 day stability of liquid-stabilized Promega GoTaq® at 45° C. for the remaining formulations. FIG. 7 illustrates 3 day stability of liquid-stabilized Promega GoTaq® at 45° C.

Example 2

Stabilization of Antibody-Modified Hot-Start Taq Polymerase

Promega GoTaq® polymerase (stored at −20° C. in 50% glycerol) was mixed in a 1:4 ratio with a range of liquid stabilizer solutions as set forth in Table 4 (formulations 36, 108, 150, 189 and 199 were tested) and incubated at room temperature, 37° C., and 45° C. A non-protected sample was also included where the polymerase was mixed with an additional quantity of its storage buffer. In addition, SYBR® Green-based qPCR master mixes (MM) were made and stored at the indicated temperatures. These master mixes were made as a 2× concentration mix, to be used in qPCR reactions at 1× concentration. The master mixes contained reaction buffer (final reaction concentration: 20 mM Tris, 50 mM KCl, 2.5 mM MgCl2, 0.15% Triton X-100, pH 8.6), dNTPs (final reaction concentration: 200 nM), SYBR Green (final reaction concentration: 0.25×), Promega GoTaq® (final reaction concentration: 0.625 units), and the remaining volume was made up of the liquid stabilizer. At various time points, aliquots were taken from the stabilized enzyme solutions and/or the stabilized qPCR master mix solutions and tested using a SYBR Green-based qPCR assay.

For qPCR, a primer set was used to generate a fragment of the RNaseP gene using a human genomic DNA template. Typical qPCR reactions contained the following: 1× reaction buffer, dNTPs, SYBR® Green and Promega GoTaq® in the concentrations indicated above. In addition, the reactions contained 200 nM RNaseP primers and between 0.5 ng to 50 ng human genomic DNA. Reactions were run on an ABI7300 real-time PCR machine and cycling conditions were 5 minutes at 95° C. followed by 40 cycles of 10 seconds at 95° C., then 30 seconds at 60° C. Fluorescence data was obtained and used to calculate Ct values.

Figure 2:
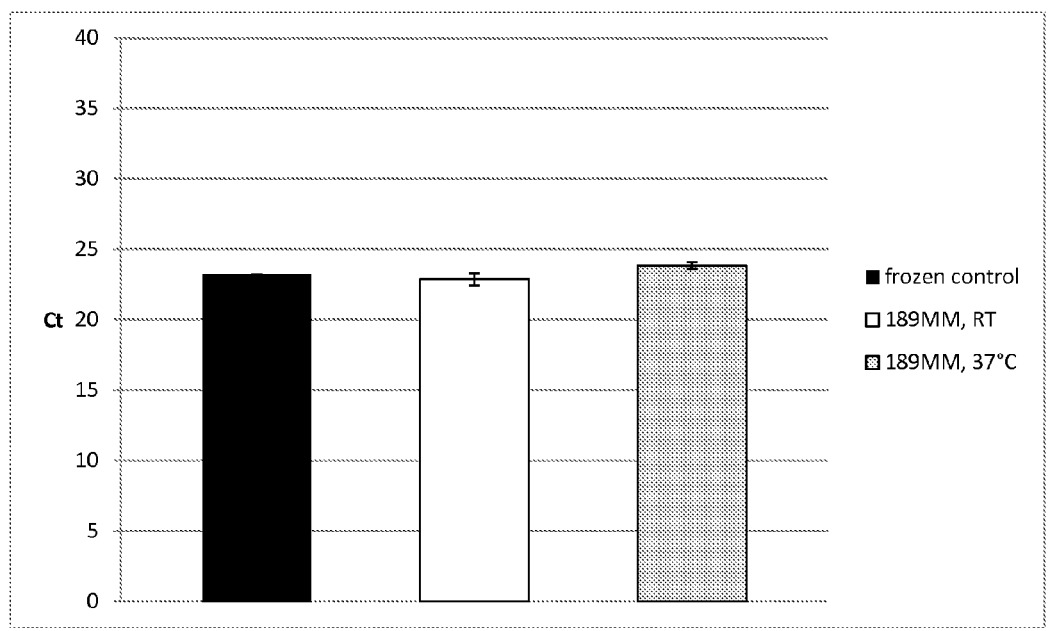
FIG. 2 illustrates 5 day stability of liquid-stabilized Promega GoTaq® at room temperature and 37° C.

After 5 days incubation at both room temperature and 37° C., stabilized Promega GoTaq® was compared to a frozen positive control using a SYBR Green-based qPCR assay for the human RNaseP gene. As illustrated in FIG. 2, the enzyme stabilized in master mix format performed as well as the positive control at both temperatures in amplifying the RNaseP target from 50 ng human genomic DNA.

Figure 3:
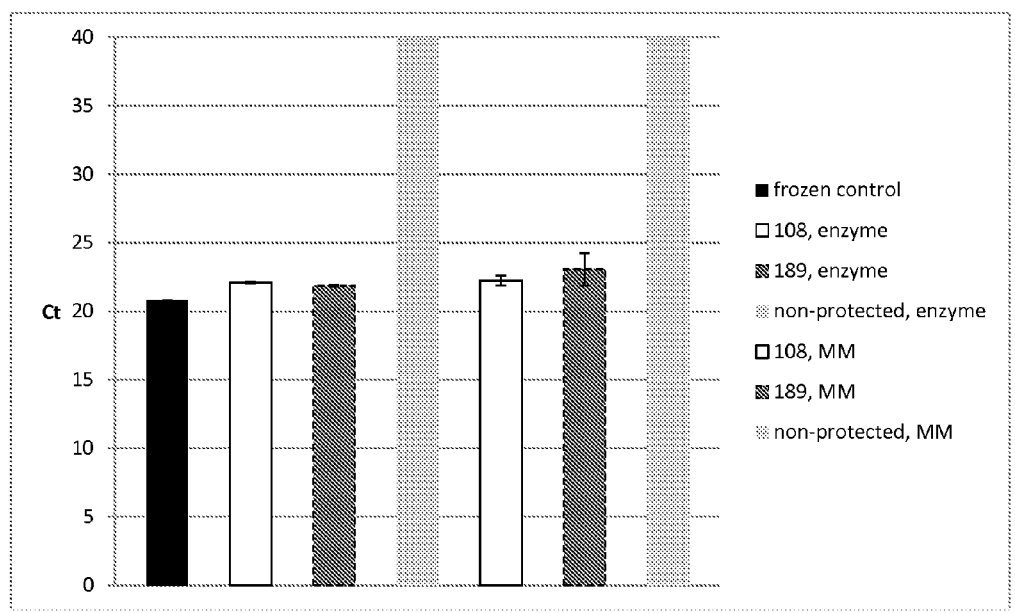
FIG. 3 illustrates 6 week stability of liquid-stabilized Promega GoTaq® at room temperature.

After 6 weeks incubation at room temperature, stabilized Promega GoTaq® was again compared to a frozen positive control using a SYBR® Green-based qPCR assay. As illustrated in FIG. 3, both the enzyme stabilized alone and in master mix format performed as well as the positive control in amplifying the RNaseP target from 50 ng human genomic DNA.

Figure 4:
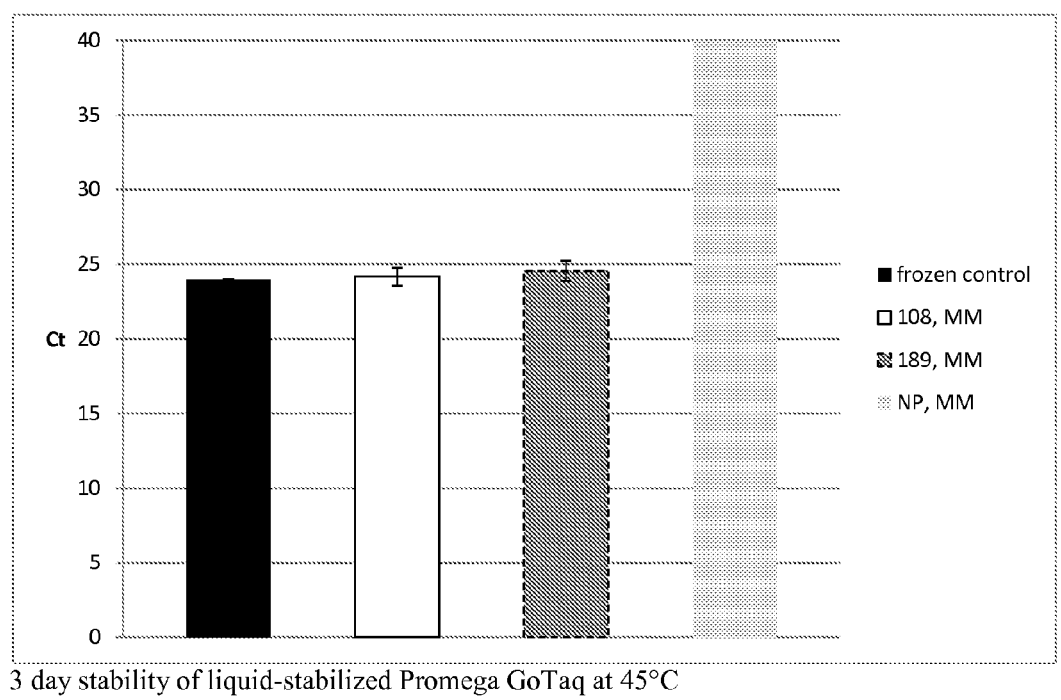
FIG. 4 illustrates 3 day stability of liquid-stabilized Promega GoTaq® at 45° C.
Figure 5:
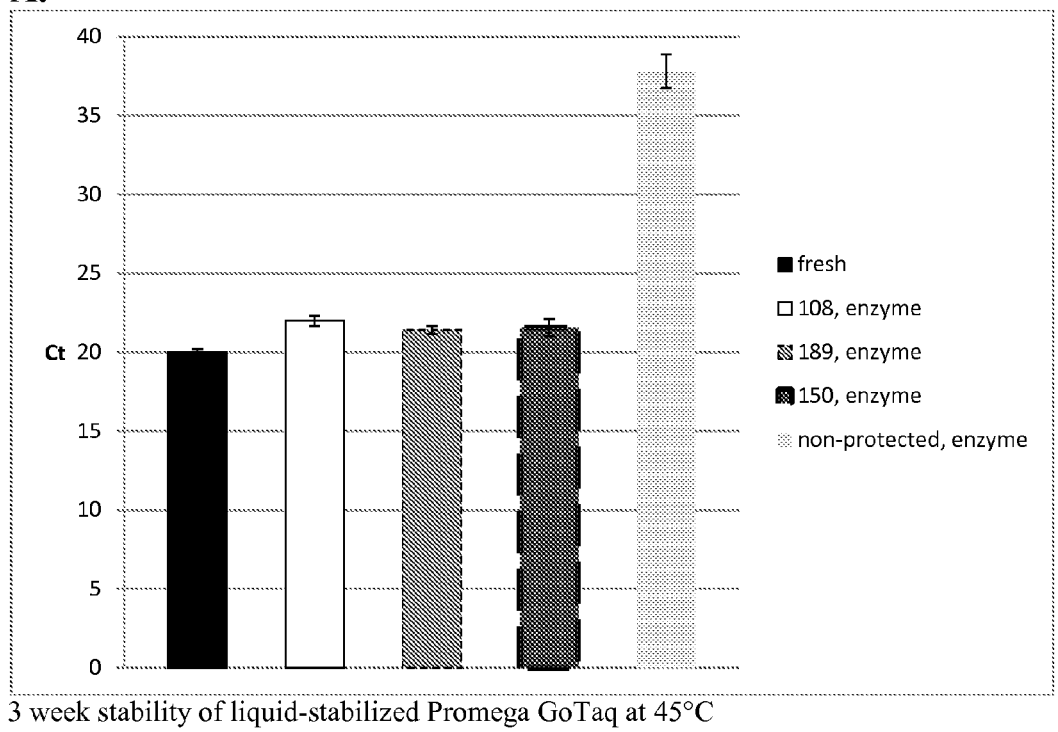
FIG. 5 illustrates 3 week stability of liquid-stabilized Promega GoTaq® at 45° C.
Figure 5:
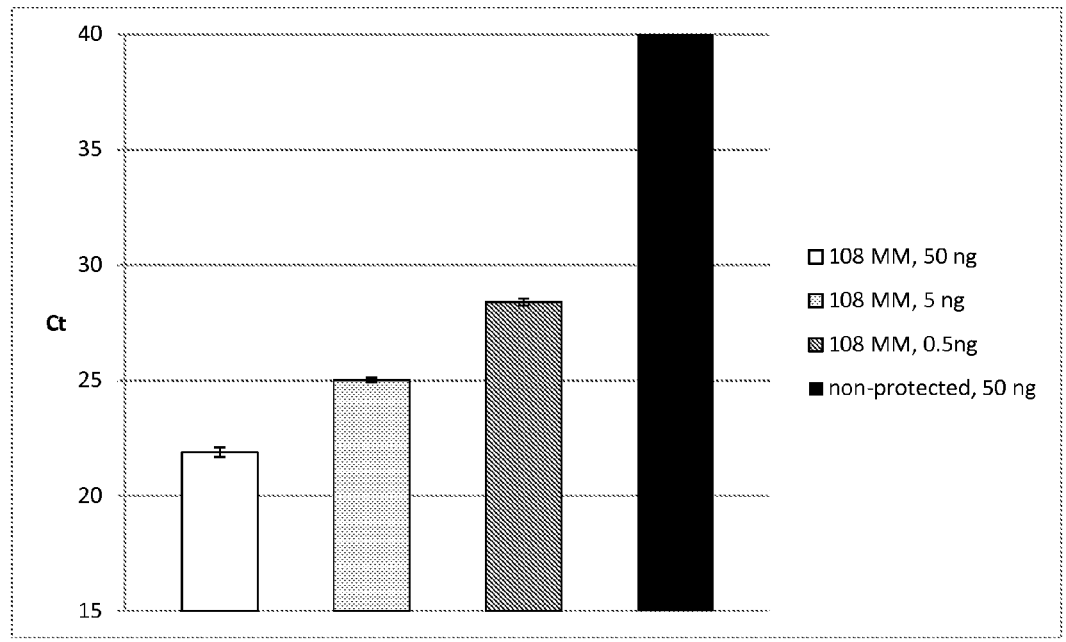

After 3 days incubation at 45° C., stabilized Promega GoTaq® was again compared to a frozen positive control using a SYBR Green-based qPCR assay. As illustrated in FIG. 4, the enzyme stabilized in master mix format performed as well as the positive control in amplifying the RNaseP target from 50 ng human genomic DNA while the non-protected enzyme failed to amplify the target after 40 amplification cycles. After 3 weeks incubation at 45° C., the stabilized enzyme alone performs as well as the frozen positive control and considerably better than the non-protected enzyme as seen in FIG. 5a. In FIG. 4, it is shown that that in master mix format, the non-protected enzyme fails to amplify the RNaseP target gene at all template concentrations tested, while the enzyme stabilized in master mix format shows a consistent amplification of each 10-fold dilution of the template DNA.

After 5 days incubation at 45° C., stabilized Promega GoTaq was again compared to a frozen positive control using a SYBR Green-based qPCR assay. As seen in FIGS. 6a and 6b, the stabilized enzyme alone performs within 0.5 Ct values of the frozen positive control while the non-protected enzyme performs approximately 1 Ct value worse than the frozen positive control. In FIG. 7, we see that the enzyme stabilized in the same formulations in master mix format perform within 1 Ct value of the frozen positive control while the non-protected sample performs significantly worse.

Example 3

Synthesis of 3-((2-hydroxyethyl)dimethylammonio)propanoate

In this example, the following method was performed for the synthesis of 3-((2-hydroxyethyl)dimethylammonio)propanoate (compound 111) having the structure:

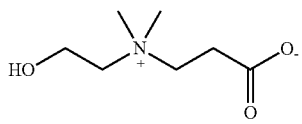

A 125 mL Erlenmeyer flask equipped with a stir bar was charged with 8.91 g (0.10 moles) of 2-(dimethylamino) ethanol. 40 mL of dichloromethane was added and the solution mixed on a stirplate. 7.93 g (0.11 moles) of acrylic acid was weighed into a 50 mL test tube and 20 mL of dichloromethane added to dilute the acid. The acrylic acid solution was added dropwise to the flask containing the 2-(dimethylamino)ethanol at room temperature with stirring. Upon complete addition the flask was sealed with a septum with a vent to relieve any pressure that built up. The solution was stirred at room temperature for 72 hours and a white precipitate developed over time. The solid was collected on a sintered glass medium porosity filter and washed two times with ethyl acetate. The solid was dried in a dry oven at 50° C. to give 5.88 g (36% yield) of a white solid. Mass Spec=162.2 m/z (M+H).

Example 4

Synthesis of 3-(4-hydroxy-1-methylpiperidinium-1-yl)propanoate

The following method was performed for the synthesis of 3-(4-hydroxy-1-methylpiperidinium-1-yl)propanoate (compound 102) having the structure:

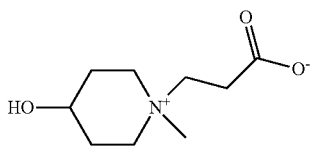

A 125 mL Erlenmeyer flask equipped with a stir bar was charged with 5.76 g (0.050 moles) of 4-hydroxy-1-methylpiperidine. 30 mL of dichloromethane was added and the solution mixed on a stirplate. 3.96 g (0.055 moles) of acrylic acid was weighed into a test tube and 10 mL of dichloromethane added to dilute the acid. The acrylic acid solution was added dropwise to the flask containing the 4-hydroxy-1-methylpiperidine at room temperature with stirring. Upon complete addition of the acrylic acid the flask was sealed with septum with a vent to relieve any potential pressure that might build up. The solution was stirred at room temperature for 96 hours during which time a white precipitate developed. The precipitate was collected by vacuum filtration using a sintered glass medium porosity filter and washed twice with 50 mL portions of ethyl acetate. The white solid was dried in an oven at 50° C. to give 6.14 g (90% yield) of 3-(4-hydroxy-1-methylpiperidinium-1-yl)propanoate. Mass Spec=188.2 m/z (M+H).

Example 5

Synthesis of 2-((2-hydroxypropyl)dimethylammonio)acetate

In this example, the following method was performed for the synthesis of 2-(2-hydroxypropyl)dimethylammonio) acetate (compound 143) having the structure:

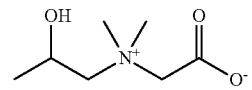

A 125 mL Erlenmeyer flask was equipped with a stir bar was charged with 10.3 g (0.10 moles) of 1-dimethylamino-2-propanol. 40 mL of dichloromethane was added and the solution mixed on a stirplate. 16.7 g (0.10 moles) of ethyl bromoacetate was weighed into a 50 mL test tube and 20 mL of dichloromethane added to dilute the ethyl bromoacetate. The ethyl bromoacetate solution was added dropwise with stirring at room temperature to the solution of the 1-dimethylamino-2-propanol. Following complete addition the flask was sealed with septum and a needle vent to relieve any potential pressure that built up. The solution was stirred at room temperature for 96 hours during which time a white precipitate developed. The white solid was collected by vacuum filtration using a medium porosity sintered glass funnel washed twice with 50 mL of ethyl acetate and then dried in an oven at 50° C. to give 11.49 g (71.2%). Mass Spec=176.3 m/z (M+CH3, likely a methanol adduct).

Example 6

Synthesis of 4-(2-Ethoxy-2-oxoethyl)-4-methylmorpholin-4-ium bromide

In this example, the following method was performed for the synthesis of 4-(2-Ethoxy-2-oxoethyl)-4-methylmorpholin-4-ium bromide (compound 135) having the structure:

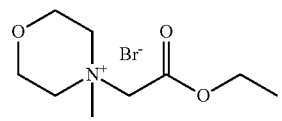

5.06 g (0.050 mol) of 4-Methylmorpholine was dissolved in 40 mL dichloromethane and cooled to 0° C. in an ice-water bath. To this stirred solution, 8.35 g of ethyl bromoacetate (0.050 mol) in 20 mL of dichloromethane was added dropwise and the mixture was then allowed to warm to room temperature. The clear solution started to form white precipitate after ~5 minutes of stirring at room temperature. The resulting mixture was stirred for another 3 h. The precipitate was isolated by vacuum filtration using a 30 mL medium porosity glass fritted funnel and washed 3 times with 30 mL of acetone and dried over CaSO4 in a desiccation chamber to give 12.07 g of the product as a white solid. Positive mode ESI/MS: m/z=188.3 (M+, minus Br); confirmed by $^1$H NMR Example 7

Synthesis of 1-(2-ethoxy-2-oxoethyl)-1-methylpiperidinium bromide

In this example, the following method was performed for the synthesis of 1-(2-ethoxy-2-oxoethyl)-1-methylpiperidinium bromide (compound 136) having the structure:

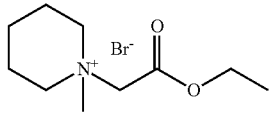

4.96 g of 1-methylpiperidine (0.050 mmol) was dissolved in 40 mL dichloromethane and cooled to 0° C. in an ice-water bath. To this stirred solution was added 8.35 g of ethylbromoacetate (0.050 mmol) in 20 mL of dichloromethane dropwise via a syringe. Following addition the mixture was removed from the ice-water bath and stirred at room temperature overnight. The resulting white precipitate was washed twice with 30 mL of acetone and dried over CaSO4 in a desiccation chamber to give 9.98 g, 75% yield of the product as a white solid. Positive mode ESI/MS: m/z=186.3 (M+, minus Br); confirmed by $^1$H NMR.

Example 8

Synthesis of N-(2-ethoxy-2-oxoethyl)-N,N-dimethylcyclohexanaminium bromide

In this example, the following method was performed for the synthesis of N-(2-ethoxy-2-oxoethyl)-N,N-dimethylcyclohexanaminium bromide (compound 146) having the structure:

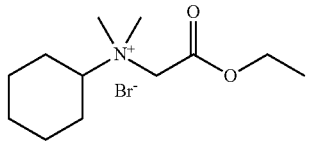

6.36 g (0.050 moles) of N,N-dimethylcyclohexylamine was dissolved in 40 mL dichloromethane and cooled to 0° C. in an ice-water bath. To this stirred solution, was added 8.35 g of ethylbromoacetate (0.050 mmol) in 20 mL of dichloromethane dropwise via a syringe. Following complete addition, the mixture was removed from the ice-water bath and stirred at room temperature overnight. The resulting white precipitate was washed three times with 30 mL of acetone and dried over CaSO4 in a desiccation chamber to give 14.5 g of the product as a very light yellow crystalline solid. Positive mode ESI/MS: m/z=214.4 (M+, minus Br); confirmed by $^1$H NMR.

Example 9

Synthesis of 1-(2-ethoxy-2-oxoethyl)-3-hydroxy-1-methylpiperidium bromide

In this example, the following method was performed for the synthesis of 1-(2-ethoxy-2-oxoethyl)-3-hydroxy-1-methylpiperidium bromide (compound found in formulation 162) having the structure:

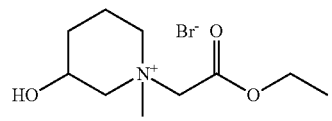

11.52 g (0.100 mol) of 3-Hydroxy-1-Methylmorpholine was dissolved in 80 mL dichloromethane and cooled to 0° C. in an ice-water bath. To this stirred solution, 16.7 g of ethyl bromoacetate (0.100 mol) in 40 mL of dichloromethane was added dropwise and the mixture was then allowed to warm to room temperature. The clear solution started to form white precipitate after ~5 minutes of stirring at room temperature. The reaction was allowed to proceed overnight then the precipitate formed was isolated by vacuum filtration using a 60 mL medium porosity glass fritted funnel. The solid was washed 3 times with 30 mL of acetone and dried over CaSO$_4$ in a desiccation chamber to give 22.18 g of the product as a white solid. Positive mode ESI/MS: m/z=188.3 (M$^+$-CH2) 202.3 (M+); $^1$H NMR is very complicated because of the diastereomers formed during the alkylation.

Example 10

Synthesis of 2-ethoxy-N-(2(2-hydroxyethoxy)ethyl)-N,N-dimethyl-2-oxoethanaminium bromide In this example, the following method was performed for the synthesis of 2-ethoxy-N-(2(2-hydroxyethoxy)ethyl)-N,N-dimethyl-2-oxoethanaminium bromide (compound found in formulation 155) having the structure:

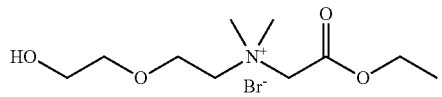

13.32 g (0.100 mmol) of 2-[2-(Dimethylamino)ethoxy]ethanol was dissolved in 80 mL of dichloromethane and cooled to 0° C. in an ice bath. To the stirred solution, 16.7 g of ethyl-2-bromoacetate (0.100 mmol) in 40 mL of dichloromethane was added dropwise over a period of 15 minutes. The ice bath was removed and the mixture allowed to warm to room temperature. A white solid began to precipitate from the solution and the reaction allowed to proceed for an additional 8 hours. The solid was collected by vacuum using a 60 mL medium porosity fritted glass funnel and washed with three 30 mL portions of ethyl acetate. The solid was dried in an oven to give 28.10 g of a white solid. Positive mode ESI/MS: m/z=220.3 (M+, minus Br), $^1$H NMR: 1.306 (triplet, 3H), 3.368 (singlet, 6H), 3.630 (broad triplet, 2H), 3.772 (broad triplet, 2H), 3.886 (broad triplet, 2H), 3.981 (broad triplet, 2H), 4.305 (quartet, 2H), 4.394 (singlet, 2H).

Example 11

Test formulations SM-0001006, SM-0001007, SM-0001008, SM-0001009, SM-001010, SM-001017, SM-001020, SM-001024, and SM-001026, were mixed in equal volume with the 5× concentration of PCR Master Mix and Amplitaq GOLD enzyme such that the final concentration of Master Mix was 2.5× and the final concentration of enzyme was 2.5 U/μL. All preparative steps were conducted as per the manufacturer's instructions and prepared and quantified in triplicate.

TABLE 5

Formulations tested

| Class | Poly-saccharides | Zwitterions | Polymer | pH | cationic ester and/or | ionic imidazolium compound | Albumin |
|---|---|---|---|---|---|---|---|
| SM-0001009 | 10% Sucrose, 6% Melezitose | | 1% PVA (30-70K and 87-90% hydrolyzed) | 8 | 25 mg/mL 2-Ethoxy-N-(2-(2-hydroxyethoxy)ethyl)-N,N-dimethyl-2-oxoethanaminium bromide | | |
| SM-0001006 | 10% Sucrose, 6% Melezitose | | 1% PVA (30-70K and 87-90% hydrolyzed) | 8 | 25 mg/mL 2-Ethoxy-N-(2-(2-hydroxyethoxy)ethyl)-N,N-dimethyl-2-oxoethanaminium bromide | | 0.5 mg/mL BSA |
| SM-0001010 | 10% Sucrose, 6% Melezitose | 2M Alanyl-Glutamine | 1% PVA (30-70K and 87-90% hydrolyzed) | 8 | 25 mg/mL 2-Ethoxy-N-(2-(2-hydroxyethoxy)ethyl)-N,N-dimethyl-2-oxoethanaminium bromide | | 1 mg/mL BSA |
| SM-0001007 | | 2M Alanyl-Glutamine | | 8 | | | |
| SM-0001008 | | 2M Alanyl-Glutamine | | 8 | | | 2 mg/mL BSA |
| SM-0001017 | | | | 8 | | 0.01-2M 1-benzyl-3-butyl-1H-imidazol-3-ium bromide | |
| SM-0001020 | | | | 8 | | 0.01-2M 3-(2-hydroxyethyl)-1-methyl-1H-imidazol-3-ium bromide | |
| SM-0001024 | 10% Sucrose, 6% Melezitose | | 1% PVA (30-70K and 87-90% hydrolyzed) | 8 | 25 mg/mL 2-Ethoxy-N-(2-(2-hydroxyethoxy)ethyl)-N,N-dimethyl-2-oxoethanaminium bromide | 0.01-2M 1-benzyl-3-butyl-1H-imidazol-3-ium bromide | |
| SM-0001026 | 10% Sucrose, 6% Melezitose | | 1% PVA (30-70K and 87-90% hydrolyzed) | 8 | 25 mg/mL 2--Ethoxy-N-(2-(2-hydroxyethoxy)ethyl)-N,N-dimethyl-2-oxoethanaminium bromide | 0.01-2M 3-(2-hydroxyethyl)-1-methyl-1H-imidazol-3-ium bromide | |

Fluorescence measurements were made with the following settings: excitation wavelength of 485±20 nm and an emission wavelength of 528±20 nm. Fluorescence from the no enzyme controls were subtracted from the sample measurements. Data is shows in FIGS. 8-11. The data shows that the cationic ester compounds stabilizes polymerase by itself and acts synergistically with zwitterionic and ionic imidazolium compounds tested.

Enzyme Activity Measurements

At the specified time points for enzyme activity measurement, 5 μl of the sample was subjected to the activation procedure recommended by the manufacturer, diluted 1:5 into the remaining reaction reagents provided that included target DNA and fluorescently labeled probes used to detect the primer extension products. Samples were incubated at 65° C. for 30 minutes followed by a 4° C. cool-down.

After samples reached 4° C., the reaction was terminated by the addition of 10 μl of EDTA. 50 μl of each sample was transferred to a black 96-well plate containing 50 μl of 12×SYBR Green Solution per well (12×SYBR Green; 10 mM Tris-HCl, pH 8.0; 1 mM EDTA). Plates were incubated for 10 minutes at 50° C. in a pre-heated BioTek plate reader.

Example 12

Synthesis of 3-(2-hydroxyethyl)-1-methyl-1H-imidazol-3-ium bromide

In this example, the following method was performed for the synthesis of 3-(2-hydroxyethyl)-1-methyl-1H-imidazol-3-ium bromide (compound #1020) having the structure:

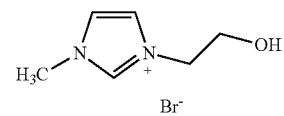

A 35 mL glass pressure tube (Ace Glass Cat#8648-07) containing a stir bar was charged with 4.105 g (0.050 moles) of 1-methylimdazole followed by 6.249 g (0.050 moles) of 2-bromoethanol. The tube was sealed with a threaded Teflon plug and an O-ring and the tubes were placed in an oil bath on a VWR stirring hot plate. The temperature was raised to 90° C. and maintained at this temperature for 16 hours during which time the solution became very viscous and the stir bar had stopped. The tube was removed from the oil bath and mixed vigorously on vortex mixer then heated for an additional hour at 90° C. in the oil bath. The tube was then removed from the bath and allowed to cool during which time the product solidified. The solid was dissolved in 15 mL of water and extracted with equal volumes of ethyl acetate three times followed by rotary evaporation to remove the water and residual ethyl acetate to give 9.88 grams (95.4%) of the 1-(2-hydroxyethyl)-3-methylimidazolium bromide as light yellow colored solid. Mass Spectrum (positive mode) 127.2 m/z corresponding to M+ minus bromide.

Example 13

Synthesis of 1-benzyl-3-butyl-1H-imidazol-3-ium bromide

In this example, the following method was performed for the synthesis of 1-benzyl-3-butyl-1H-imidazol-3-ium bromide (compound #1017) having the structure:

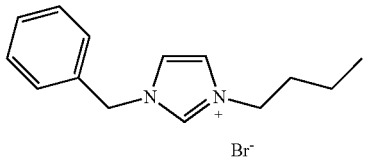

A 35 mL glass pressure tube (Ace Glass Cat#8648-07) containing a stir bar was charged with 3.955 g (0.025 moles) of 1-benzylimdazole followed by 3.425 g (0.025 moles) of 1-bromobutane. The tube was sealed with a threaded Teflon plug and an O-ring and the tubes were placed in an oil bath on a VWR stirring hot plate. The temperature was raised to 90° C. and maintained at this temperature for 16 hours during which time the solution became viscous and solidified. The tube was removed from the oil bath and allowed to cool. The solidified product was crushed to give 7.22 g (98%) of the 1-benzyl-3-butylimidazolium bromide as a very light yellow colored solid. Mass Spectrum (ESI, positive mode)=229.3 m/z corresponding to M+ minus bromide.

The examples and embodiments described herein are for illustrative purposes only and various modifications or changes suggested to persons skilled in the art are to be included within the spirit and purview of this application and scope of the appended claims.

What is claimed is:

1. A liquid composition comprising a polymerase and a storage stabilizing agent, wherein the storage stabilizing agent comprises at least one cationic ester compound selected from the group consisting of:
   [i] 1-(2-ethoxy-2-oxoethyl)-3-hydroxy-1-methylpiperidium bromide,
   [ii] N-(2-cyanoethyl)-2-ethoxy-N,N-dimethyl-2-oxoethanaminium bromide,
   [iii] 2-ethoxy-N,N-diethyl-N-methyl-2-oxoethanaminium bromide,
   [iv] N-(2-ethoxy-2-oxoethyl)-N,N-dimethylcyclohexanaminium bromide, and
   [v] 2-ethoxy-N-(2-(2-hydroxyethoxy)ethyl)-N,N-dimethyl-2-oxoethanaminium bromide.

2. The composition of claim 1, wherein the composition comprises a disaccharide, a trisaccharide, or a combination of a disaccharide and a trisaccharide.

3. The composition of claim 2, wherein the disaccharide is sucrose, or the trisaccharide is melezitose or raffinose.

4. The composition of claim 1, wherein the composition comprises a polymer.

5. The composition of claim 4, wherein the polymer is polyvinyl alcohol (PVA).

6. The composition of claim 1, further comprising BSA.

7. The composition of claim 1, further comprising a buffering agent.

8. The composition of claim 7, wherein the buffering agent is selected from the group consisting of Tris, MOPS, HEPES, TAPS, Bicine, Tricine, TES, PIPES, MES, and combinations thereof.

9. The composition of claim 1, wherein the polymerase retains the same activity when stored at room temperature for at least two weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, or at least 1 year compared to the activity of the polymerase when stored at a temperature of −20° C. for the same time period.

10. The composition of claim 1, further comprising one or more additional reagents selected from the group consisting of a buffering agent, reducing agent, a non-ionic detergent, a salt, at least one dNTP, a primer, and combinations thereof.

11. The composition of claim 1, comprising about 0.05-5M alanyl-glutamine, about 0.5-10% sucrose, about 0.5-10% melezitose, about 0.1-1% PVA, and about 1-25 mg/ml 2-ethoxy-N-(2(2-hydroxyethoxy)ethyl)-N,N-dimethyl-2-oxoethanaminium bromide.

* * * * *